United States Patent [19]
Lowe et al.

[11] Patent Number: 6,043,255
[45] Date of Patent: Mar. 28, 2000

[54] MUSCARINIC ANTAGONISTS

[75] Inventors: Derek B. Lowe, Scotch Plains; Wei K. Chang, Livingston; Joseph A. Kozlowski, Princeton; Joel G. Berger, Cedar Grove; Robert McQuade, Scotch Plains; Allen Barnett, Pine Brook; Margaret Sherlock, Bloomfield; Wing Tom, Cedar Grove; Sundeep Dugar, Bridgewater; Lian-Yong Chen, Edison; John W Clader, Cranford; Samuel Chackalamannil, East Brunswick; Yuguang Wang, North Brunswick; Stuart W. McCombie, Caldwell; Jayaram R. Tagat, Westfield; Susan F. Vice, Mountainside, all of N.J.; Wayne Vaccaro, Yardley, Pa.; Michael J. Green, Encinitas, Calif.; Margaret E. Browne, Bloomfield, N.J.; Theodros Asberom, West Orange, N.J.; Craig D. Boyle, Bridgewater, N.J.

[73] Assignee: Schering Corporation, Kenilworth, N.J.

[21] Appl. No.: 09/266,079

[22] Filed: Mar. 10, 1999

Related U.S. Application Data

[60] Division of application No. 08/700,628, Aug. 8, 1996, Pat. No. 5,889,006, which is a continuation-in-part of application No. 08/602,403, Feb. 16, 1996, Pat. No. 5,883,096, which is a continuation-in-part of application No. 08/457,712, Jun. 2, 1995, abandoned, which is a continuation-in-part of application No. 08/392,697, Feb. 23, 1995, abandoned.

[51] Int. Cl.[7] .................. A61K 31/445; C07D 401/02
[52] U.S. Cl. .................. 514/316; 546/186; 546/187; 546/188; 546/189
[58] Field of Search .................. 546/186, 187; 546/188, 189; 514/316

[56] References Cited

U.S. PATENT DOCUMENTS

| | | | |
|---|---|---|---|
| 2,792,398 | 5/1957 | Kyrides | 514/250 |
| 2,819,273 | 1/1958 | Drain et al. | 514/250 |
| 3,772,298 | 11/1973 | Bartman et al. | 544/399 |
| 3,852,455 | 12/1974 | Carr | 514/250 |
| 3,988,456 | 10/1976 | Nishimura et al. | 514/255 |
| 4,066,070 | 1/1978 | Sukai et al. | 542/470 |
| 4,251,655 | 2/1981 | Scott et al. | 514/250 |
| 4,525,358 | 6/1985 | Balter et al. | 514/255 |
| 4,757,074 | 7/1988 | Coker et al. | 514/255 |
| 4,895,841 | 1/1990 | Sugimoto et al. | 514/212 |
| 5,010,078 | 4/1991 | Abou-Gharbia et al. | 514/319 |
| 5,100,901 | 3/1992 | Sugimoto et al. | 514/319 |
| 5,318,967 | 6/1994 | Bruderer et al. | 514/323.8 |
| 5,700,801 | 12/1997 | Pieper et al. | 514/252 |
| 5,837,707 | 11/1998 | Perregaard et al. | 514/255 |
| 5,900,422 | 5/1999 | Ali | 514/316 |

FOREIGN PATENT DOCUMENTS

| | | |
|---|---|---|
| 565570 | 7/1960 | Belgium . |
| 0 229 391 | 7/1987 | European Pat. Off. ...... C07D 211/26 |
| 284359 | 9/1988 | European Pat. Off. . |
| 0 296 560 | 12/1988 | European Pat. Off. ...... C07D 211/26 |
| 346791 | 12/1989 | European Pat. Off. . |
| 585500 | 3/1994 | European Pat. Off. . |
| 711763 | 5/1996 | European Pat. Off. . |
| M6539 | 12/1968 | France . |
| 963424 | 11/1956 | Germany . |
| 1011427 | 7/1957 | Germany . |
| 2912026 | 10/1979 | Germany . |
| 49-061165 | 6/1974 | Japan . |
| 4-202185 | 7/1992 | Japan ........................ C07D 241/04 |
| 807835 | 1/1959 | United Kingdom . |
| 840358 | 7/1960 | United Kingdom . |
| WO 91/10647 | 7/1991 | WIPO . |
| WO 91/10650 | 7/1991 | WIPO ......................... C07D 211/22 |
| WO 91/10651 | 7/1991 | WIPO ......................... C07D 211/22 |
| WO 93/00906 | 1/1993 | WIPO . |
| WO 93/13083 | 7/1993 | WIPO . |
| WO 95/04050 | 2/1995 | WIPO . |
| 96/19221 | 6/1996 | WIPO . |
| 96/19223 | 6/1996 | WIPO . |
| 96/20173 | 7/1996 | WIPO . |
| 97/24350 | 7/1997 | WIPO . |

OTHER PUBLICATIONS

Jeidrich et al. "Pharmacotheraphy of alzheimer dementia: therapy of cognitive . . . " MEDLINE 97247715, 1997.

Chopin et al. "Effects of four non-cholinergic cognitive enhancers . . . " BIOSIS 93057018, 1992.

Baumgold, et al., European Journal of Pharmacology 251 (1994) 315–317.

Melchiorre, et al., J. Med. Chem, 1993, 36 3734–3737.

Doods, et al., Life Sciences, vol. 52, pp. 497–503 (1993).

(List continued on next page.)

*Primary Examiner*—Ceila Chang
*Attorney, Agent, or Firm*—Anita W. Magatti

[57] ABSTRACT

Di-N-substituted piperazine or 1,4 di-substituted piperadine compounds in accordance with formula I (including all isomers, salts, esters, and solvates)

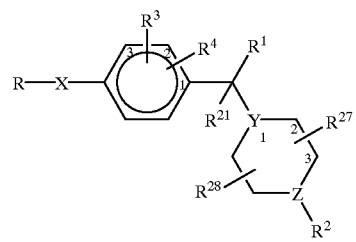

wherein R, $R^1$, $R^2$, $R^3$, $R^4$, $R^{21}$, $R^{27}$, $R^{28}$, X, Y, and Z are as defined herein are muscarinic antagonists useful for treating cognitive disorders such as Alzheimer's disease. Pharmaceutical compositions and methods of preparation are also disclosed. Also disclosed are synergistic combinations of compounds of the above formula with acetylcholinesterase inhibitors.

16 Claims, No Drawings

OTHER PUBLICATIONS

Eberlien, et al., Trends in Pharmacol Sci Dec. 1989 p 50–54.
Borroni, et al., Biochem Soc, Trans, Aug. 1994, 22(3) p. 755–758.
Logemann, et al., Brit. J. Pharmacol (1961) 17, 286–296.
Wilkerson et al, *J. Med. Chem.*, 36 (20) (1993), p. 2899–2907.
Vidaluc et al, *J. Med. Chem.*, 37 (5) (1994), p. 689–698.
Drukarch et al, *Eur. J. Pharmacol.*, 141 (1–2) (1987), p. 153–157.
Provan et al, *Brit. J. Pharmacol.*, 111 (4) (1994), p. 1103–1110.
Cheng et al, *Biochem. Pharmacol.*, 22 (1973), p. 3099–3108.
Watson et al, *J. Pharmacol. Exp. Ther.*, 237 (1986), p. 411–418.

*Chemical Abstracts*, 49, 1 (1955), abstract 322b.
*Chemical Abstracts*, 70, 21 (1969), abstract 96754t.
Dankwardt et al, *Tet. Let.*, 36, 28 (1995), p. 4923–4926.
Protiva et al, *Collect. Czech. Chem. Commun.*, 40, 12 (1975), p. 3904–3923.
*Chemical Abstracts*, 53, abstract 20096f (1959).
*Chemical Abstracts*, 53, abstracts 12306f and 12307d (1959).
*Chemical Abstracts*, 53, abstract 9254b (1959).
*Chemical Abstracts*, 53, abstract 8172b (1959).
*Chemical Abstracts*, 81, abstract 136178 (1972).
*Chemical Abstracts*, vol. 45, No. 12 (1951) 5153, Ochiai et al, "Electrolytic reduction of the pyridinium ion."

MUSCARINIC ANTAGONISTS

CROSS REFERENCE TO RELATED APPLICATIONS

This application is a divisional of U.S. Ser. No. 08/700,628, filed Aug. 8, 1996, now U.S. Pat. No. 5,889,006, which is a continuation-in-part of U.S. Ser. No. 08/602,403, filed Feb. 16, 1996, now U.S. Pat. No. 5,883,096, which is a continuation-in part of U.S. Ser. No. 08/457,712, filed Jun. 2, 1995, abandoned, which is a continuation-in part of U.S. Ser. No. 08/392,697, filed Feb. 23, 1995, abandoned.

BACKGROUND OF THE INVENTION

The present invention relates to di-N-substituted piperazines and 1,4-di-substituted piperidines useful in the treatment of cognitive disorders, pharmaceutical compositions containing the compounds, methods of treatment using the compounds, and to the use of said compounds in combination with acetylcholinesterase inhibitors.

Alzheimer's disease and other cognitive disorders have received much attention lately, yet treatments for these diseases have not been very successful. According to Melchiorre et al. (J. Med. Chem. (1993), 36, 3734–3737), compounds that selectively antagonize M2 muscarinic receptors, especially in relation to M1 muscarinic receptors, should possess activity against cognitive disorders. Baumgold et al. (Eur. J. of Pharmacol., 251, (1994) 315–317) disclose 3-α-chloroimperialine as a highly selective m2 muscarinic antagonist.

The present invention is predicated on the discovery of a class of di-N-substituted piperazines and 1,4-di-substituted piperidines, some of which have m2 selectivity even higher than that of 3-α-chloroimperialine. Logemann et al (Brit. J. Pharmacol. (1961), 17, 286–296) describe certain di-N-substituted piperazines, but these are different from the inventive compounds of the present invention. Furthermore, the compounds of Logemann et al. are not disclosed to have activity against cognitive disorders.

SUMMARY OF THE INVENTION

The present invention relates to compounds according to the structural formula I,

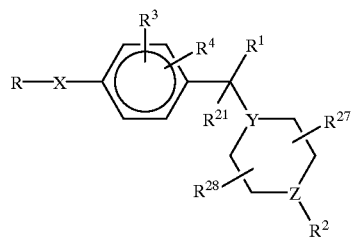

I including all isomers and pharmaceutically acceptable salts, esters, and solvates thereof, wherein one of Y and Z is N and the other is N, CH, or C-alkyl;

X is —O—, —S—, —SO—, —$SO_2$—, —$NR^6$—, —CO—, —$CH_2$—, —CS—, —$C(OR^5)_2$—, —$C(SR^5)_2$—, —$CONR^{20}$—, —$C(alkyl)_2$—, —C(H)(alkyl)—, —$NR^{20}$—$SO_2$—, —$NR^{20}CO$—,

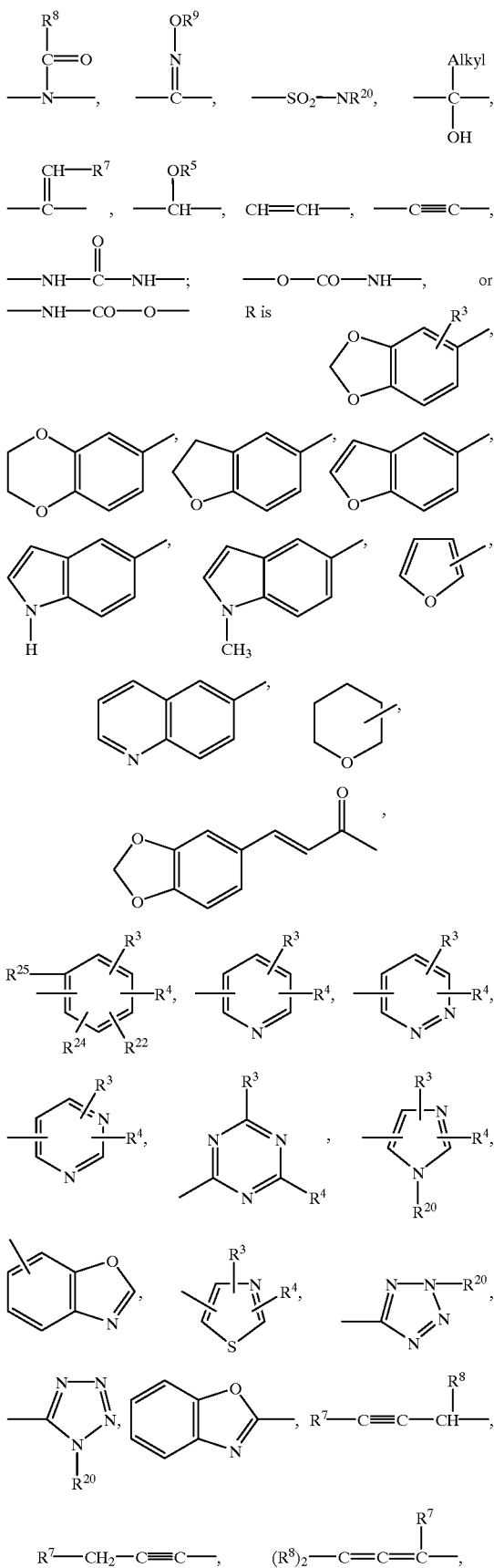

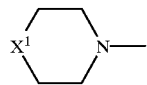

wherein $X^1$ is —CH$_2$—, —O—, or —NR$^7$—),

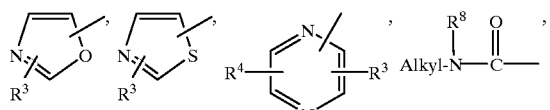

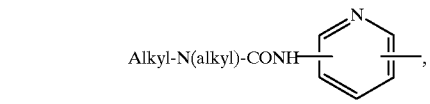

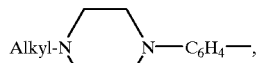    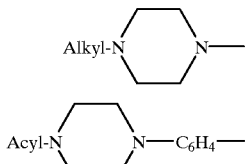

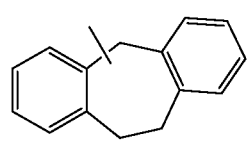

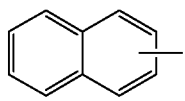

hydrogen, acyl, alkyl, alkenyl, cycloalkyl, cycloalkyl substituted with up to two alkyl groups, cycloalkenyl, bicycloalkyl, arylalkenyl, benzyl, benzyl substituted with up to three independently selected R$^3$ groups, cycloalkylalkyl, polyhaloacyl, benzyloxyalkyl, hydroxyC$_2$–C$_{20}$alkyl, alkenylcarbonyl, alkylarylsulfonyl, alkoxycarbonylaminoacyl, alkylsulfonyl, or arylsulfonyl, additionally, when X is —CH$_2$—, R may also be —OH; in further addition, when X is not N, R may also be hydroxymethyl, in further addition, R and X may combine to form the group Prot-(NOAA)$_r$—NH— wherein r is an integer of 1 to 4, Prot is a nitrogen protecting group and when r is 1, NOAA is a naturally occuring amino acid or an enantiomer thereof, or when r is 2 to 4, each NOAA is a peptide of an independently selected naturally occuring amino acid or an enantiomer thereof;

R$^1$ and R$^{21}$ are independently selected from the group consisting of H, alkyl, alkenyl, cycloalkyl, cycloalkenyl, bicycloalkyl, alkynyl, cyano, aminoalkyl, alkoxycarbonyl, aminocarbonyl, hydroxyamidino, alkoxycarbonylalkyl, phenyl alkyl, alkylcarbonlyoxyalkyl,

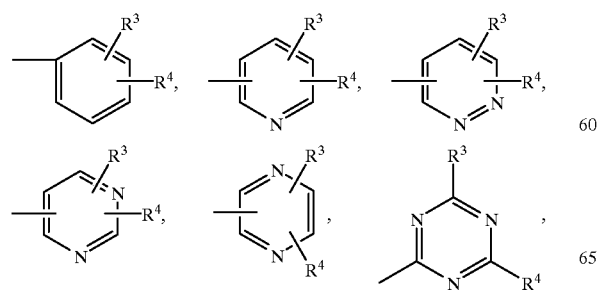

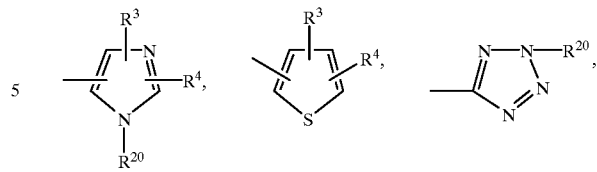

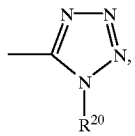 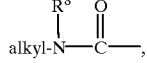 

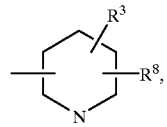

H, —OH, (provided R$^1$ and R$^{21}$ are both not —OH and Y is not N), formyl, —CO alkyl, —COacyl, —COaryl, and hydroxyalkyl; additionally R$^1$ and R$^{21}$ together may form the group

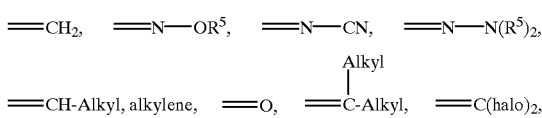

in further addition, R$^1$ and R$^{21}$ together with the carbon atom to

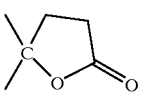   or   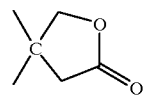

which they are attached may form the group or R$^1$ and R$^{21}$ together with the carbon atom to which they are attached may form a saturated heterocyclic ring containing 3 to 7 carbon atoms, one or more of which may be optionally substituted by alkyl, and one or two groups independently selected from S, O, and N—R$^{20}$; R$^2$ is

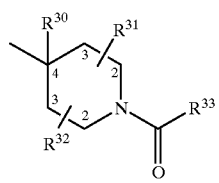   or   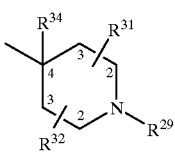

R$^3$, R$^4$, R$^{22}$, R$^{24}$, and R$^{25}$ are independently selected from the group consisting of alkyl, H, halo, alkoxy, benzyloxy, benzyloxy substituted by nitro or aminoalkyl, haloalkyl, polyhaloalkyl, nitro, cyano, sulfonyl, hydroxy, amino, alkylamino, formyl, alkylthio, polyhaloalkoxy, acyloxy, trialkylsilyl, alkylsulfonyl, arylsulfonyl, acyl, alkoxycarbonyl alkylsulfinyl; —OCONH$_2$, —OCONH-alkyl, alkylaminoalkyl, dialkylaminoalkyl, —COOH, —CON(R$^{20}$)$_2$, —OCON(alkyl)$_2$, —NHCOO-alkyl, —NHCO-alkyl, phenyl, hydroxyalkyl, or morpholino;

each $R^5$ and $R^6$ is independently selected from the group consisting of H and alkyl, provided that when X is $C(OR^5)_2$ or $C(SR^5)_2$, both $R^5$ groups cannot be H, and in addition, when X is $C(OR^5)_2$ or $C(SR^5)_2$, the two $R^5$ groups in X may be joined to form —$(CR^{20}{}_2)_p$— wherein p is an integer of 2 to 4;

$R^7$ is independently selected from the group consisting of H, alkyl, arylalkyl, cycloalkyl, aryl and aryl substituted with $R^3$ and $R^4$ as defined herein;

each $R^8$ is independently selected from the group consisting of H, hydroxyalkyl, or alkyl or two $R^8$ groups may be joined to form an alkylene group;

$R^9$ is H, alkyl, aralkyl, or acyl:

$R^{20}$ is H, aryl or alkyl;

$R^{27}$ and $R^{28}$ are independently selected from the group consisting of H, alkyl, hydroxyalkyl, arylalkyl, aminoalkyl, haloalkyl, thioalkyl, alkylthioalkyl, carboxyalkyl, imidazolylalkyl, and indolylalkyl, additionally $R^{27}$ and $R^{28}$ may combine to form an alkylene group.:

$R^{29}$ is H, alkyl, —CO-alkyl, alkoxycarbonyl, aminocarbonyl, aryloxycarbonyl alkylaminocarbonyl, dialkylaminocarbonyl, alkylsulfonyl, or arysulfonyl;

$R^{30}$ is H, alkyl, aryl, cycloalkyl, hydroxyalkyl, aminoalkyl, —$COOR^{20}$, —$CON(R^{20})_2$ or cyano;

$R^{31}$ and $R^{32}$ are the same as $R^{30}$ and in addition, two $R^{30}$, $R^{31}$ and $R^{32}$ groups may form the group —$(CH_2)_r$— (wherein r is 1 to 6), in further addition, $R^{31}$ and $R^{32}$ can also be hydroxy, —$N(R^{20})_2$, —O-acyl, —$N(R^{20})$acyl, —$OCOOR^{20}$, or —$OCON(R^{20})_2$;

$R^{33}$ is aryl or heteroaryl, with the proviso that when $R^{33}$ is heteroaryl, the CO—$R^{33}$ bond is to a carbon atom in the $R^{33}$ group: and $R^{34}$ is alkyl, cycloalkyl or aryl and in addition $R^{34}$ may also be H when $R^1$ and $R^{21}$ together with the carbon atom to which they are attached form a saturated heterocyclic ring containing 3 to 7 carbon atoms and two groups independently selected from S, O, and N—$R^{20}$.

In a preferred group of compounds Y and Z are N

In another preferred group of compounds Y is CH and Z is N

In another preferred group of compounds R is

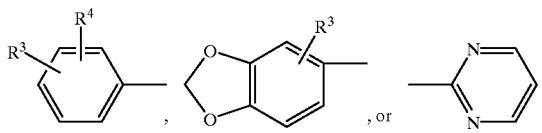

and X is O, SO, $SO_2$, $CH_2$, CH(alkyl), C(alkyl)$_2$, —CH(OH)—, or —$N(R^{20})CO$.

In another preferred group of compounds $R^3$ and $R^4$ are H and either $R^1$ is cycloalkyl, or alkyl, and $R^{21}$ is H or $R^1$ and $R^{21}$ together form =O.

In another preferred group of compounds R is

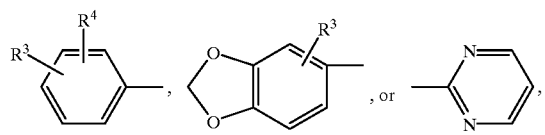

X is O, SO $SO_2$, $CH_2$, CH(alkyl), C(alkyl)$_2$, or —$N(R^{20})$CO; $R^3$ and $R^4$ are H and either $R^1$ is cycloalkyl or alkyl; and $R^{21}$ is H or $R^1$ and $R^{21}$ together form =O or

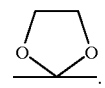

In another preferred group of compounds at least one of $R^{27}$ and $R^{28}$ is alkyl.

In another preferred group of compound one of $R^{27}$ or $R^{28}$ is methyl and the other is hydrogen.

In another preferred group of compounds R is

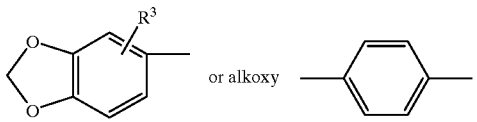

In another preferred group of compounds X is $SO_2$, $CH_2$, or —$N(CH_3)$—CO—.

In another group of preferred compounds, $R^2$ has the formula

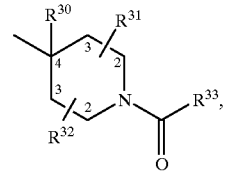

and $R^{30}$ is H or $CH_3$: $R^{31}$ and $R^{32}$ are H: and $R^{33}$ is ortho-substituted aryl or hetroaryl, preferably

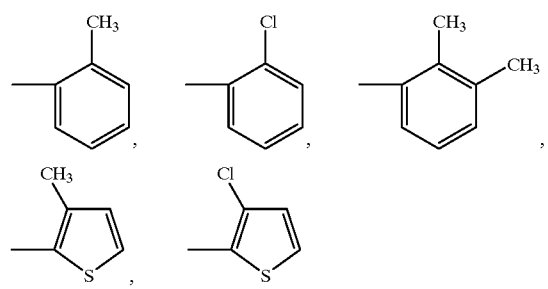

and

In another group of preferred compounds, $R^2$ has the formula

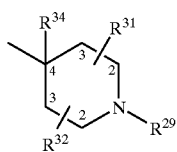

$R^{34}$ is methyl and $R^{31}$ and $R^{32}$ are H.

Preferred specific compounds of this invention are listed in the table of compounds below as compound numbers:

17
18
25
30
31
32
34
35
36
37
41
43
44
49
53
54
56
57
58
59
80
82
84
85
94
98
100
108

More preferred specific compounds of this invention are listed in the table of compounds below as compound numbers:

17
18
25
31
41
44
82
84
94
100

Of these the most preferred compounds are compound numbers 82 and 94.

Another aspect of the invention is a pharmaceutical composition which comprises a compound having structural formula I as defined above in combination with a pharmaceutically acceptable carrier.

Another aspect of the invention is the use of a compound formula I for the preparation of a pharmaceutical composition useful in the treatment of cognitive disorders and neurodegenerative diseases such as Alzheimer's disease.

Yet another aspect of the invention comprises a method for making a pharmaceutical composition comprising mixing a compound of formula I with a pharmaceutically acceptable carrier.

Another aspect of this invention is a method for treating a cognitive or neurodegenerative disease comprising administering to a patient suffering from said disease an effective amount of a compound of formula I.

Another aspect of this invention is a method for treating a cognitive or neurodegenerative disease comprising administering to a patient suffering from said disease an effective amount of a combination of a compound of formula I with an acetycholinesterase inhibitor.

Another aspect of this invention is a kit comprising in separate containers in a single package pharmaceutical compounds for use in combination to treat cognitive disorders in one container a compound of formula I in a pharmaceutically acceptable carrier and in a second container an acetylcholinesterase inhibitor in a pharmaceutically acceptable carrier, the combined quantities being an effective amount.

DETAILED DESCRIPTION

Except where stated otherwise the following definitions apply throughout the present specification and claims. These definitions apply regardless of whether a term is used by itself or in combination with other terms. Hence the definition of "alkyl" applies to "alkyl" as well as the "alkyl" portions of "alkoxy", "haloalkyl", etc.

Alkyl represents a straight or branched saturated hydrocarbon chain having 1 to 20 carbon atoms, more preferably 1 to 8 carbon atoms.

Alkenyl represents a straight or branched hydrocarbon chain of from 2 to 15 carbon atoms, more preferably 2 to 12 carbon atoms, having at least one carbon-to-carbon double bond.

Alkynyl represents a straight or branched hydrocarbon chain of from 2 to 10 carbon atoms, more preferably 2 to 8 carbon atoms, having at least one carbon-to-carbon triple bond.

Cycloalkyl represents a saturated carbocyclic ring having 3 to 12 carbon atoms.

Cycloalkenyl represents a carbocyclic ring having from 5 to 8 carbon atoms and at least one carbon-to-carbon double bond in the ring.

Bicycloalkyl represents a saturated bridged carbocyclic ring having 5 to 12 carbon atoms.

Acyl represents a radical of a carboxylic acid having the formula alkyl-CO—, aryl-CO—, aralkyl-CO—, cycloalkyl-CO—, alkylcycloalkyl-CO—, and heteroaryl-CO—.

Halo represents fluoro, chloro, bromo or iodo.

Aryl represents phenyl or naphthyl optionally substituted with 1 to 5 $R^3$ groups.

Heteroaryl represents a cyclic group of 5 or 6 atoms, or a bicyclic group of 9 or 10 atoms, at least one of which is carbon and having at least one O, S, or N atom interrupting a carbocyclic ring having a sufficient number of pi electrons to provide aromatic character. Carbon atoms may optionally be substitiuted by $R^3$ groups. Nitrogen atoms may optionally be substituted —$R^{20}$ or —$COR^{20}$ groups. Preferred heteroaromatic groups are pyridyl, furanyl, benzofuranyl, thienyl, benzothienyl, thiazolyl, thiadiazolyl, imidazolyl, pyrimidinyl, pyrazinyl, pyridazinyl, 1,3,5-triazinyl, and indolyl.

Polyhalo represents substitution of at least 2 halo atoms to the group modified by the term "polyhalo".

Hydroxyamidino represents a group having the formula

Azabicyclo represents a saturated bridged ring containing from 4 to 8 carbon atoms and at least one nitrogen atom.

Sulfonyl represents a group of the formula —$SO_2$—.

Sulfinyl represents a group of the formula —SO—.

Alkylene represents a group having the formula —$(CH_2)_q$—, wherein q is an integer of from 1 to 20.

Naturally occurring amino acid (NOAA) means an acid selected from the group consisting of alanine(ala), arginine (arg), asparagine (asn), aspartic acid (asp), cysteine (cys), glutamine (gln), glutamic acid (glu), glycine (gly), histadine (his), isoleucine (ile), leucine (leu), lysine (lys), methionine (met), phenylalanine (phe), proline (pro), serine (ser), threonine (thr), tryptophan (trp), tyrosine (tyr), and valine (val).

Nitrogen protecting group (Prot) means a group capable of protecting a nitrogen on a naturally occurring amino acid (or an enantiomer thereof) from reaction. Preferred nitrogen protecting groups are carbobenzyloxy (CBZ), $CH_3OCO(CH_2)_9CO$, and t-butoxycarbonyl (BOC). Of course any operable nitrogen protecting group is included.

When a variable appears more than once in the structural formula, for example $R^5$ when X is —$C(OR^5)_2$—, the identity of each variable appearing more than once may be independently selected from the definition for that variable.

Compounds of this invention may exist in at least two stereo configurations based on the asymmetric carbon to which $R^1$ is attached, provided that $R^1$ and $R^{21}$ are not identical. Further stereoisomerism is present when X is SO, or $C(OR^5)_2$ (when the two $R^5$ groups are not the same) or when $R^{27}$ or $R^{28}$ is not hydrogen. Also within formula I there are numerous other possibilities for stereoisomerism. All possible stereoisomers of formula I are within the scope of the invention.

Compound of formula I can exist in unsolvated as well as solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

Compound in accordance with formula I may be produced by processes known to those skilled in the art as shown by the following reaction steps:

General Description of Methods

Compounds wherein $R^2$ has the formula

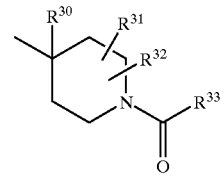

can be made as shown in scheme I.

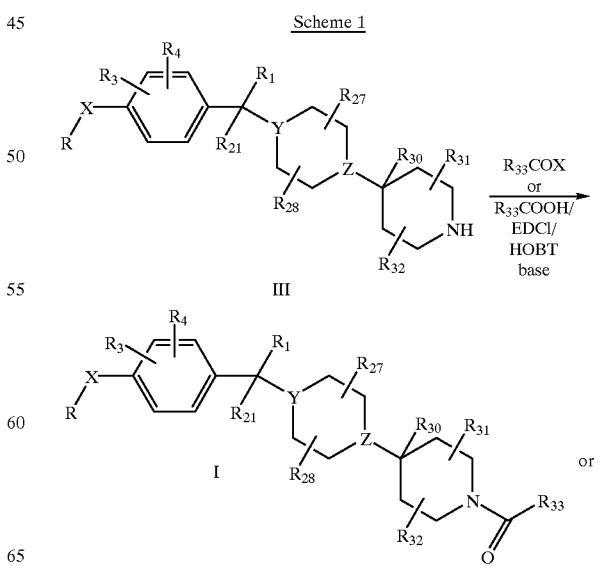

For compounds wherein $R^2$ has the formula

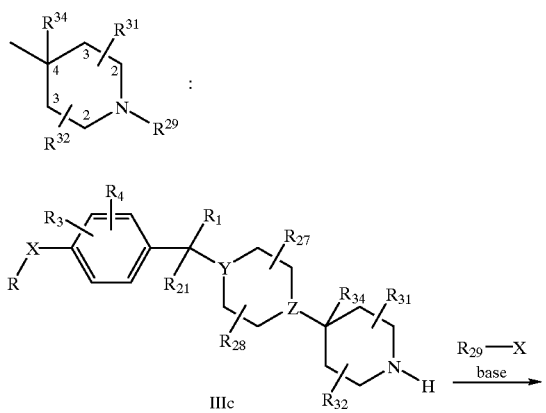

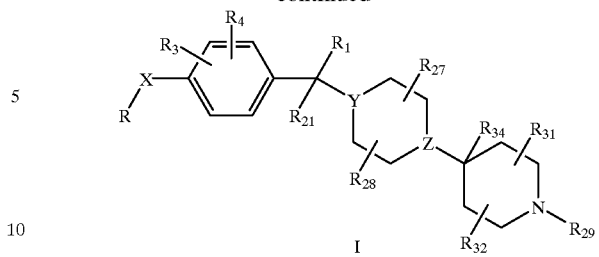

Intermediate III is treated with a suitably activated carboxylic acid derivative, $R_{33}CO—X$, where X is a leaving group such as halogen or $OCOCH_3$. Alternatively, a mixture of compound III and $R_{33}COOH$ can be treated with N-hydroxybenzotriazole and a carbodiimide such as N-ethyl-N-(3-dimethylaminopropyl)-carbodiimide hydrochloride or dicyclohexylcarbodiimide in the presence of a base such as triethylamine and a solvent such as DMF to give I. Alternatively, intermediate IIIc is treated with a group $R_{29}$—X, where X and $R_{20}$ are as previously defined (except $R_{29} \neq H$), in the presence of a base such as triethylamine.

Intermediates III can be made via a variety of methods. When $X=CH_2$ or CO, III can be made as shown in scheme 2:

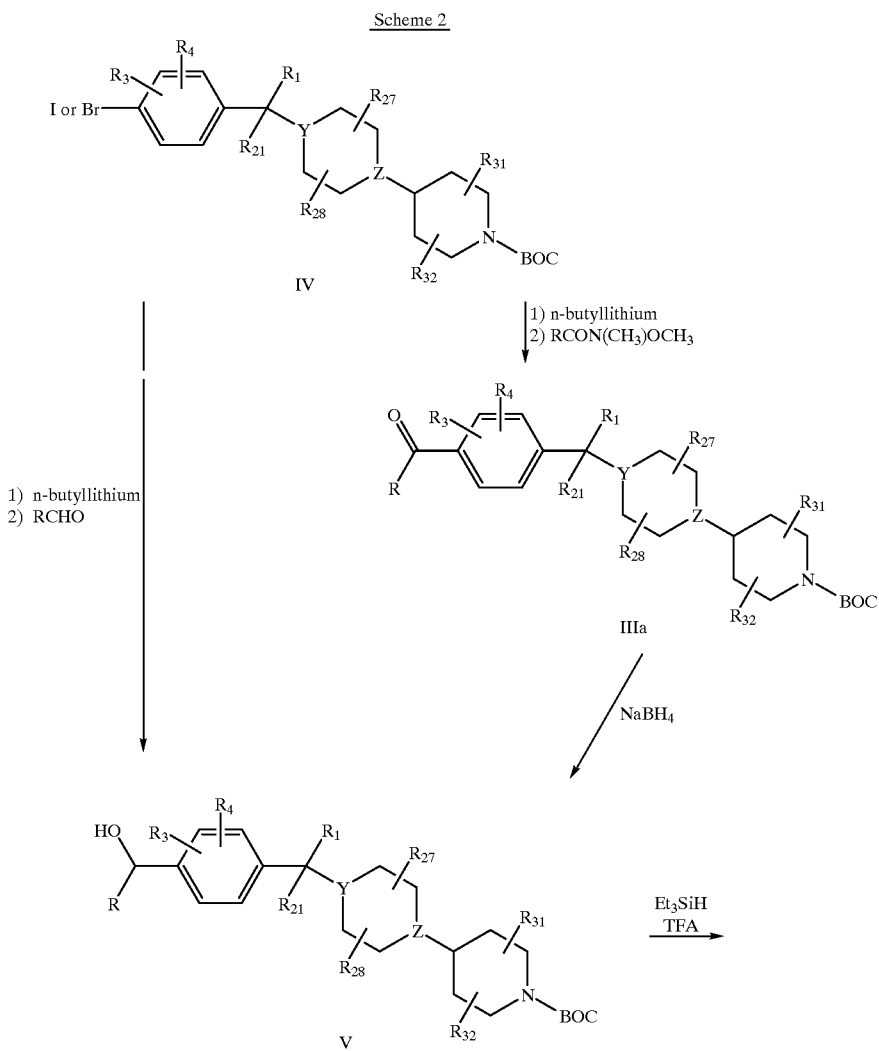

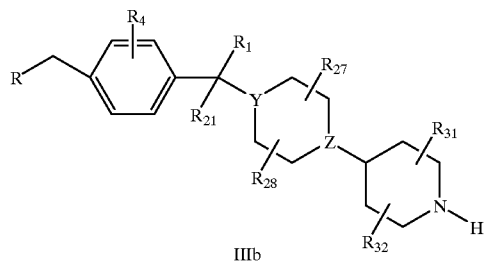

IIIb

Aryl halide IV is treated with an alkyllithium such as n-butyllithium or t-butyllithium followed by reaction with an RCON(CH$_3$)OCH$_3$ to give compound IIIa, which can be deprotected and converted to I as shown above. Additionally, IIIa can be reduced to the alcohol V with a suitable reducing agent such as sodium borohydride. Compound V can also be made by treatment of IV with an alkyllithium as previously described followed by reaction with RCHO. Compound V is converted to compounds IIIb by treating V with a reducing agent such as triethylsilane in the presence of a strong acid such as trifluoroacetic acid.

Compounds of formula Ia, Ib, and Ic can be prepared via a related sequence as shown in Scheme 3:

Scheme 3:

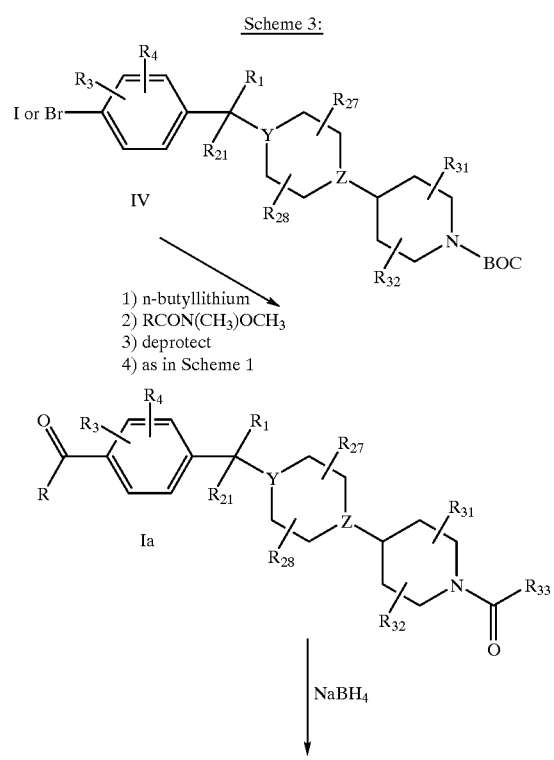

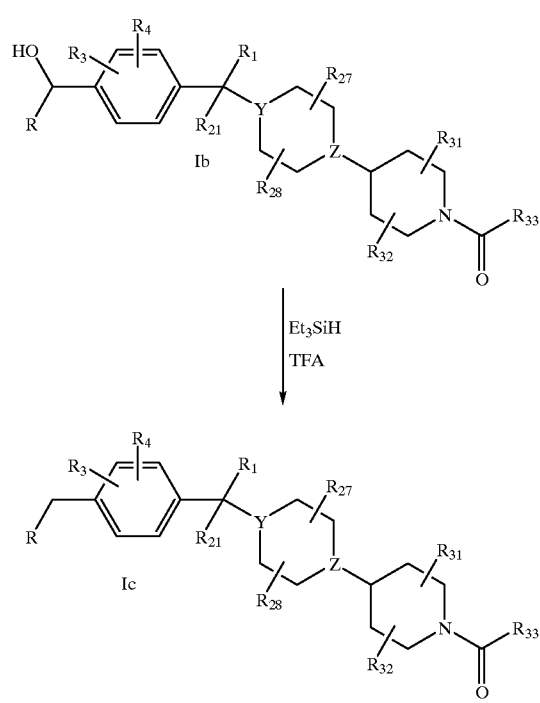

Intermediate IIIa is prepared as shown in Scheme 2, deprotected and then converted to Ia using methods of Scheme 1. This can then be converted to Ib and Ic using methods of Scheme 2.

Other compounds of this invention can be prepared by methods similar to those described in Schemes 2–3 wherein the aryl lithium reagent derived from IV is reacted with various electrophiles. For instance, compounds where X is NHCO or N(alkyl)CO can be prepared as shown in Scheme 4:

Scheme 4

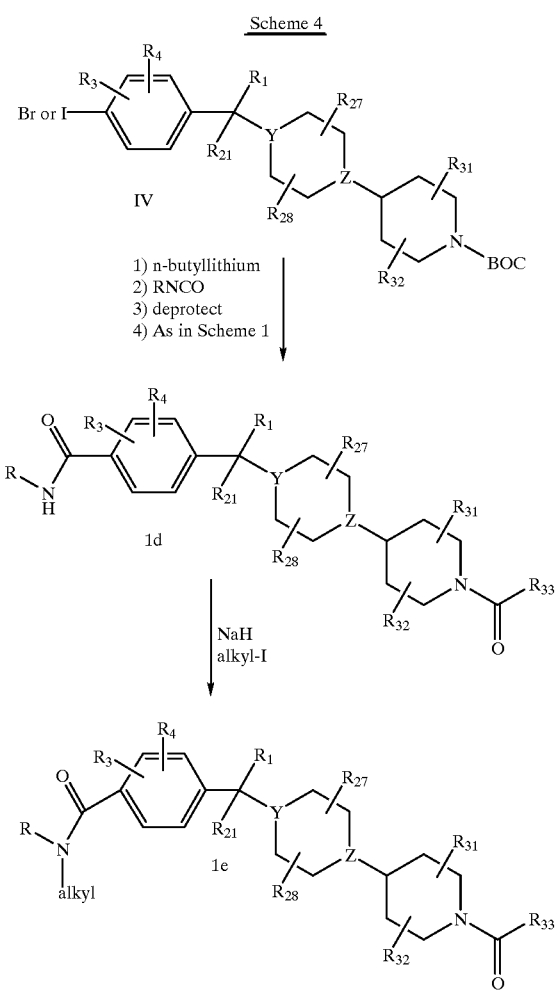

Intermediate IV is reacted with an alkyllithium as previously described followed by addition of an isocyanate RNCO. The intermediate is deprotected and converted to compounds of type 1d as described in Scheme 1. Compounds of type 1d are converted to compounds 1e by reacting with an alkyliodide such as methyliodide in the presence of a suitable base such as sodium hydride.

Intermediate IV can be prepared via one of the following procedures:

Scheme 5

Intermediate IVa:

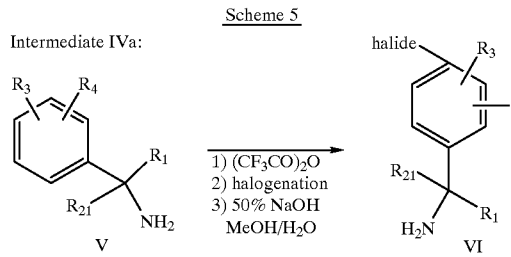

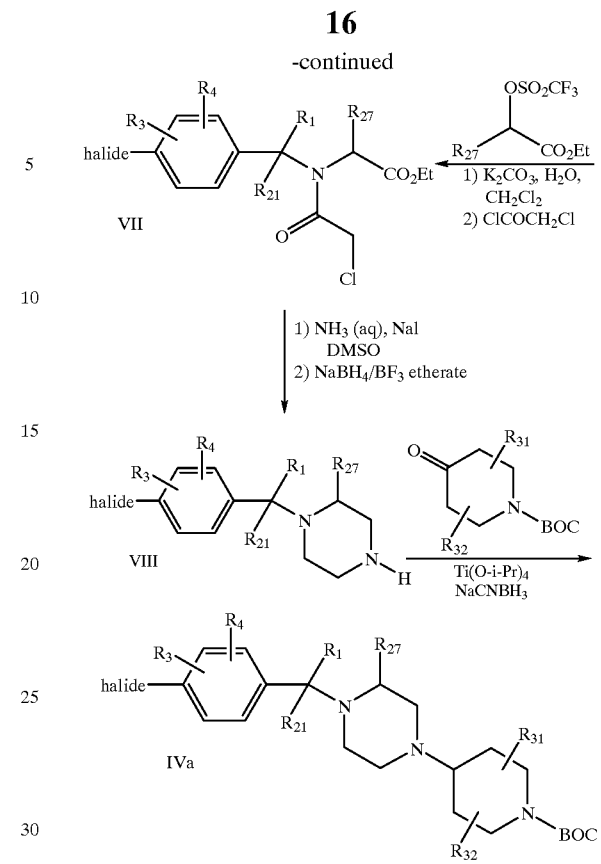

Benzylamine V is protected as its trifluoroacetamide, treated with a halogenating agent such as bromine, dibromodimethylhydantoin, or bis(trifluoroacetoxy) iodobenzene, and deprotected with aqueous base to give VI. This is treated with a carboxylic ester derivative containing a leaving group such as trifluoromethanesulfonate in the 2-position followed by chloroacetyl chloride to give VII. Treatment of VII with ammonia followed by reduction with NaBH$_4$/BF$_3$ etherate gives VIII. Treatment of VIII with an N-BOC 4-piperidinone derivative preferable in the presence of a Lewis acid such as titanium tetraisopropoxide followed by a reducing agent such as sodium cyanoborohydride affords IVa.

Scheme 6

Intermediate IVb:

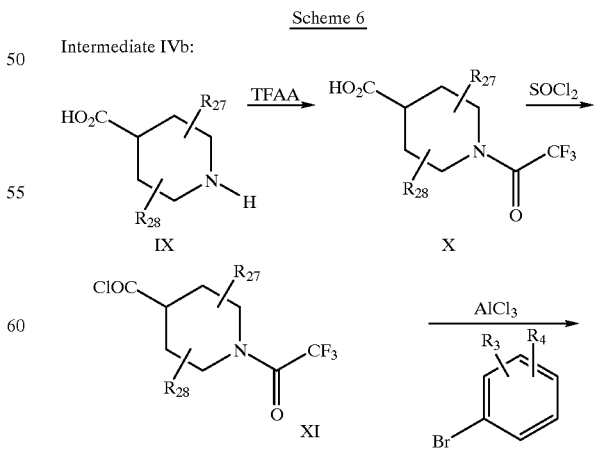

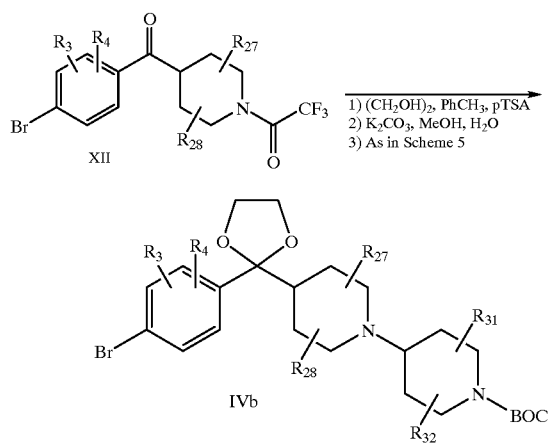

A piperidine 4-carboxylic acid derivative IX is protected on nitrogen using trifluoroacetic anhydride and converted to the corresponding acid chloride XI using thionyl chloride. Intermediate XI is reacted with an arylhalide in the presence of a Lewis acid such as aluminum chloride to give XII. The carbonyl group of XII is protected by treatment with ethylene glycol in the presence of a strong acid such a toluenesulfonic acid. The nitrogen is deprotected using aqueous alcoholic base, and the resulting compound treated with an N-BOC 4-piperidinone derivative as described in Scheme 5 to afford IVb.

Compounds of formula If (where $R_{30} \neq H$) and II are prepared as shown in Scheme 7:

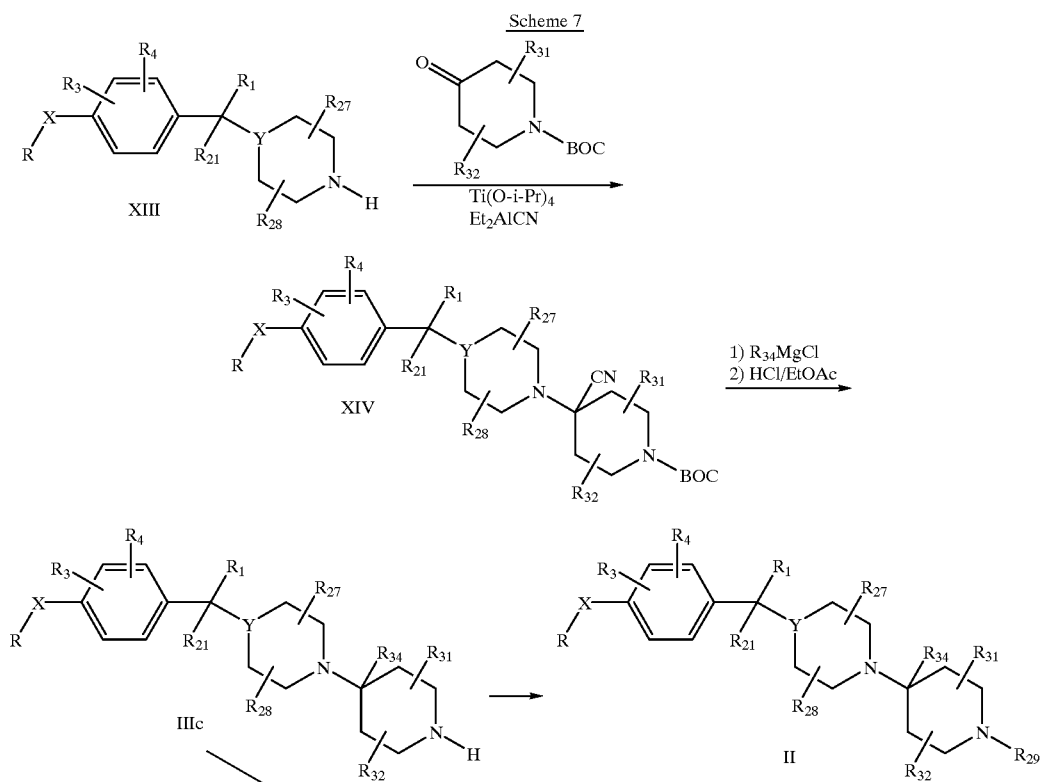

-continued

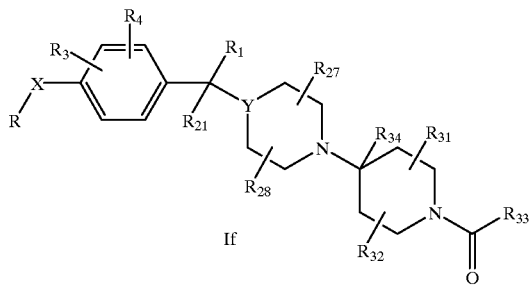

If

Intermediate XIII is treated with an N-BOC 4-piperidinone derivative preferably in the presence of a Lewis acid such as titanium tetraisopropxide followed by treatment with diethylaluminum cyanide to give XIV. This is treated with Grignard reagent $R_{34}MgCl$ followed by hydrolysis with aqueous acid to give IIIc. Compound IIIc can be converted to compounds of type If and II using the method shown in Scheme 1.

In addition to methods described above, compounds of formula Ig (where A is O, S or N—$R^20$) can be prepared as described in Scheme 8.

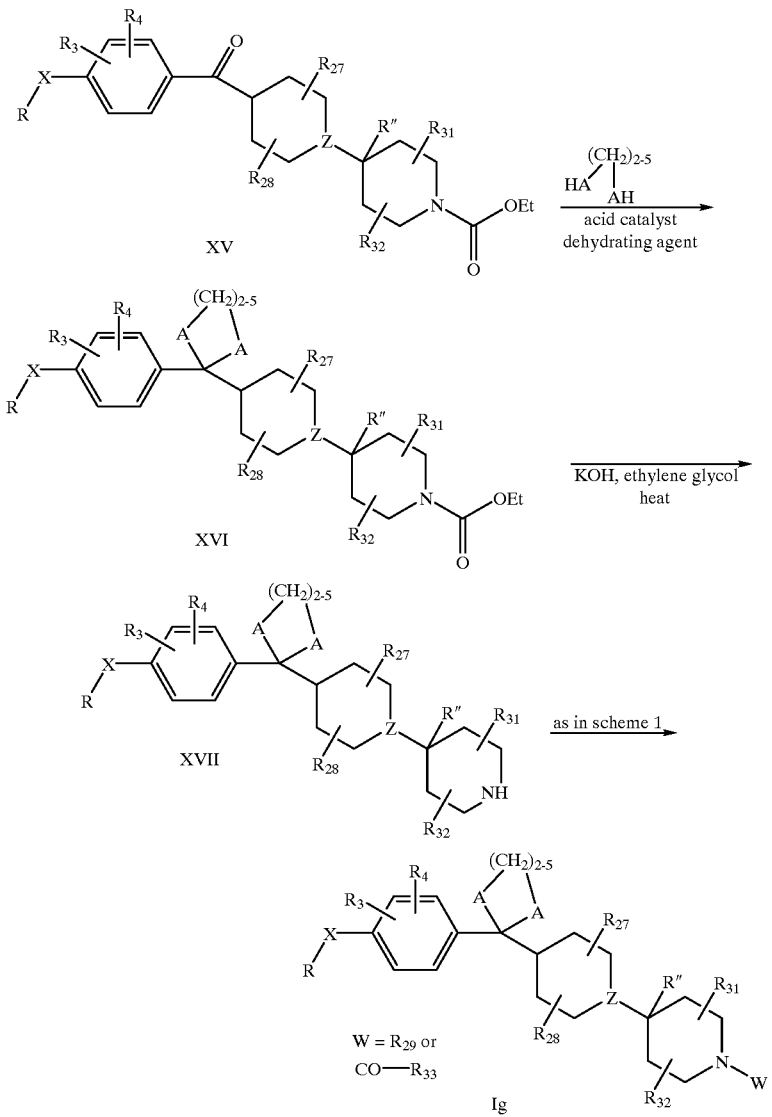

In the compound HA—(CH$_2$)$_{2-5}$—AH, each A is independently O, S, or N—R$_{20}$, and each CH$_2$ group may optionally be substituted by one or more alkyl groups. Examples of the compound HA—(CH$_2$)$_{2-5}$—AH, include

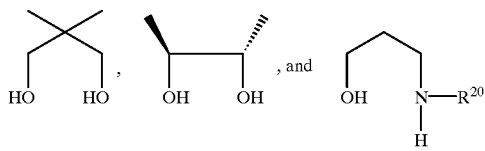

Compound XV (where R" is either R$_{30}$ or R$_{34}$) is prepared as described in schemes 7 and 10. This is treated with HA—(CH$_2$)$_{2-5}$—AH optionally in the presence of an acid catalyst and a dehydrating agent. When A is O, the acid catalyst is preferably an organic protic acid such as toluenesulfonic acid and the dehydrating agent is triethyl orthoformate. When A is S, a Lewis acid such as boron trifluoride etherate serves as both acid catalyst and dehydrating agent. The resulting product XVI is hydrolyzed with a strong base such as potassium hydroxide to give XVII. This is converted to to Ie via methods described in scheme 1.

When X=S, SO, or SO$_2$, intermediates III are prepared as shown in the following schemes:

Scheme 9

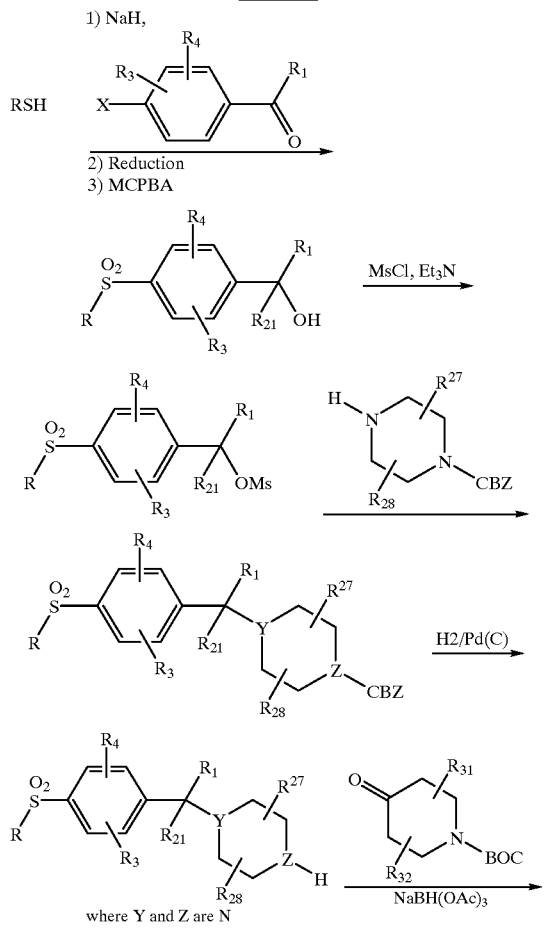

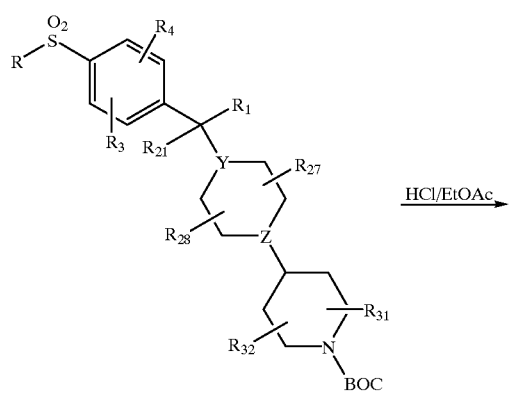

Scheme 10

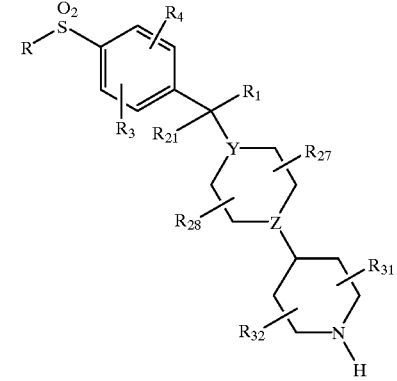

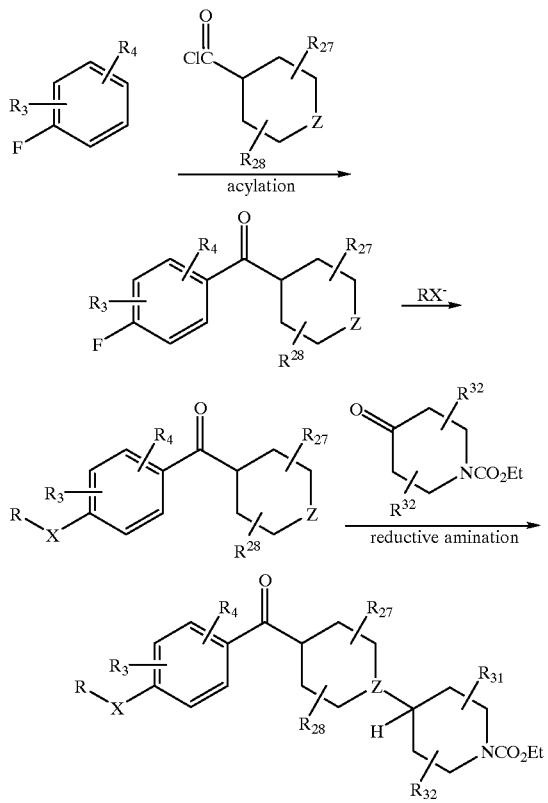

The above reactions may be followed if necessary or desired by one or more of the following steps; (a) removing any protective groups from the compound so produced; (b) converting the compound so-produced to a pharmaceutically acceptable salt, ester and/or solvate; (c) converting a compound in accordance with formula I so produced to another compound in accordance with formula I, and (d) isolating a compound of formula I, including separating stereoisomers of formula I.

Based on the foregoing reaction sequence, those skilled in the art will be able to select starting materials needed to produce any compound in accordance with formula I.

In the above processes it is sometimes desirable and/or necessary to protect certain groups during the reactions. Conventional protecting groups, familiar to those skilled in the art, are operable. After the reaction or reactions, the protecting groups may be removed by standard procedures.

The compounds of formula I exhibit selective m2 and/or m4 muscarinic antagonizing activity, which has been correlated with pharmaceutical activity for treating cognitive disorders such as Alzheimers disease and senile dementia.

The compounds of formula I display pharmacological activity in test procedures designated to indicate m1 and m2 muscarinic antagonist activity. The compounds are non-toxic at pharmaceutically therapeutic doses. Following are descriptions of the test procedures.

Muscarinic Binding Activity

The compound of interest is tested for its ability to inhibit binding to the cloned human m1, m2, m3, and m4 muscarinic receptor subtypes. The sources of receptors in these studies were membranes from stably transfected CHO cell lines which were expressing each of the receptor subtypes. Following growth, the cells were pelleted and subsequently homogenized using a Polytron in 50 volumes cold 10 mM Na/K phosphate buffer, pH 7.4 (Buffer B). The homgenates were centrifuged at 40,000×g for 20 minutes at 4° C. The resulting supernatants were discarded and the pellets were resuspended in Buffer B at a final concentration of 20 mg wet tissue/ml. These membranes were stored at −80° C. until utilized in the binding assays described below.

Binding to the cloned human muscarinic receptors was performed using $^3$H-quinuclidinyl benzilate (QNB) (Watson et al., 1986). Briefly, membranes (approximately 8, 20, and 14 $\mu$g of protein assay for the m1, m2, and m4 containing membranes, respectively) were incubated with $^3$H-QNB (final concentration of 100–200 pM) and increasing concentrations of unlabeled drug in a final volume of 2 ml at 25° C. for 90 minutes. Non-specific binding was assayed in the presence of 1 $\mu$M atropine. The incubations were terminated by vacuum filtration over GF/B glass fiber filters using a Skatron filtration apparatus and the filters were washed with cold 10 mM Na/K phosphate butter, pH 7.4. Scintillation cocktail was added to the filters and the vials were incubated overnight. The bound radioligand was quantified in a liquid scintillation counter (50% efficiency). The resulting data were analyzed for $IC_{50}$ values (i.e. the concentration of compound required to inhibit binding by 50%) using the EBDA computer program (McPherson, 1985). Affinity values ($K_i$) were then determined using the following formula (Cheng and Prusoff, 1973);

$$K_i = \frac{IC_{50}}{1 + \left[\frac{\text{concentration of radioligand}}{\text{affinity } (K_D) \text{ of radioligand}}\right]}$$

Hence a lower value of $K_i$ indicates greater binding affinity.

The following publications, the entire contents of which are incorporated herein by reference, explain the procedure in more detail.

Cheng, Y.-C. and Prusoff, W. H., Relationship between the inhibitory constant ($K_i$) and the concentration of inhibitor which causes 50 per cent inhibition ($IC_{50}$) of an enzymatic reaction. Biochem. Pharmacol. 22: 3099–3108, 1973.

McPherson, G. A. Kinetic, EBDA, Ligand, Lowry: A Collection of Radioligand Binding Analysis Programs. Elsevier Science Publishers BV, Amsterdam, 1985.

Watson, M. J, Roeske, W. R. and Yamamura, H. I. [$^3$H] Pirenzepine and (−)[$^3$H] quinuclidinyl benzilate binding to rat cerebral cortical and cardiac muscarinic cholinergic sites. Characterization and regulation of antagonist binding to putative muscarinic subtypes. J. Pharmacol. Exp. Ther. 237: 411–418, 1986.

To determine the degree of selectivity of a compound for binding the m2 receptor, the $K_i$ value for m1 receptors was divided by the $K_i$ value for m2 receptors. A higher ratio indicates a greater selectivity for binding the m2 muscarinic receptor.

| RESULTS OF THE TESTS Ki (nM) | | | |
|---|---|---|---|
| Compound No. | m1 | m2 | m4 |
| 17 | 47.33 | 0.14 | 2.26 |
| 18 | 48.37 | 0.11 | 0.77 |
| 25 | 337.68 | 0.55 | 6.51 |
| 31 | 308.95 | 0.63 | 12.10 |
| 41 | 29.9 | 0.06 | 1.47 |
| 44 | 36.79 | 0.11 | 0.76 |
| 82 | 337.52 | 0.10 | 6.33 |
| 84 | 12.32 | 0.04 | 0.06 |
| 94 | 28.99 | 0.02 | 0.76 |
| 100 | 6497 | 0.12 | 3.38 |

For the compounds appearing in TABLE OF COMPOUNDS the following range of muscarinic antagonistic activity was observed
  m2: 0.02 nM to 106.0 nM
  m1: 0.65 nM to 1052.3 nM
  m4: 0.02 nM to 110.8 nM For preparing pharmaceutical compositions from the compounds of formula I, compounds capable of enhancing ACh release, and ACh'ase inhibitors, pharmaceutically acceptable, inert carriers are admixed with the active compounds. The pharmaceutically acceptable carriers may be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it may also be an encapsulating material.

Liquid form preparations include solutions, suspensions and emulsions. As an example may be mentioned water or water-propylene glycol solutions for parenteral injection.

Also included are solid form preparations which are intended to be converted, shortly before use, to liquid form preparations for either oral or parentertal administration. Such liquid forms include solutions, suspensions and emulsions. These particular solid form preparations are most conveniently provided in unit dose form and as such are used to provide a single liquid dosage unit.

The invention also contemplates alternative delivery systems including, but not necessarily limited to, transdermal delivery. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packeted tablets, capsules and powders in vials or ampules. The unit dosage form can also be a capsule, cachet or tablet itself, or it may be the appropriate number of any of these in a packaged form.

The quantity of active compound in a unit dose preparation may be varied or adjusted from 1 mg to 100 mg according to the particular application and the potency of the active ingredient and the intended treatment. This would correspond to a dose of about 0.001 to about 20 mg/kg which may be divided over 1 to 3 administrations per day. The composition may, if desired, also contain other therapeutic agents.

The dosages may be varied depending on the requirement of the patient, the severity of the condition being treating and the particular compound being employed. Determination of the proper dosage for a particular situation is within the skill of those in the medical art. For convenience, the total daily dosage may be divided and administered in portions throughout the day or by means providing continuous delivery.

When a compound of formula I or a compound capable of enhancing ACh release is used in combination with an acetylcholinesterase inhibitor to treat cognitive disorders these two active components may be co-administered simultaneously or sequentially, or a single pharmaceutical composition comprising a compound of formula I or a compound capable of enhancing ACh release and an acetylcholinesterase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the acetylcholinesterase inhibitor may range from 0.001 to 100 mg/kg body weight.

The invention disclosed herein is exemplified by the following preparation and examples which should not be construed to limit the scope of the disclosure. Alternative mechanistic pathways and analogous structures may be apparent to those skilled in the art.

In the following examples intermediate numerals have normal type and are enclosed by parenthesis, e.g., (5). Product compounds are in bold type and underlined, e.g., <u>5</u>

EXAMPLE 1

Synthesis of Compound No. <u>4</u>

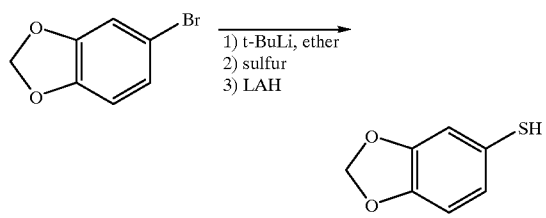

An ether (650 mL) solution of the bromide (15.5 g, 0.07 mol) was cooled in a dry ice acetone bath where t-BuLi (100 mL, 1.7M) was added dropwise. After stirring for 3 h the sulfur powder (4.9 g, 0.15 mol) was added and stirring continued for an additional hour. The temperature was warmed to room temperature and stirring continued for 16 h. After quenching with water, ether was added and the organic phase was washed with 5% HCl, water, 10% sodium carbonate and then brine. The solution was concentrated and purified by chromatography with 5% ethyl acetate/hexane (Rf=0.7/CH$_2$Cl$_2$: hexane 1:1) with 33 g yellow solid collected.

The sample was dissolved in THF (50 mL) and cooled in an ice water bath where it was added to a mixture of LAH (0.91 g, 0.02 mol) and 20 mL THF. Stirring was continued for 10 minutes, then warmed to room temperature and stirred for 1 h. The reaction was diluted with ethyl acetate and quenched with water. 10% HCl was added and the organic layer separated, washed with water and brine. After concentration and drying under vacuum, 6.6 g of a yellow oil was collected.

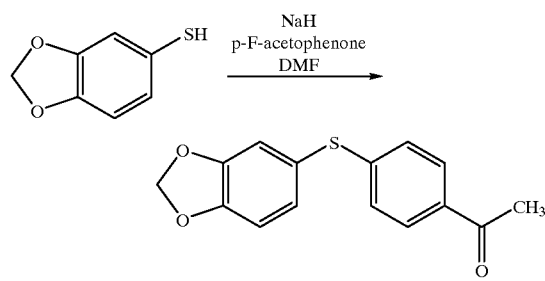

The thiol (19 g, 124 mmol) was dissolved in DMF (180 mL) and cooled in an ice bath where sodium hydride (4.9 g, 60% in oil) was added in portions. Stirring was continued for 1 h, then warmed to room temperature and stirred for an additional 1 h. The 4-fluoroacetophenone (18.7 g, 136 mmol) was added dropwise and then stirred at 70° C. for 3 h. The reaction was concentrated on a rotovap, diluted with ethyl acetate, and washed with water and brine. The solution was evaporated on a rotovap and the residue chromatographed on silica gel (20% ethyl acetate/hexane) to collect 24.5 g(73%) of a pale yellow solid.

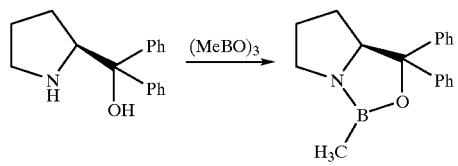

To a solution of the alcohol (10.1 g, 40 mmol) in toluene (100 mL) was slowly added the trimethyl boroxine (3.3 g, 27 mmol). After 4 h the volatiles were removed by distillation (oil bath temp=140–150° C.). Cooling to room temperature was followed by addition of toluene (50 mL), and removal of the volatiles by distillation (repeat again). The residue was placed under high vacuum and the flask heated to 150° C. After drying under vacuum overnight the off white solid was dissolved in THF (100 mL) and used without further purification.

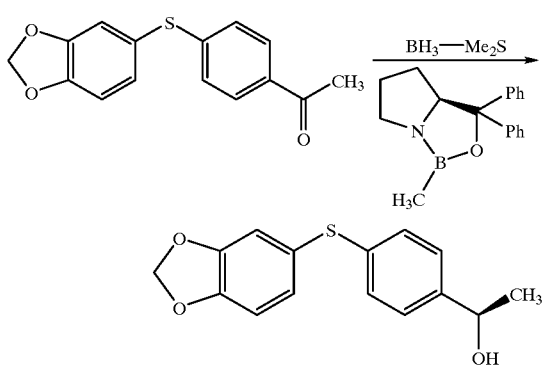

The ketone (36 g, 133 mmol) was dissolved in THF (200 mL), followed by addition of the catalyst (8.8 g in 80 mL THF). Borane dimethyl sulfide (42 mL, 2 mol/L in THF) was added dropwise, and the reaction stirred for 30 min. Methanol (200 mL) was added and the solution concentrated. The residue was dissolved in ethyl acetate and washed with water and brine. The solution was dried over sodium sulfate, filtered and concentrated to give 40.3 g of a pink oil.

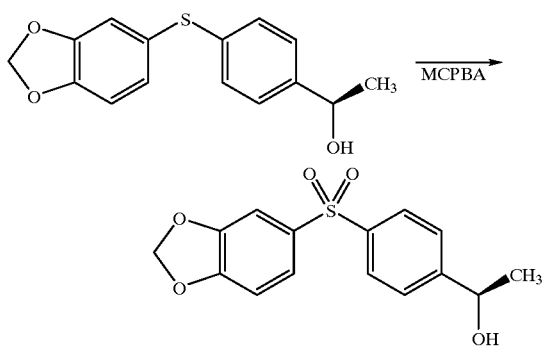

A dichloromethane (600 mL) solution of the sulfide (40.3 g, 147 mmol) was cooled in an ice water bath where MCPBA (79.7 g, 70%) was added in portions. After stirring for 1 h the temperature was warmed to room temperature and stirred for 4 h. After diluting with methylene chloride the reaction was washed with 10% sodium carbonate, water, and brine. The solution was dried over sodium sulfate, filtered and concentrated to collect 42.5 g of an off white solid.

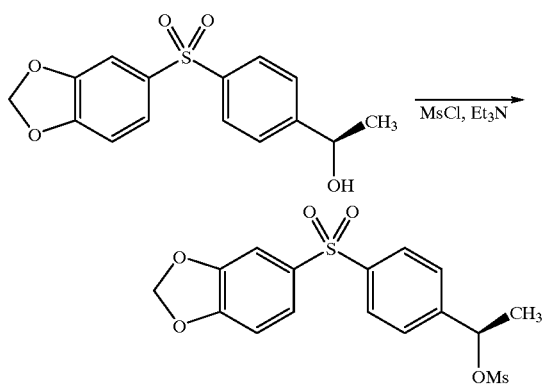

A dichloromethane (250 mL) solution of the alcohol (21.4 g, 70 mmol) and triethyl amine (19.5 mL) was cooled in an ice water bath where methanesulfonyl chloride (6.5 mL) were added dropwise. After 1 h the reaction was diluted with dichloromethane and washed with 2% HCl, water, saturated sodium bicarbonate, water, brine, and dried over sodium sulfate. Filtration and concentration gave 27 g of an oil which was used without further purification.

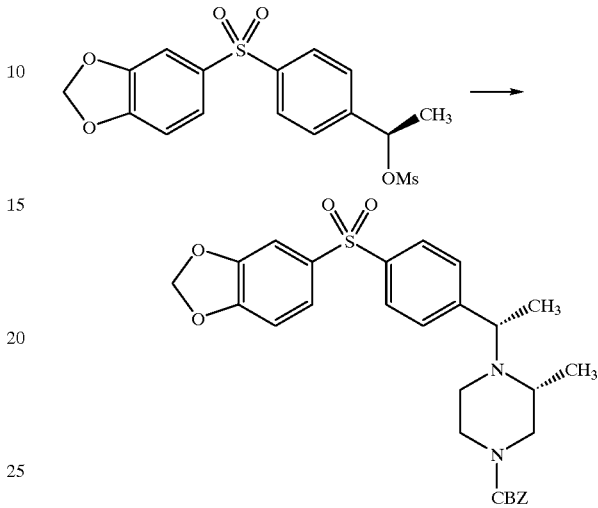

A mixture of the mesylate (made from 21.4 g alcohol), piperazine (18 g, 0.07 mol), and 2,2,6,6-tetramethyl piperidine (11.8 g, 0.084 mol) was stirred in acetonitrile (200 mL) at reflux overnight. After cooling to room temperature the acetonitrile was removed on a roto vap and replaced with ethyl acetate. The solution was washed with 10% sodium carbonate, and water. After concentration the residue was chromatographed on silica gel using 1:3 ethyl acetate/hexane. 21.9 g (60%) of a gum was collected.

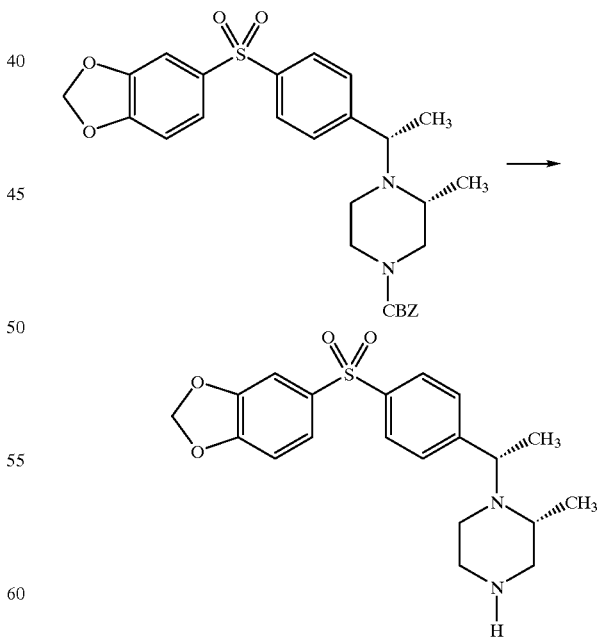

A mixture of the CBZ amine (10.3 g, 19.6 mmol), 100 mL water, methanol (100 mL), and 100 mL conc, HCl was heated in an oil bath at 100° C. for 5 h. The mixture was cooled in an ice bath and 50% sodium hydroxide was added until the pH=9. Ethyl acetate was added, followed by separation and washing with water. The organic solution was concentrated and the residue chromatographed on silica gel (methylene chloride:methanol 50:1, saturated with ammonium hydroxide solution). The product was collected in 86% as a heavy oil.

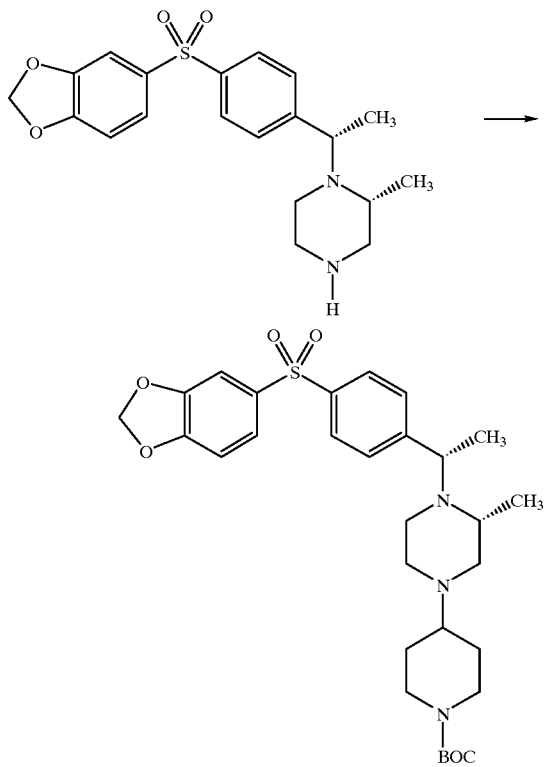

The amine (1.0 g, 2.5 mmol), N-BOC piperidinone (0.5 g, 2.5 mmol), and HOAc (0.15 mL) were dissolved in methylene chloride (20 mL).NaBH(OAc)$_3$ (0.55 g, 3.8 mmol) was added in several portions and the solution stirred overnight. Methylene chloride was added and washed with saturated sodium bicarbonate, water and brine. The solution was dried over sodium sulfate, filtered and concentrated. The residue was chromatographed using ethyl acetate. A colorless gum (0.96 g) was obtained in 65% yield.

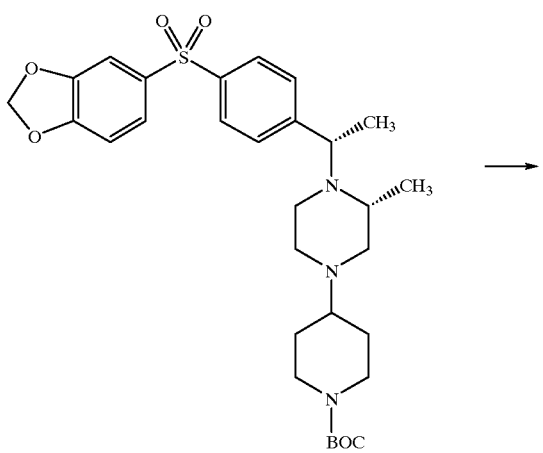

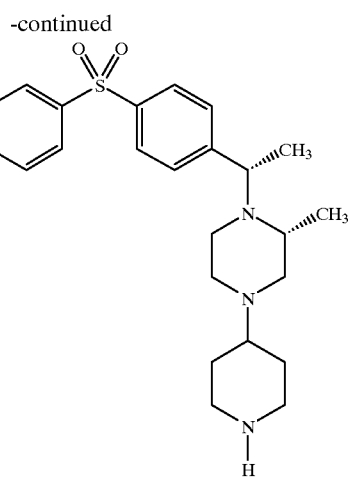

The N-BOC compound (0.87 g, 1.5 mmol) was dissolved in ethyl acetate (20 mL), and 6N HCl (3.5 mL) was added with stirring. After 2 h methylene chloride was added and the solution was washed with saturated sodium bicarbonate, and dried over sodium sulfate. After filtration the solution was concentrated and dried under vacuum to give a white powder (0.6 g, 85%).

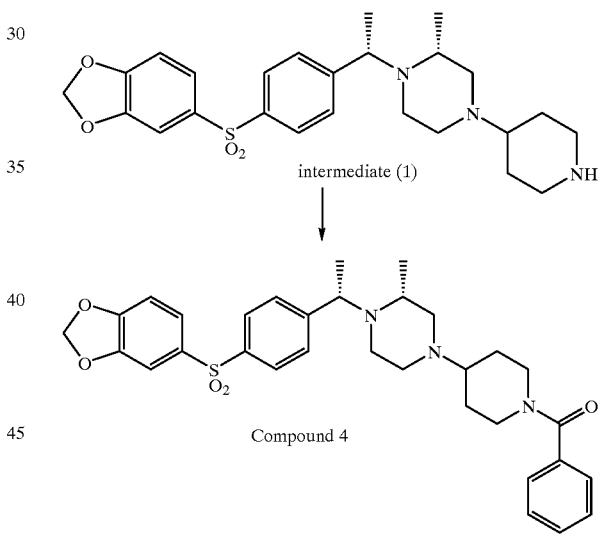

intermediate (1)

Compound 4

Stir for 20 h. at RT a solution of intermediate (1) (0.025 g), N-hydroxybenzotriazole (0.01 g), benzoic acid (0.0125 g), triethylamine (0.01 mL) and N-ethyl-N-(3-dimethylaminopropyl)-carbodiimide hydrochloride (0.025 g) in DMF (0.3 mL). Dilute with EtOAc, wash with water and with sodium bicarbonate solution, dry over MgSO$_4$ and filter through a small plug of silica gel, washing with EtOAc. Evaporate to obtain the free base form of the title compound. Dissolve this in CH$_2$Cl$_2$ (0.2 mL) and add to a solution of HCl in dioxane (4M; 0.1 mL) in ether (1.5 mL). Stir for 5 min., centrifuge, wash by suspension and centrifugation 3× with ether and dry at RT in a stream of nitrogen, then at high vacuum to obtain the dihydrochloride.

mp: 215–225° C., with decomposition.

Mass spectrum: MH+=574.

EXAMPLE 2

Synthesis of Compound No. 17

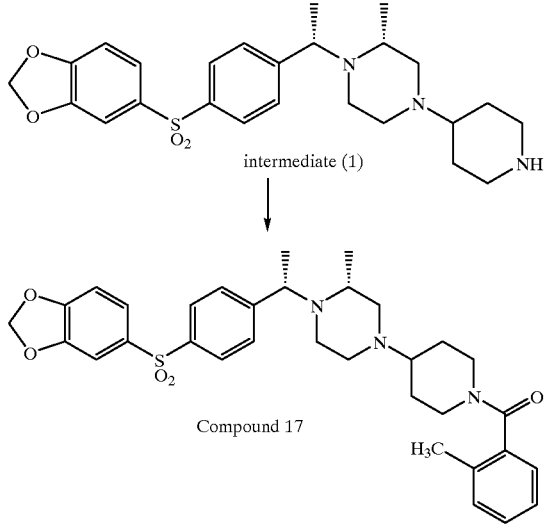

Stir for 20 h. a mixture of intermediate (1) from example 1, (0.05 g), CH₂Cl₂ (1.5 mL), o-toluoyl chloride (0.1 mL) and 1N aq. sodium hydroxide (2 mL). Separate the organic phase, dry and evaporate. Purify by preparative tlc, eluting with 5% MeOH—CH₂Cl₂. Extract the major band with 50% MeOH—CH₂Cl₂ and evaporate. Precipitate, wash and dry the hydrochloride (yield =0.065 g) in the manner described in the foregoing preparation.

mp: 182–190° C. with decomposition.

Mass spectrum: MH+=588.

EXAMPLE 3

Synthesis of Compound No. 28

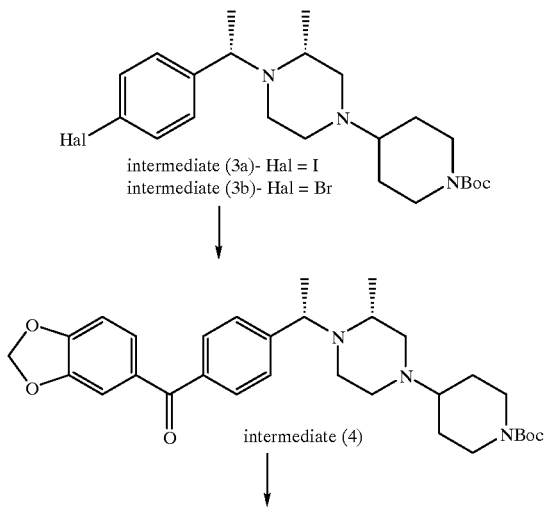

This synthesis can be carried out using either intermediate (3a) or (3b) produced as shown in examples 10 and 11. To a solution of (3b) (1.86 g) in dry THF (30 mL) at −70° under N₂ add n-BuLi (2.5 M in hexanes; 1.6 mL), stir for 10 min. and add a solution of N-piperonoyl-N,O-dimethylhydroxylamine (0.83 g) in THF (1 mL). Stir without cooling for 2 h., add EtOAc, wash with water, dry (MgSO₄) and evaporate. Chromatograph on silica gel with EtOAc—CH₂Cl₂ to obtain the major component intermediate (4) as a thick oil (1.21 g). Stir a solution of (4) (0.4 g) in EtOAc (24 mL) and conc. hydrochloric acid (4.5 mL) at RT for 3 h. Dilute with EtOAc, and wash with excess 1N sodium hydroxide solution. Extract with EtOAc, wash with saturated brine, dry and evaporate to obtain the NH compound. Dissolve this in CH₂Cl₂ (10 mL), and stir for 20 h. at RT with o-toluoyl chloride (0.15 g and NaOH (0.8 g) in H₂O (10 mL). Extract with CH₂Cl₂, dry (MgSO₄), evaporate and chromatograph on silica gel with 4% MeOH—CH₂Cl₂. Evaporate the pure fractions to obtain the free base as a foam (0.33 g) Dissolve a small portion this in CH₂Cl₂ and precipitate the hydrochloride salt as described in previous preparations.

mp: 200–210° C., with decomposition.

Mass spectrum: MH+=554

EXAMPLE 4

Synthesis of Compound No. 30

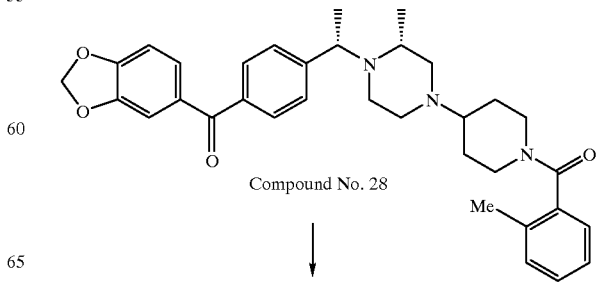

33
-continued

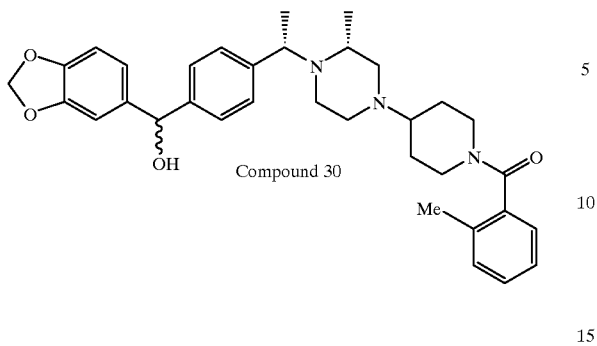

Compound 30

Stir a solution of the product of example 3 (0.31 g), ethanol (15 mL) and sodium borohydride (0.042 g) at RT for 3 h. Evaporate, add water, extract with EtOAc, dry, evaporate and chromatograph on silica gel with 10% MeOH—CH$_2$Cl$_2$ to obtain the product (0.28 g) as a white foam, a mixture of diastereoisomers.

mp: 85–95° C.

Mass spectrum: MH+=556

EXAMPLE 5

Synthesis of Compound No. 31

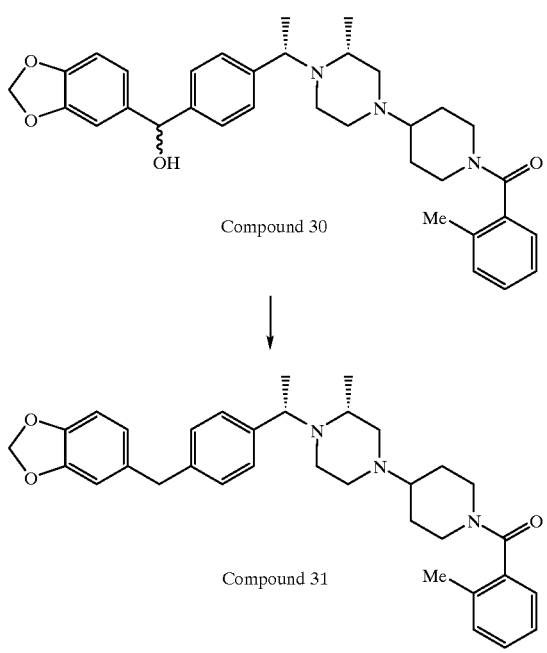

Compound 30

Compound 31

Stir a solution of the product of example 4 (0.1 g) in CH$_2$Cl$_2$ (3 mL) and add triethylsilane (0.3 mL) and trifluoroacetic acid (0.12 mL). Stir at RT for 72 h. Add excess 1N NaOH solution, extract with EtOAc, dry, evaporate and purify by preparative tlc on silica plates, eluting with 5% MeOH—CH$_2$Cl$_2$. Remove and extract the major band, evaporate the eluate, and convert to the hydrochloride in the usual manner, to obtain a white powder (0.08 g).

210–215° C., with decomposition.

Mass spectrum: MH+=540

34

EXAMPLE 6

Preparation of Compound No. 24

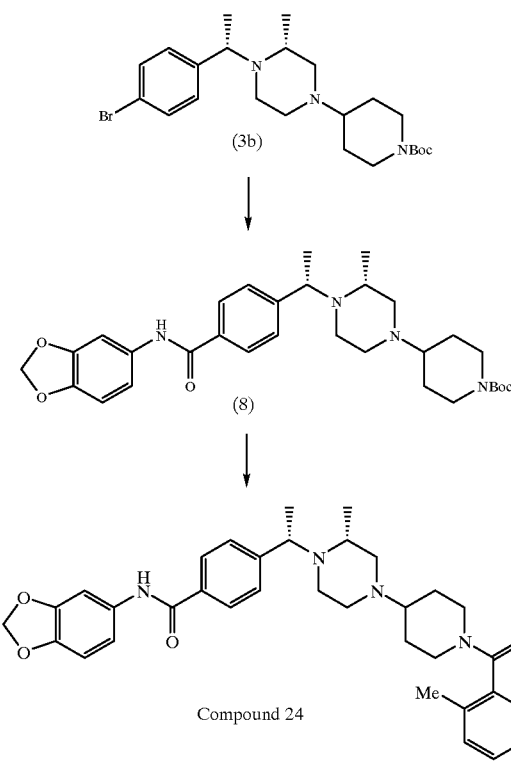

(3b)

(8)

Compound 24

To a solution of (3b) (Example 10) (1.38 g) in dry THF (20 mL) at −70° under dry N$_2$ add n-BuLi (2.5M in hexanes; 1.7 mL). Stir for 5 min., and add a solution of 3,4-methylenedioxyphenyl isocyanate (crude product, prepared by heating the corresponding acyl azide in toluene) (0.68 g) in THF (5 mL). Stir for 30 min without cooling, and work up in EtOAc-aq. sodium bicarbonate, dry (MgSO4) and evaporate. Isolate the desired compound (Rf=0.4 in 5% MeOH—CH$_2$Cl$_2$) by column chromatography on silica gel, and evaporate to a pale brown foam (0.54 g).

Convert a small portion to the HCl salt in the previously described manner.

mp: 240–250° C., with decomposition.

Mass spectrum: MH+=551.

Stir a mixture of free base (8) (0.5 g), EtOAc (5 mL) and conc. hydrochloric acid (3 mL) at RT for 2 h. Add excess aq. sodium hydroxide, extract with CH$_2$Cl$_2$, dry and evaporate to a foam (0.35 g). Dissolve 0.12 g of this in CH$_2$Cl$_2$ (4 mL) and stir for 2 h. at RT with 1N—NaOH (5 mL) and o-toluoyl chloride (0.05 mL). Separate and evaporate the organic phase, and isolate the product by preparative tlc on silica with 5% MeOH—CH$_2$Cl$_2$. Convert a small portion to the hydrochloride in the usual way.

mp: 220–230° C., with decomposition.

Mass spectrum: MH+=569

EXAMPLE 7

Synthesis of Compound No. 25

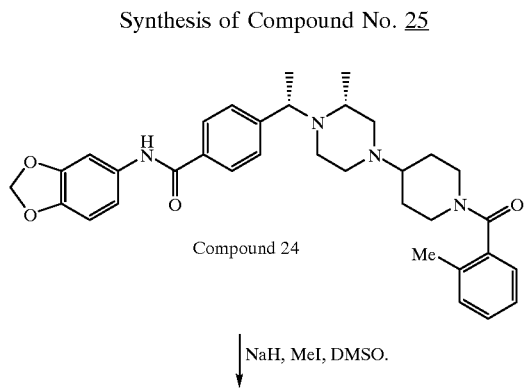

Compound 24

| NaH, MeI, DMSO.

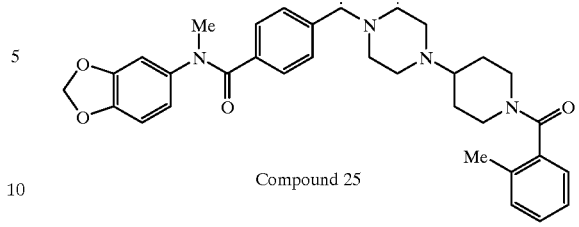

Compound 25

Stir a solution of the product of example 6 (0.08 g) in DMF (1 mL) and add sodium hydride (0.044 g), then after 10 min. add methyl iodide and stir for 30 min. Work up in EtOAc—H$_2$O, dry, evaporate, purify by preparative tlc and convert to the HCl salt as in the foregoing preparation.

mp: 190–200° C., with decomposition.
Mass spectrum: MH+=583.

EXAMPLE 8

Synthesis of Compound No. 83 and 84

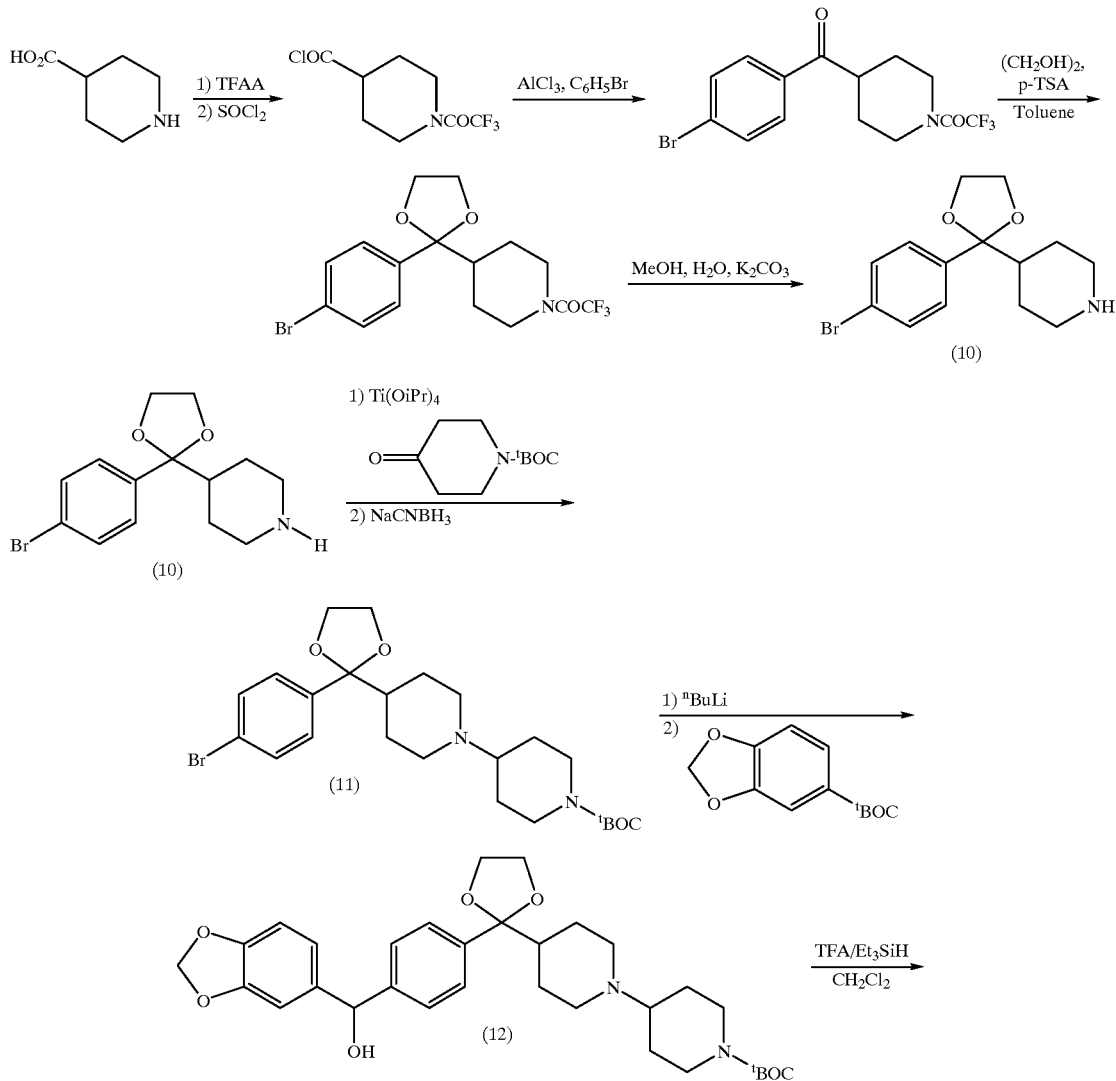

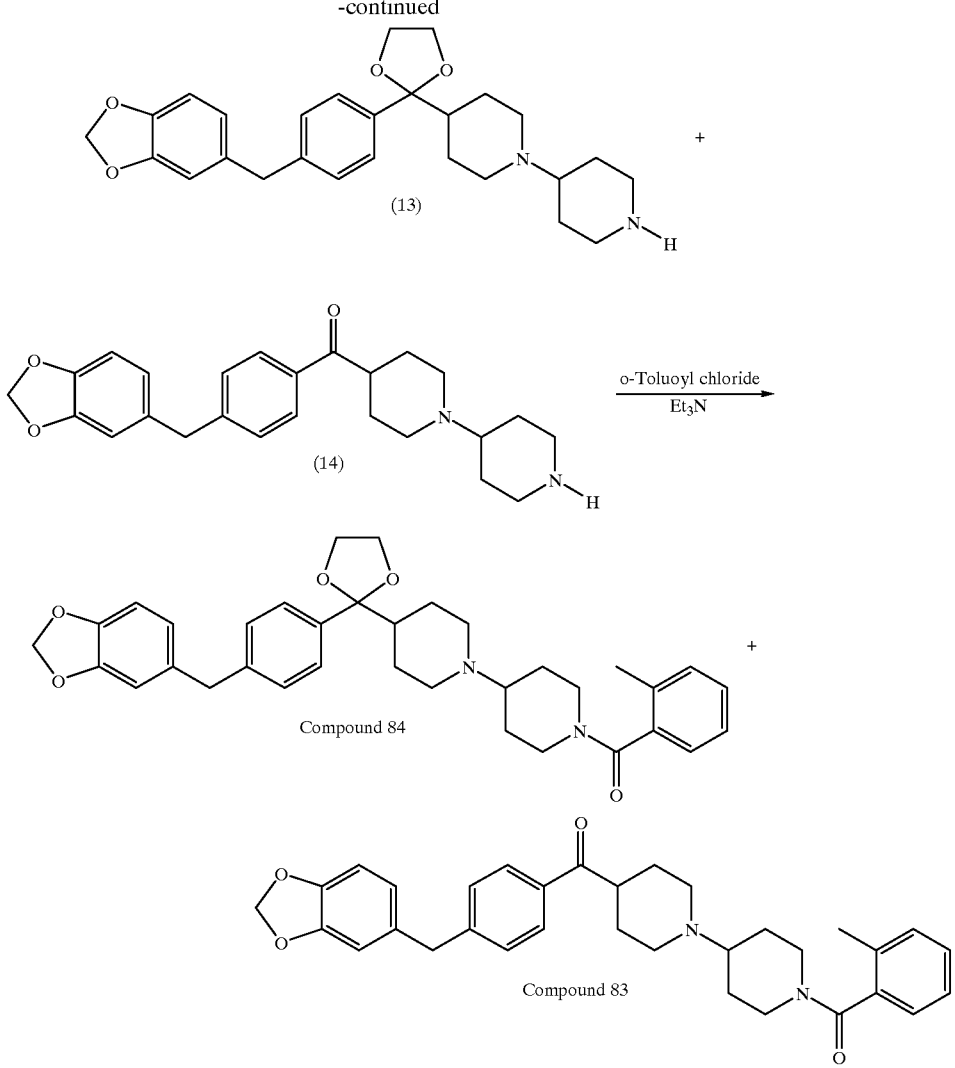

300 mL of trifluoroacetic anhydride (TFAA) was added to 96 g of isonipecotic acid at 0° C. After the addition, the reaction mixture was heated at reflux for 4 h. Excess TFAA was removed under vacuo and the reaction mixture taken up in EtOAc and washed with water and concentrated to give 160 g of the amide. 50 g of this amide was treated with 300 mL thionyl chloride and the reaction mixture heated at reflux overnight. At the end of this time excess thionyl chloride was removed under vacuo to give 54 g of the acid chloride.

11 g Aluminum chloride was added slowly to a solution of 10 g of the above acid chloride in 40 mL of bromobenzene at ambient temperature and the reaction mixture heated at reflux for 4 h. It was then cooled and poured into a mixture of conc. HCl and ice and product extracted with EtOAc. The organic layer was separated and washed with water, half saturated sodium bicarbonate solution and concentrated to give 16.21 g of the ketone.

16.21 g of the ketone was dissolved in 200 mL toluene containing 25 mL ethylene glycol and 0.5 g p-toluenesulfonic acid. The reaction mixture was heated at reflux with azeotropic removal of water until no further water was collected. The reaction mixture was concentrated to give 17.4 g of the ketal.

17.4 g of the crude ketal was dissolved in 100 mL of methanol and to this was added 25 mL of water and 12 g of potassium carbonate and the reaction mixture stirred at ambient temperature overnight. The reaction mixture was diluted with water and extracted with EtOAc. The organic layer was seeparated and washed with water and brine and concentrated to give 12.55 g of 10.

A mixture of 6.5 g of (10), 4.15 g of N-BOC-4-piperidone and 10 mL of Ti(OiPr)$_4$ was stirred at ambient temperature over night. The reaction mixture was cooled to 0° C. and 3.2 g of NaCNBH$_3$ dissolved in 40 mL of MeOH was added. The reaction mixture was then allowed to warm to ambient temperature and stirred for 1 h., diluted with 100 mL of EtOAc and quenched with a mixture of 60 mL water/20 mL of conc. NH$_4$OH. The mixture was stirred for 1 h. and filtered though celite. The aqueous layer was extracted with 3×100 mL of EtOAc. The combined organic layers were dried over MgSO$_4$, filtered and concentrated. The crude was purified by flash chromatography using 100% EtOAc as eluent. To give 6.8 g, 66% of (11).

To a stirred solution of (11) in 25 mL of THF at −78° C. was added 1.7 mL (1.6M in Hex.) of $^n$BuLi. The mixture was stirred at −78° C. for 10 min., then 700 mg of piperonal dissolved in 5 mL of THF was added. The mixture was allowed to reach ambient temperature and stirred for 2 h. The mixture was quenched with 30 mL of water and extracted with 3×50 mL of EtOAc. The combined organic layers were dried over MgSO$_4$, filtered and concentrated. The crude was purified by silica gel flash chromatography using 10% Et$_3$N-ether to give 475 mg, 41.5% of (12).

To a stirred solution of 475 mg of (12) and 1 mL of Et$_3$SiH in 10 mL of methylene chloride was added 3 mL of TFA. The mixture was stirred at ambient temperature for 2 h. The solvent was evaporated and the residue was taken up in 20 mL of methylene chloride, washed with 20 mL of 10% NaOH. The aqueous layer was extracted with 3×30 mL of methylene chloride, the combined organic layers were dried over MgSO$_4$, filtered and concentrated to give a mixture of (13) & (14) which was used without purification. (350 mg, 90%)

dissolving the free base in EtOAc and adding HCl-ether solution. After evaporating the solvent, the salts were collected as powder.

Compound No. 83 (50 mg, 54%) (M+H)$^+$ Cal: 525.2753; Found: 525.2746

Compound No. 84 (190 mg, 50%) (M+H)$^+$ Cal: 569.3015; Found: 569.3022

EXAMPLE 9

Synthesis of Compound No. 85

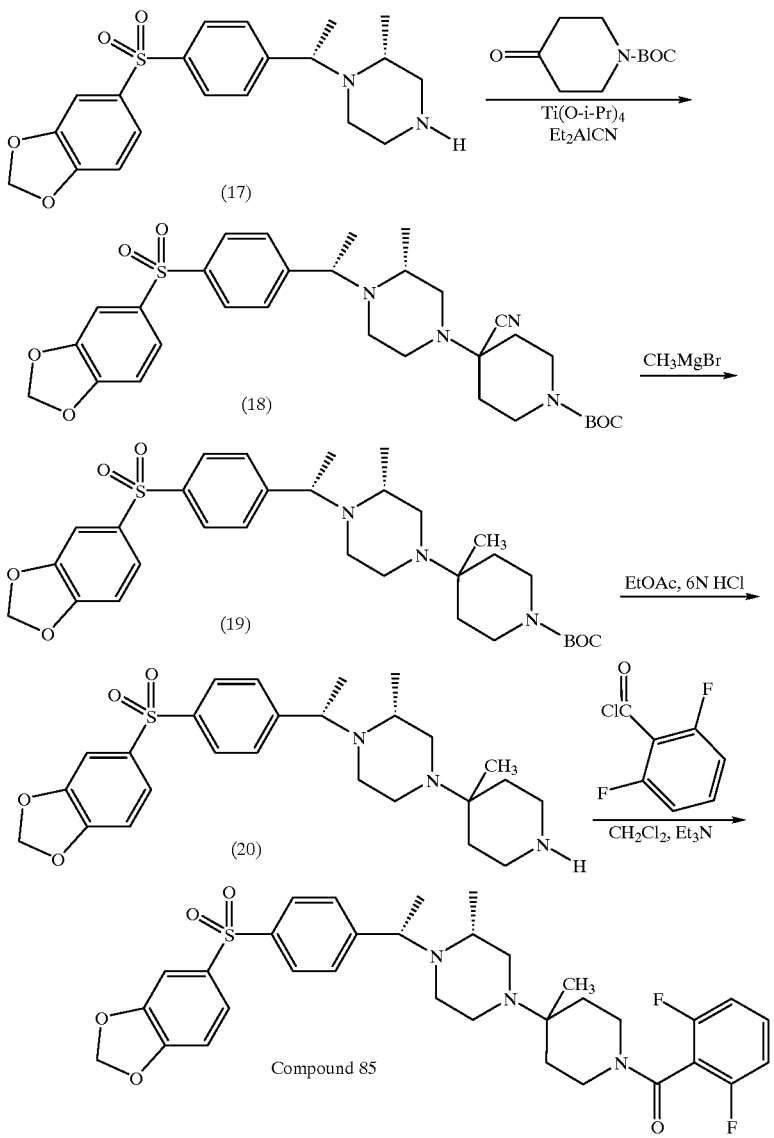

350 mg of the crude mixture of (13) and (14) and 1 mL of Et$_3$N in 10 mL of methylene chloride was treated with 0.5 mL (1.2 eq.) of o-toluoyl chloride for 3 h. The mixture was then concentrated and the residue purified by silica gel prep. TLC using 4% Et$_3$N-ether to give compounds 83 and 84. The HCl salts of compounds 83 and 84 were prepared by The piperazine (17) (1.1 g, 2.8 mmol), prepared as described in example 1, is dissolved in methylene chloride (10 mL) followed by addition of the N-BOC piperidinone (0.85 g, 4.25 mmol) and titanium tetraisopropoxide (0.8 g, 2.8 mmol). The mixture is stirred overnight at room temperature. A 1 molar toluene solution of diethylaluminum cyanide (6.5 mL, 5.6 mmol) is added, via syringe, and the mixture stirred for an additional 20 h. The mixture is then diluted with ethyl acetate and washed with 10% sodium carbonate, water and brine. The organic phase is concentrated in vacuo and the residue chromatographed through a silica gel column (1:1 ethyl acetate/hexane). The product (18) is collected as a colorless oil (0.93 g, 55%).

The cyano intermediate (18) (0.13 g, 0.19 mmol) is dissolved in THF (4 mL) followed by the addition of methyl magnesium bromide (0.64 mL, 3.0 M, 1.9 mmol), via syringe. After stirring for 10 min the temperature is raised to 60° C. where stirring is continued for 2.5 h. Cooling to room temperature is followed by quenching with water (1 mL) and then saturated sodium bicarbonate (20 mL). After 10 min ethyl acetate (50 mL) is added, stirred vigorously, and separated. The organic layer is washed with brine and dried over sodium sulfate. Filtration and concentration with under vacuum gives a viscous oil which is purified on silica gel prep TLC plates (100% ethyl acetate). The intermediate (19) is collected in 60% yield.

The N-BOC piperidine (19) (0.27 g, 0.4 mmol) is dissolved in ethyl acetate (10 mL) and 1.5 mL of a 6N HCl solution added with vigorous stirring. After 1.5 h saturated sodium bicarbonate is added until the pH was basic. Methylene chloride (25 mL) is added and the layers separated, and the aqueous phase extracted with methylene chloride. The organic layer is dried over sodium carbonate, filtered and concentrated to collect 0.22 g, 95%, of (20) as a thick oil which solidifies under vacuum.

The amine (20) (0.025 g, 0.044 mmol) is dissolved in methylene chloride (1 mL) followed by the addition of triethyl amine (11 uL, 0.08 mmol) and the 2,6-difluorobenzoyl chloride (0.014 g, 0.08 mmol). After stirring at room temperature overnight saturated sodium bicarbonate and methylene chloride are added. The layers are separated and the organic phase dried over sodium sulfate. The solvent is removed and the residue dissolved in ethyl acetate. The solution was placed on a preparative TLC plate and eluted with ethyl acetate (100%). Compound 85 is collected as a clear oil (0.026 g), yield=95%. This is converted to the dihydochloride salt as follows: The free amine (26 mg) is dissolved in 1 mL ethyl acetate and stirred while HCl/ether is added until the pH persists at 2. The precipitate is transferred to a centrifuge tube and spun in a centrifuge. The supernatant was removed and replaced with ether (gentle stirring with a spatula), and the sample spun again. The process is repeated 3×. After removal of the solvent, the solid is transferred to a vial where it is dried under vacuum. 15 mg of a white solid was collected (m.p.=242–245 dec).

EXAMPLE 10

Synthesis of Intermediate (3a) from Example 3

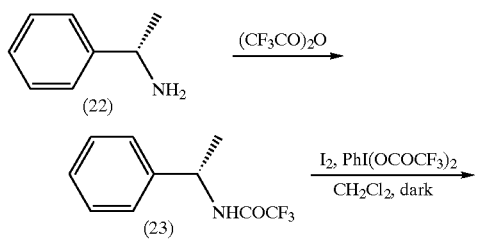

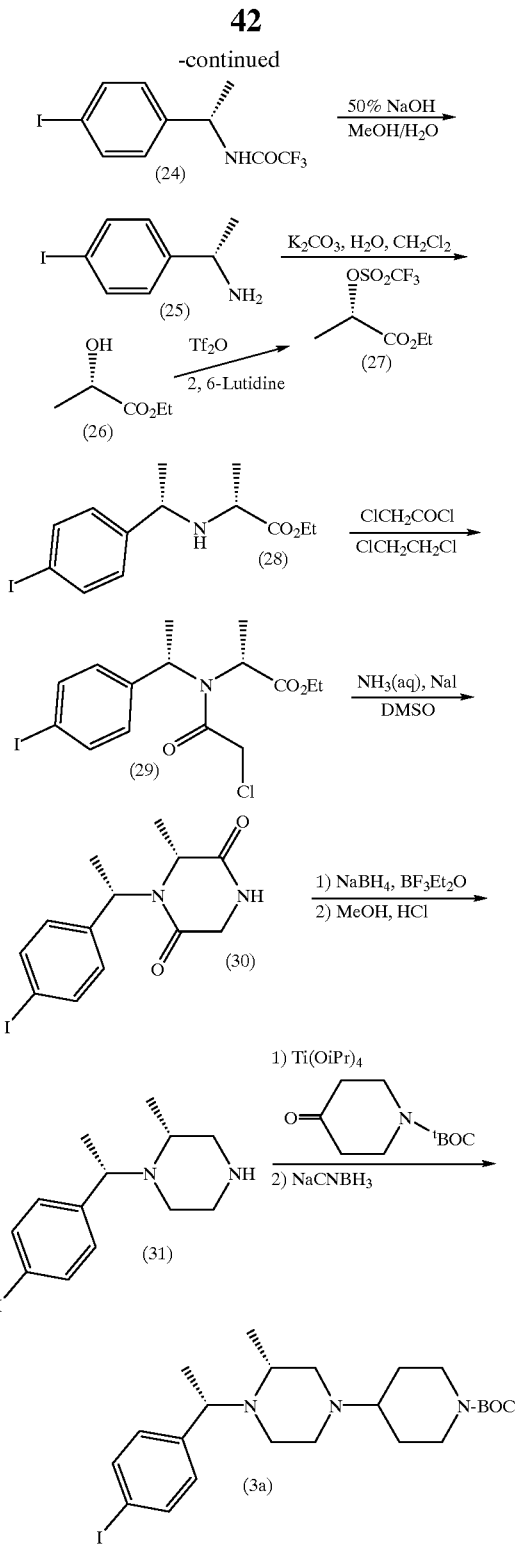

Step 1

Trifluoroacetic anhydride (150 mL, 1.06 mol) in methylene chloride (500 mL) was cooled to 0° C. A solution of (S)-α-methylbenzylamine (22) (100 g, 0.83 mol) in methylene chloride (200 mL) was added slowly over 30 min. The cooling bath was removed and the mixture was stirred for ~2 h, transferred to a separatory funnel, washed with water, dried over anhydrous magnesium sulfate, filtered, and concentrated to give 189 g (~100%) of (23) as a white solid Step 2

Iodine (41 g, 162 mmol) was added to a solution of (23) (65.4 g, 301 mmol) in methylene chloride (500 mL) at room temperature. [Bis(trifluoroacetoxy)iodo]benzene (75 g, 174 mmol) was added. The mixture was stirred for 30 min, a mild exotherm occurs (30° C.), then kept in the dark overnight. The mixture was added slowly to a stirred mixture of sodium bicarbonate (50 g), sodium bisulfite (10 g) and water (600 mL), washing in with methylene chloride. The mixture was stirred for 15 min, filtered and the filter cake was well washed with methylene chloride until TLC (100% $CH_2Cl_2$, Rf=0.75) shows no product in the washings. (Note: the initial solid contains considerable product which is moderately soluble in methylene chloride). The filtrate was dried over anhydrous magnesium sulfate, filtered through a 1" pad of flash silica gel, washing with 2% ether/$CH_2Cl_2$. The filtrate was evaporated to a slurry, ether (~75 mL) and hexanes (~700 mL) were added and the mixture was stirred for 30 min. The resulting solid was collected, washed well with hexanes, air dried and then dried under vacuum to give 63.05 g (61%) of (24) as a white solid. Filtrates were evaporated to an oil and some crystals, added hexanes (500 mL), stirred at room temperature for 1 h, collected and additional 4.6 g (4%) of (24)

Step 3

(24) (10 g, 29.15 mmol) was dissolved in methanol (150 mL) and water (15 mL). 50% NaOH (30 g) was added and the mixture was stirred at room temperature overnight (20 h). TLC (50% EtOAc/hex.) indicated consumption of starting material. Most of methanol was removed in vacuo, the residue was dissolved in water and methylene chloride, transferred to a separatory funnel and extracted with methylene chloride. The extracts were combined, dried over anhydrous sodium carbonate, filtered and concentrated to give 6.7 g (93%) of (25) as a white solid.

Step 4

Triflic Anhydride (10.6 mL, 62.98 mmol) was added to a 0° C. solution of (S) ethyl lactate (26) (7.0 mL, 61.75 mmol) in methylene chloride (100 mL) at 0° C. 2,6-Lutidine (7.55 mL, 64.83 mL) was added and the mixture was stirred for 1 h. the mixture was transferred To a separatory funnel, washed with 0.5 M HCl and brine, dried over anhydrous sodium sulfate, concentrated almost to dryness, filtered through a plug of silica eluting with methylene chloride, conc. to provide 10.8 g (70%) (27) as a reddish oil.

Step 5

(25) (6.7 g, 27.11 mmol) was added to a mixture of methylene chloride (90 mL), water (90 mL) and potassium carbonate (5.5 g, 39.6 mmol). Ethyl (S) lactate triflate (27)(7.5 g, 29.82 mmol) was added and the mixture was stirred overnight (20 h). TLC (50% EtOAc/hex.) indicated consumption of starting material. Ammonia (conc.) (30 mL) was added, stirred 15 min, transferred to a separatory funnel, washed with water, dried over anhydrous sodium sulfate, filtered and concentrated to give 10.3 g (~110%) of (28).

Step 6

Chloroacetyl chloride (12 mL, 150 mmol) was added to a solution of (28) (9.37 g, 27.11) in dichloroethane (80 mL). The mixture was refluxed for 2 h. TLC (20% EtOAc/hex.) indicated consumption of starting material. The solution was cooled to room temperature, diluted with methylene chloride, water (200 mL) followed by potassium carbonate (~15 g) was added in small portions. The mixture was stirred for an additional 15 min., transferred to a separatory, washed with water, dried over anhydrous sodium sulfate, filtered and concentrated to give 11.53 g (~110%) of (29).

Step 7

(29) (27.11 mmol) was dissolved in dimethyl sulfoxide (120 mL). Concentrated aqueous ammonia (24 mL) and sodium iodide (13 g) was added. Methanol (10 mL) was used to was in the sodium iodide. The mixture was stirred over the weekend (60 h, overnight is sufficient). TLC (50% EtOAc/hex.) indicated consumption of starting material. Water (500 mL) was added, the mixture was stirred for 30 min and the resulting precipitate was collected via vacuum filtration. The precipitate was well washed with water and dried under vacuum to afford 8.2 g (84%) of (30).

Step 8

(30) (8.2 g, 22.9 mmol) was added to a mixture of sodium borohydride (8.66 g, 228.9 mmol) in dimethoxyethane (250 mL). Boron trifluoride etherate (16.9 mL, 137.3 mmol) was added and the resulting mixture was refluxed under nitrogen for 3 h. TLC (5% MeOH/$CH_2Cl_2$) indicated consumption of starting material. The mixture was cooled to 0° C., methanol (60 mL) was added slowly and the resulting mixture was stirred for 20 min. Concentrated HCl (10 mL) was added slowly and the resulting mixture was refluxed for 1 h. TLC (5% MeOH/$CH_2Cl_2$) indicated formation of a more polar product consistent with an amine. The mixture was cooled to room temperature and concentrated almost to dryness. The residue was partitioned between 2N sodium hydroxide and methylene chloride, transferred to a separatory funnel and extracted with methylene chloride. The extracts were combined, washed with water, dried over anhydrous sodium sulfate and concentrated to provide 6.5 g (87%) of (31) as an oil.

Step 9:

Intermediate (31) was coverted to 3a using using procedures described in example 8.

EXAMPLE 11

Synthesis of Intermediate (3b) from Example 3

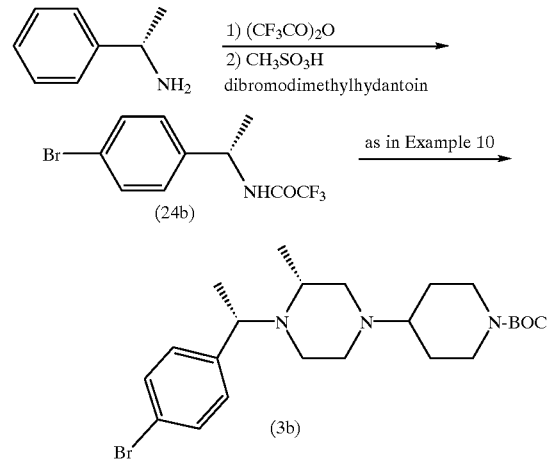

A solution of trifluoroacetic anhydride (0.4 mol) in 300 mL cold methylene chloride is treated with 0.3 mol (S)-α-methylbenzylamine in 100 mL methylene chloride. The resulting mixture is stirred with ice cooling for 30 minutes and at room temperature of 1.5 hours. The solution is again cooled in an ice bath and 80 mL methansulfonic acid is added followed by 45 grams dibromodimethylhydantoin. Stirring is continued until the mixture is homogeneous, then the mixture is allowed to stand overnight in the dark. A solution of 20 g $NaHSO_3$ in 300 mL ice water is added. The organic layer is separated and washed twice with water and dried over magnesium sulfate. The solution is filtered through a 4" pad of flash-grade silica gel, eluting with 400 mL methylene chloride, and evalporated to a solid. The solid is suspended in 200 mL ether and 1L hexane is added. After stirring 30 minutes, the solids are collected, washed with hexane, and dried to give 35.7 grams of intermediate (24b). This compound is converted to (3b) using the same sequence described in scheme 9.

EXAMPLE 12

Synthesis of Compound No. 53

The crude ketal (33) (0.83 g, ~1.45 mmol) was dissolved in ethylene glycol (44 mL) and crushed KOH (2.90 g, 51.6 mmol) was added to the rigorously stirred solution. The reaction was heated for 24 h at 100° C. After cooling to room temperature, the mixture was diluted with ethyl acetate followed by the addition of 1N NaOH. The aqueous portion was extracted with ethyl acetate and the combined organics washed several times with 1N NaOH. The crude solution was dried over sodium sulfate, filtered, and concentrated to yield 0.31 g of (34) which was used without further purification.

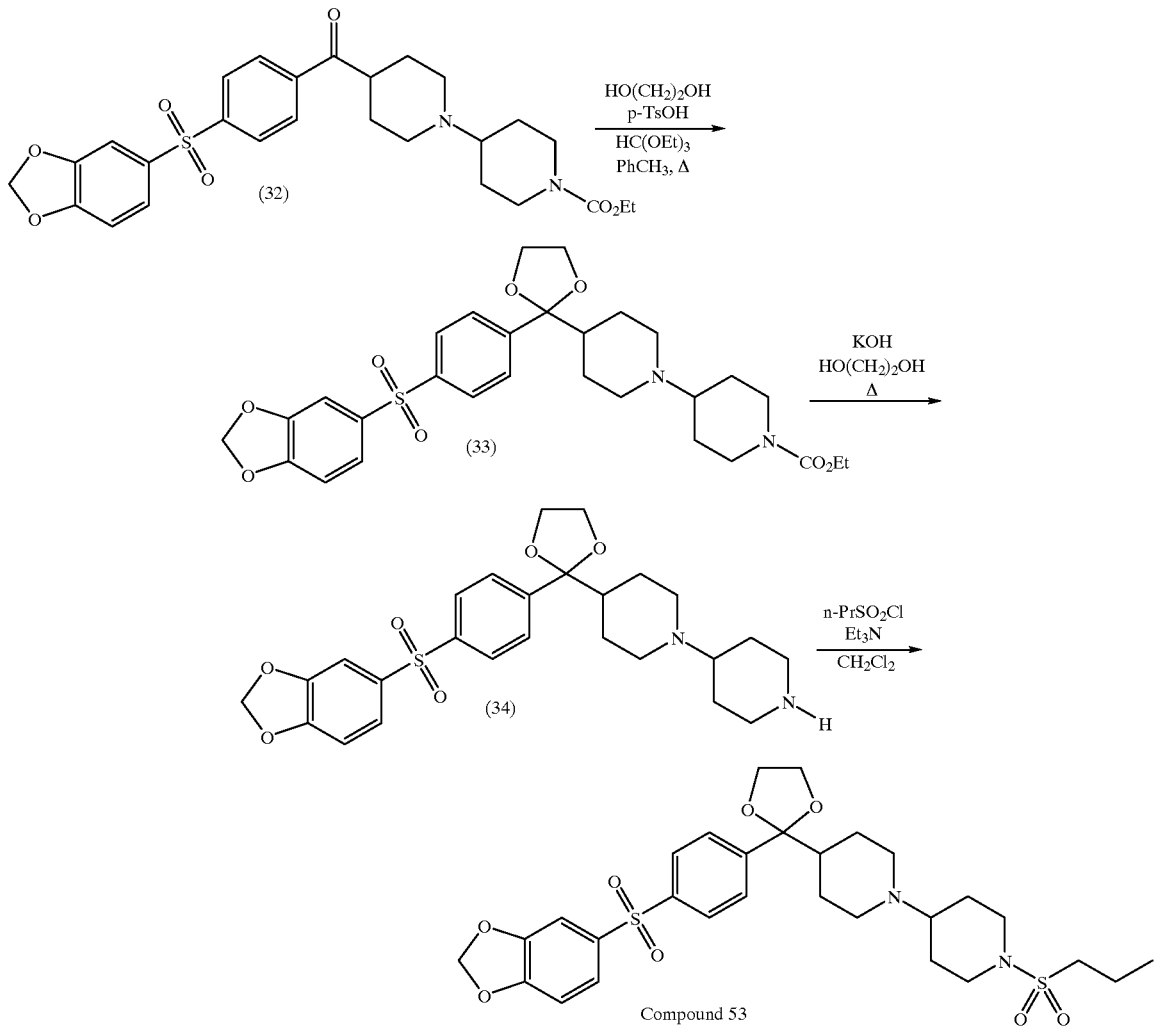

Compound 53

To a stirred solution of (32) prepared via the procedure described for intermediate (7) of example 14, but using N-ethyoxycarbonyl-4-piperidinone instead of N-tBOC-4-piperidinone (1.80 g, 3.41 mmol) in toluene (34 mL) was added dry ethylene glycol (1.33 mL, 23.8 mmol), triethylorthoformate (1.70 mL, 10.2 mmol) and p-toluenesulfonic acid monohydrate (0.97 g, 5.12 mmol). The reaction was heated overnight at 55° C. under nitrogen. The mixture was diluted with methylene chloride, washed sequentially with 1N NaOH and brine, dried over sodium sulfate, filtered and concentrated in vacuo. The resulting product (33) (2.40 g) was used without further purification.

To a solution of (34) (31.4 mg, 62.8 µmol) in methylene chloride (0.60 mL) was added n-propylsulfonyl chloride (20 µL, 178 µmol) and triethylamine (30 µL, 215 µmol). The reaction was stirred for 2 h at room temperature under nitrogen. The mixture was concentrated under reduced pressure and purified by PTLC (10/90 MeOH/$CH_2Cl_2$), yielding (35) (12.3 mg, 32% over three steps).

LRMS (FAB): (M+H)=606

EXAMPLE 13

Synthesis of Compound No. 22

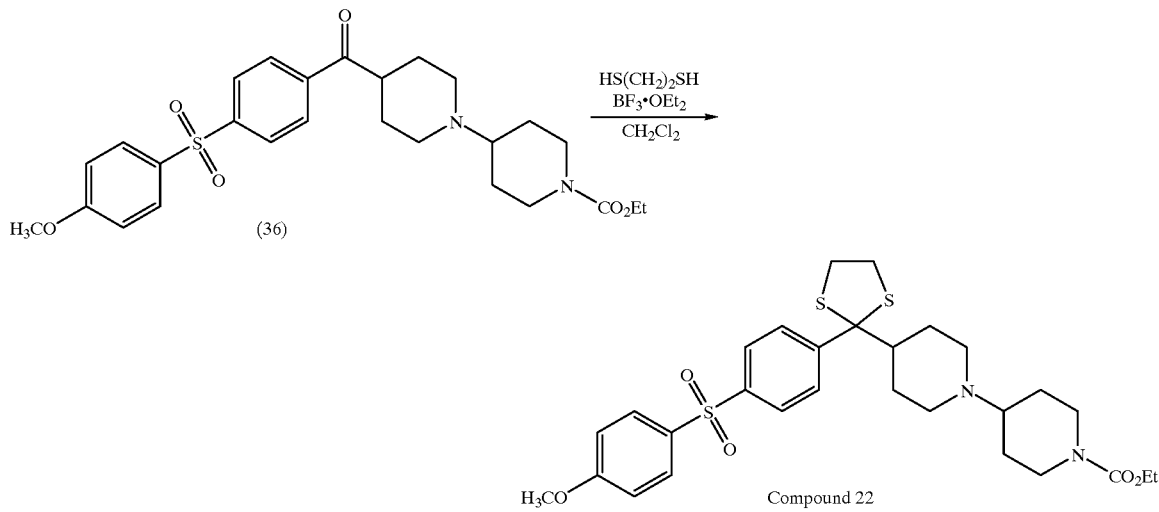

To a solution of (36) prepared via the procedure described for intermediate (7) of example 14 substituting 4-mercaptoanisole for 4-mercaptomethylenedioxybenzene and N-ethyoxycarbonyl-4-piperidinone for N-tBOC-4-piperidinone (29.5 mg, 58.9 μmol) in methylene chloride (0.24 mL) was added ethanedithiol (7.4 μL, 88 μmol) and boron trifluoride diethyl etherate (11 μL, 88 μmol). The reaction was stirred overnight at room temperature under nitrogen, then diluted with methylene chloride and washed with 10% NaOH. The crude mixture was dried over sodium sulfate, filtered, and concentrated under reduced pressure. Purification by PTLC (10/90 MeOH/CH$_2$Cl$_2$) yielded 37 (17 mg, 50% yield).

LRMS (FAB): (M+H)=591

EXAMPLE 14

Synthesis of Compound 43

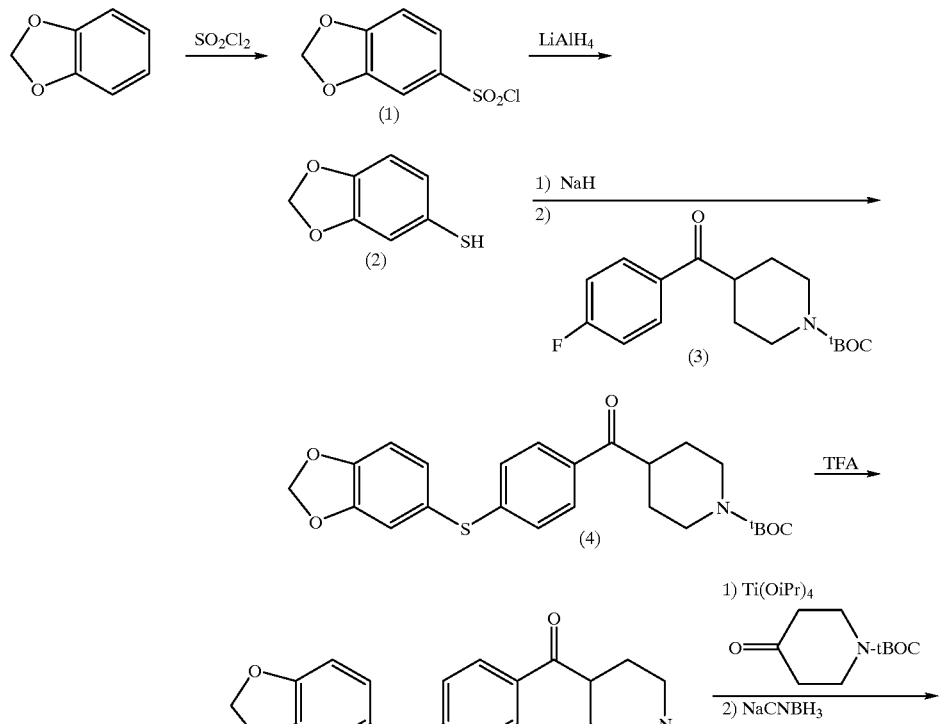

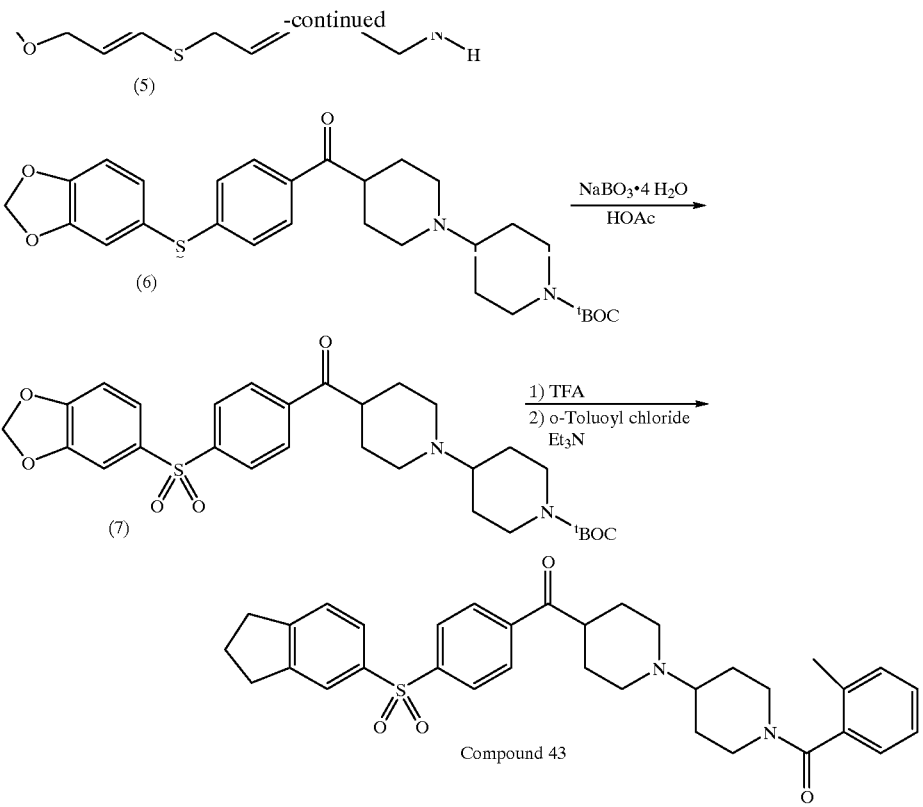

Compound 43

(1). To a stirred solution of 41 ml of anhydrous DMF was added 43 ml of sulfuryl chloride at 0–10° C. followed by slow addition of 61 grams of methylenedioxybenzene. After the addition was completed, the mixture was heated at 80° C. for 10 min., and then 5–10 min. at 110° C. The reaction mixture turned to dark brown. The mixture was cooled to 40° C. and was poured into a mixture composed of 200 ml H2O/200 g crushed ice/300 ml CHCl3. Two layers were separated, the organic layer eas dried over MgSO4, filtered, and concentrated to give a crude which was triturated with 100 ml of hexanes. (60.6 g, 53%)

(2) To a stirred suspension of 16 g LAH in 500 ml of THF at 0° C., was added dropwise 60.6 g of (1) dissolved in 100 ml of THF. The temperature was allowed to reach RT and the mixture was stirred at this temperature for 2 h. The reaction mixture was then quenched carefully with 1N HCl at 0° C. to pH=1, diluted with 1 L EtOAc. The organic phase was washed with 500 ml of water, dried over $MgSO_4$, filtered and concentrated to give a crude which was used directly in the next step without purification. (29 g, 68%)

(4) 28 g of the crude thiol (2) dissolved in 20 ml of DMF was added to a stirred suspension of 8 g of NaH(60%) in 80 ml of DMF. The mixture was stirred at RT for 1 h., ketone (3) dissolved in 150 ml of DMF was added at once. The mixture was heated at 70° C. over night.

The mixture was diluted with 400 ml of methylene chloride and then quenched with 300 ml of water. The organic phase was washed with 3×200 ml of water, dried with $MgSO_4$, filtered and concentrated to give a crude which was purified by flash chromatography using EtOAc/Hex./$CH_2Cl_2$=1/4.5/4.5 as eluents. (35 g, 53%)

(5) To a stirred solution of 6 g of (4) in in 100 ml of methylene chloride was added 10 ml of TFA. The mixture was stirred at RT for 1 h. The solvent was eliminated under reduced pressure and the residue was taken up in 100 ml of methylene extracted with 3×60 ml of methylene chloride. The combined organic phase was chloride, quenched with 50 ml of 10% NaOH. The aqueous phase was dried over $MgSO_4$, filtered and concentrated to give a crude without purification. (4.6 g, 100%)

(6) A mixture of 3.4 g of (5) 2.4 g of N-BOC-4-piperidone and 5.9 ml of Ti(OiPr)$_4$ was stirred at RT over night. 1.6 g of NaCNBH$_3$ dissolved in 40 ml of MeOH was added at 0° C. The mixture was stirred at RT for 1 h. diluted with 100 ml of EtOAc, quenched with a mixture of 60 ml water/20 ml of NH$_4$OH. The mixture was stirred at RT for 1 h. filtered though celite. The aqueous phase was extracted with 3×100 ml of EtOAc. The combined organic phases were dried over $MgSO_4$, filtered and concentrated. The crude was purified by flash chromatography using 100% EtOAc as eluent. (3.8 g, 73%)

(7) To a solution of 1.32 g of (6) in 15 ml of HOAc was added 1.41 g of NaBO$_3$.4H$_2$O, the mixture was stirred at RT for 3 days. The solvent was evaporated and the residue was quenched with 20 ml of 10% NaOH, extracted with 3×50 ml of EtOAc. The combined organic extract was dried over $MgSO_4$, filtered and concentrated. The crude was purified by silica gel prep TLC using 20%EtOH-EtOAc. (620 mg, 44%)

(8) 620 mg of (7) in 15 ml of methylene chloride and 5 ml of TFA was stirred at RT for 3 h. The solvent was evaporated and residue was treated with 10% NaOH, extrated with EtOAc. The organic extract was dried over $MgSO_4$, filtered and concentrated to give a crude. (510 mg, 100%)

0.052 mmol of the above crude free amine was reacted with 1.2 eq. of o-toluoyl chloride and 1.3 eq. of Et$_3$N in 3 ml of methylene chloride for 3 h. The mixture was concentrated and the residue was purified by silica gel prep. TLC using 20% EtOH-EtOAc. (18 mg, 50%) (M+H)$^+$ Cald: 575.2216; Found: 575.2223

The HCl salts were prepared by dissolving (8) in EtOAc and added HCl-ether solution. After evaporating the solvent, the salts were collected as powder.

EXAMPLE 15

Preparation of Compound No. 82 and trifluoroacetic acid (3 mL), relux for 3 h., evaporate, partition with CH$_2$Cl$_2$ and 1N aq. sodium hydroxide, dry and evaporate to obtain (11) as a thick oil, used as such in subsequent acylation experiments.

Stir a mixture of (11) (0.03 g), CH$_2$Cl$_2$ (2 mL) and 1N aq. sodium hydroxide (2 mL) and add 2,3-dimethylbenzoyl chloride (0.07 g). Stir at RT for 18 h., extract with CH$_2$Cl$_2$, dry and evaporate. Dissolve the residue in 1:1 CH$_2$Cl$_2$:acetone and filter through a small plug of silica gel, washing with the same solvent mixture. Evaporate, dissolve the residue in a small volume of CH$_2$Cl$_2$ and precipitate the dihydrochloride by adding to excess HCl in ether as described in earlier preparations Wash with ether and dry to

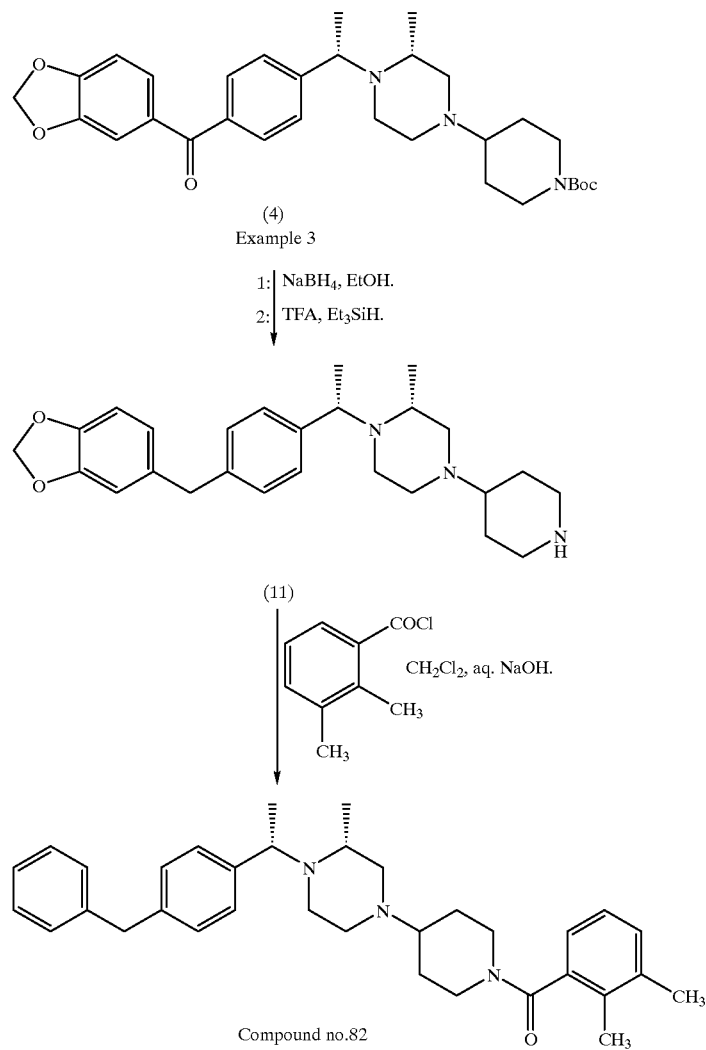

Stir a solution of compound (4) (0.5 g) and sodium borohydride (0.2 g) in ethanol (3 mL) at RT for 3 h. Add water, extract with CH$_2$Cl$_2$, dry over MgSO$_4$ and evaporate. To the residue in CH$_2$Cl$_2$ (5 mL) add triethylsilane (3 mL)

obtain the product compound No. 82 as an off-white powder (0.036 g).

mp: 207–212° C., with decomposition.

Mass spectrum: MH+=554.

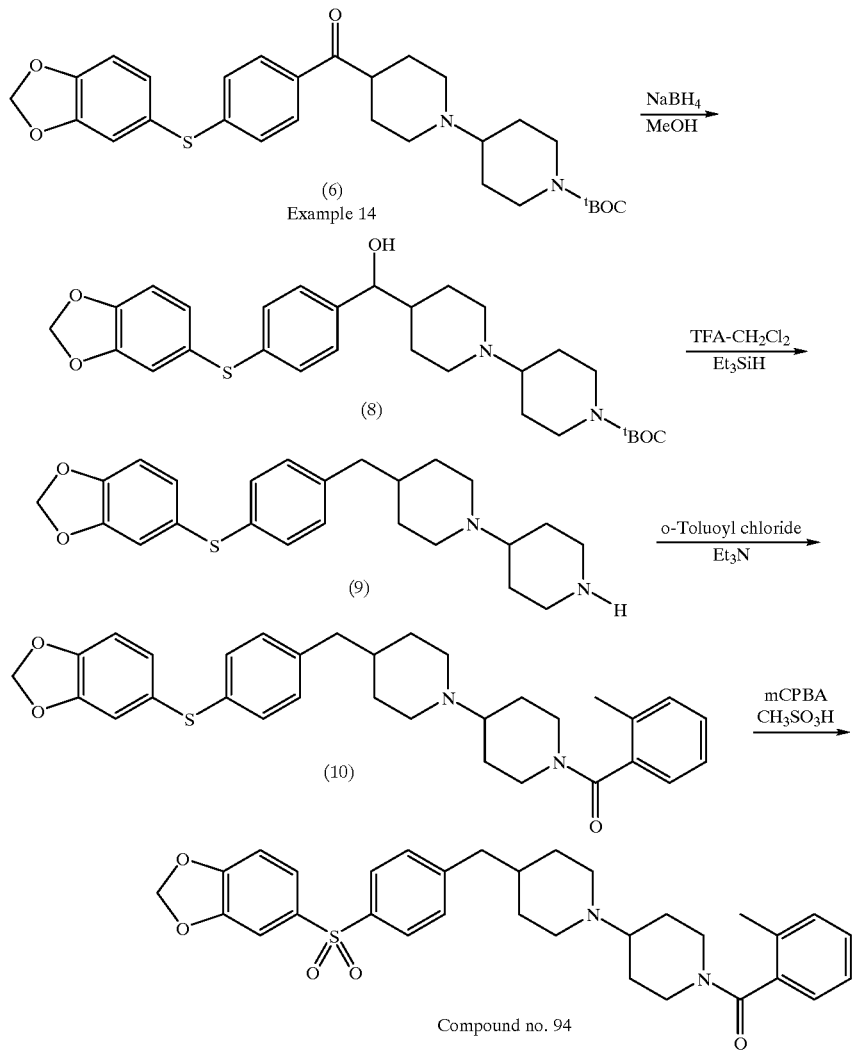

To a stirred solution of 899 mg (1.72 mmol) of 4, prepared as described in Example 14, in 15 ml of anhydrous methanol is added by portion 130 mg of NaBH$_4$. The mixture is stirred at room temperature for 30 min. and then quenched with 15 ml of 10% NaOH solution. The aqueous layer is extracted with 4×20 ml of ethyl acetate. The combined organic layers are dried over Na$_2$SO$_4$, filtered and concentrated to give 859 mg (95%) of 8.

To a stirred solution of 850 mg of crude 8 in 5 ml of CH$_2$Cl$_2$ is added 563 mg (3 eq.) of triethylsilane, followed by 2 ml of TFA. The mixture is stirred at room temperature for 3 hrs. and then is concentrated. The residue is taken up in 15 ml of CH$_2$Cl$_2$ and 15 ml of 10% NaOH. The aqueous layer is extracted with 3×15 ml of CH$_2$Cl$_2$. The combined organic layers are dried over MgSO$_4$, filtered and concentrated to give 600 mg (92%) of crude 9.

To a stirred solution of 600 mg of 9 and 455 mg of triethylamine in 5 ml of CH$_2$Cl$_2$ is added 464 mg of o-toluoyl chloride. The mixture is stirred at room temperature for 2 hrs. The mixture is quenched with 20 ml of water, extracted with 3×20 ml of EtOAc. The combined organic layers are dried over MgSO$_4$, filtered and concentrated to give a crude. Purification on silica gel prep TLC affords 555 mg (70%) of 10.

To a stirred solution of 43 mg of 10 and 0.5 ml of MeSO$_3$H (0.5 M-CH$_2$Cl$_2$) in 5 ml of CH$_2$Cl$_2$ is added at 0° C., 58 mg (57–86%) of mCPBA. The mixture is stirred at 0° C. for 1 h. and is quenched with 15 ml of 10% NaHCO$_3$. The aqueous layer was extracted with 3×15 ml of EtOAc. The combined organic layers are dried over MgSO$_4$, filtered and concentrated to give a crude product. Purification on silica gel prep. TLC affords 36 mg (80%) of free base of compound number 94. The HCl salt is prepared by dissolving the free base in EtOAc and adding HCl-ether solution. After evaporating the solvent, the salts are collected as powder.

(M+H)$^+$ Cal: 561.2423; Found: 561.2416.

Following is a table of the above-exemplefied compounds and other compounds produced in a like manner.

TABLE OF COMPOUNDS

| COMPOUND NO. | STRUCTURE |
|---|---|
| 1 | 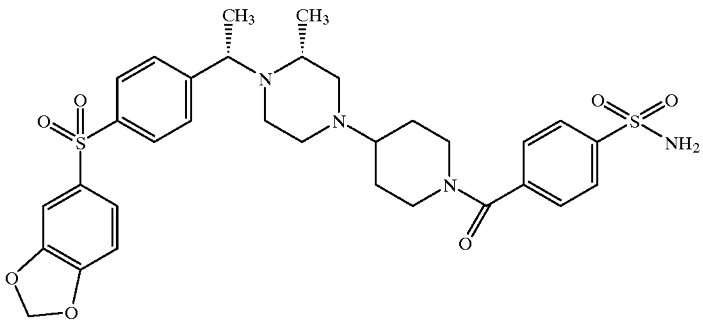 |
| 2 | 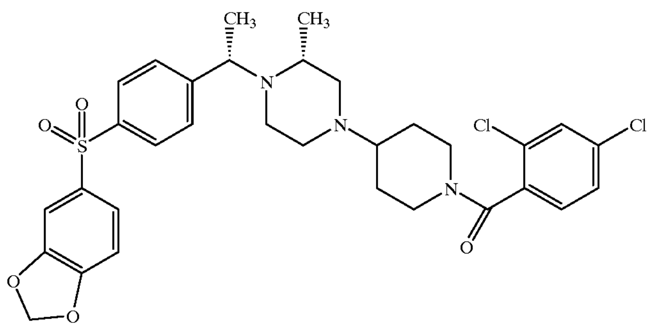 |
| 3 | 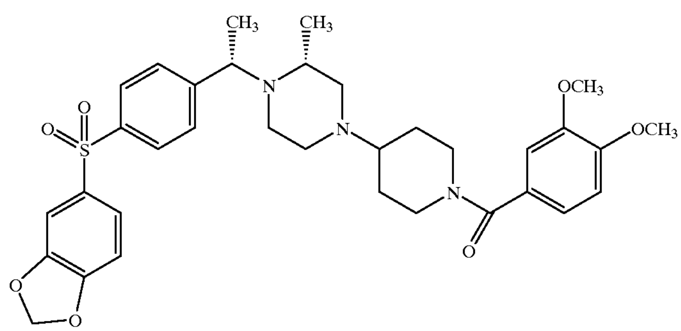 |
| 4 | 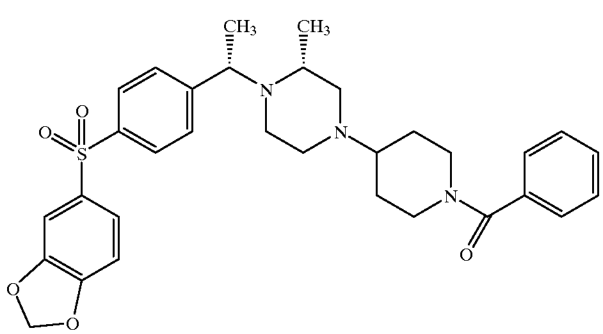 |

-continued
TABLE OF COMPOUNDS
| COMPOUND NO. | STRUCTURE |
|---|---|
| 5 | 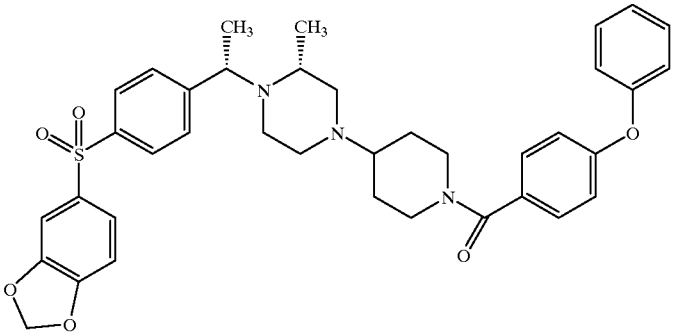 |
| 6 | 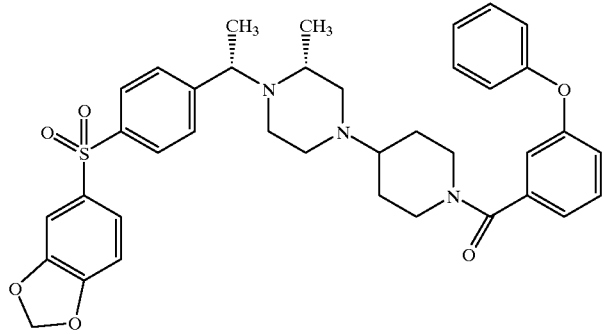 |
| 7 | 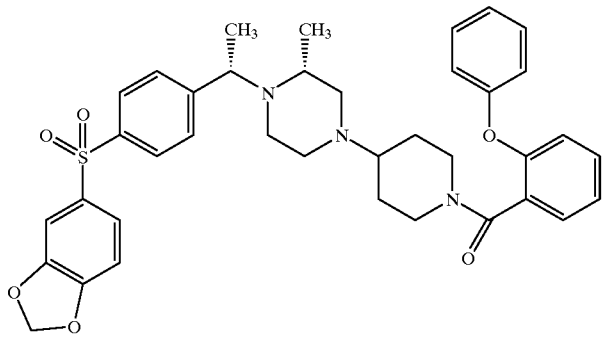 |
| 8 | 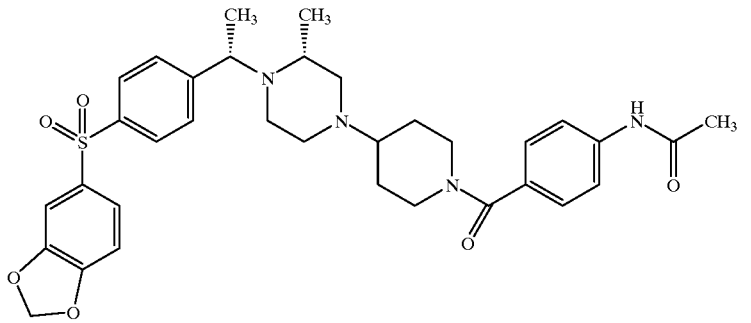 |

-continued
TABLE OF COMPOUNDS
| COMPOUND NO. | STRUCTURE |
|---|---|
| 9 | 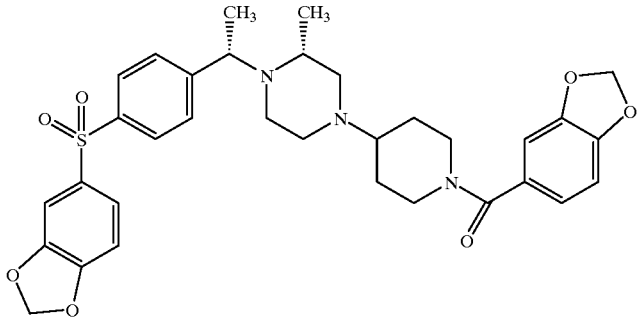 |
| 10 | 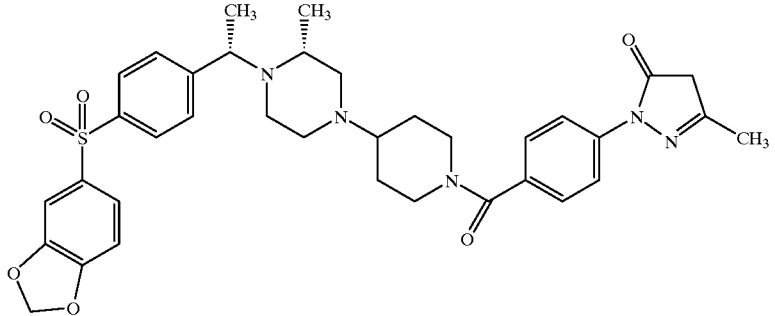 |
| 11 | 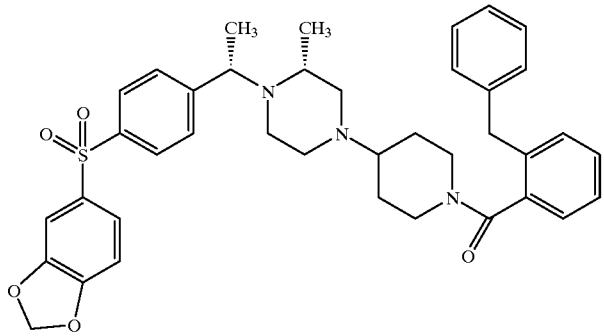 |
| 12 | 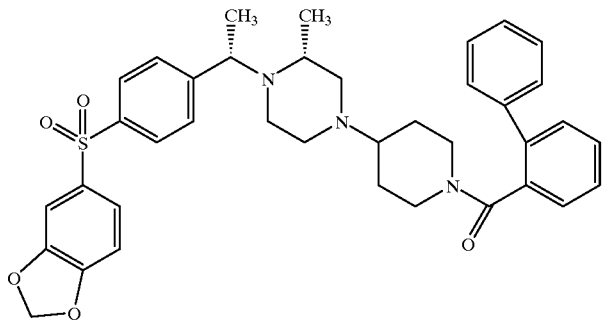 |

-continued
TABLE OF COMPOUNDS
| COMPOUND NO. | STRUCTURE |
|---|---|
| 13 | 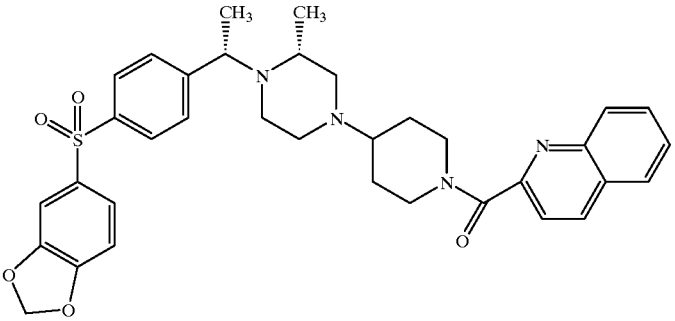 |
| 14 | 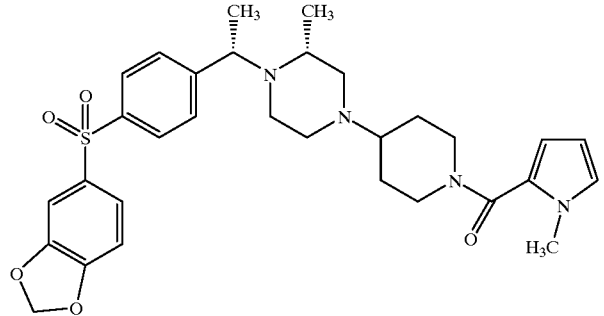 |
| 15 | 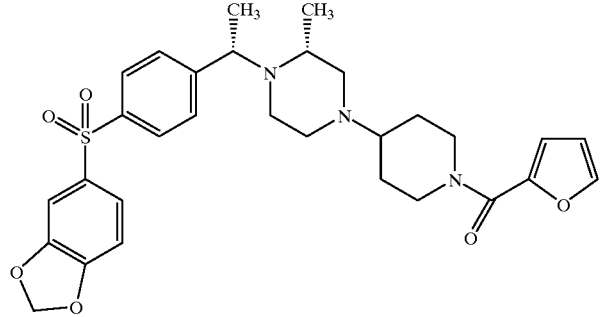 |
| 16 | 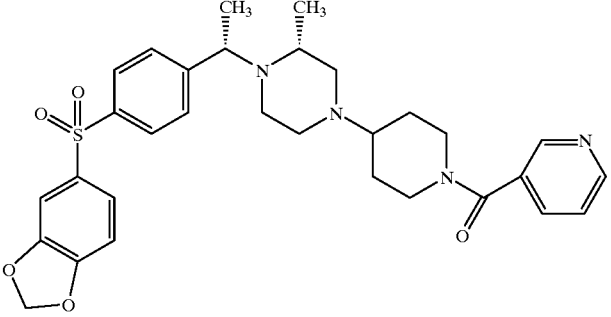 |

-continued

TABLE OF COMPOUNDS

| COMPOUND NO. | STRUCTURE |
|---|---|
| 17 | *(structure)* |
| 18 | *(structure)* |
| 19 | *(structure)* |
| 20 | *(structure)* |

-continued
TABLE OF COMPOUNDS
| COMPOUND NO. | STRUCTURE |
|---|---|
| 21 | 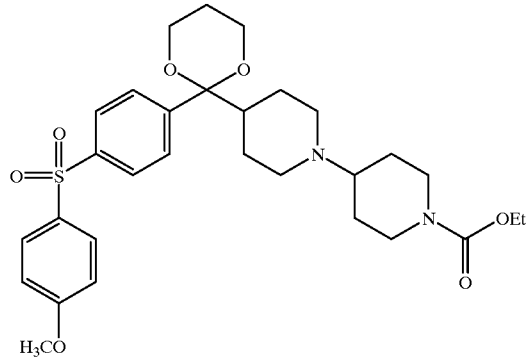 |
| 22 | 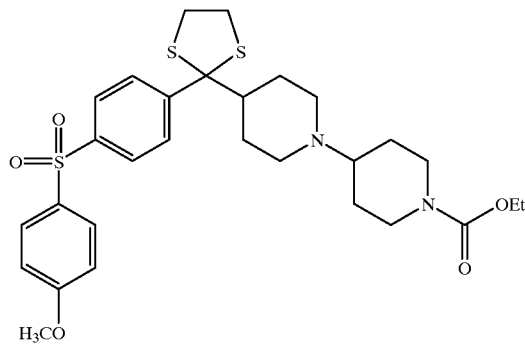 |
| 23 | 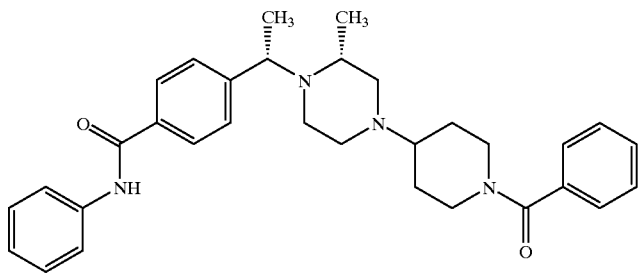 |
| 24 | 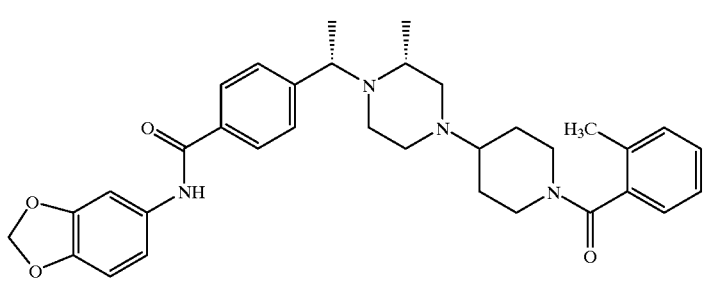 |

-continued

TABLE OF COMPOUNDS

| COMPOUND NO. | STRUCTURE |
|---|---|
| 25 | 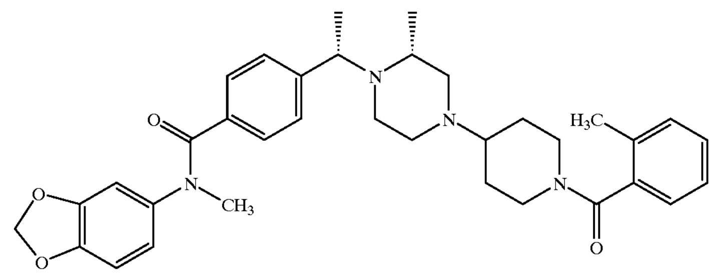 |
| 26 | 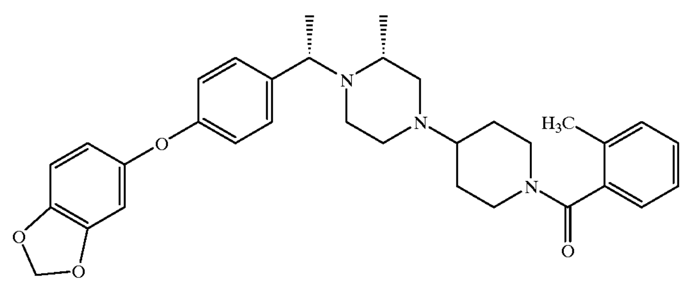 |
| 27 | 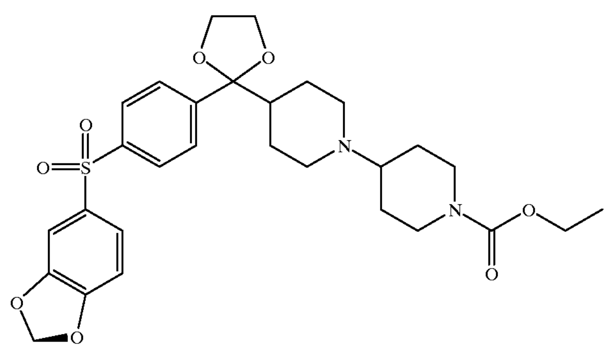 |
| 28 | 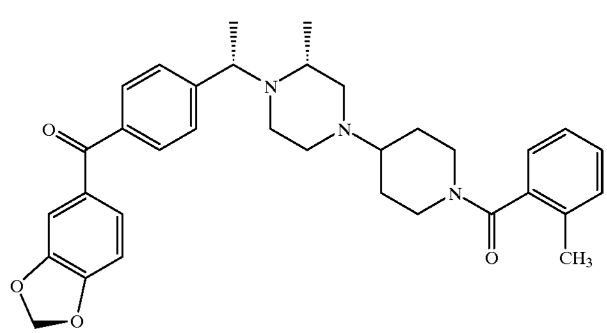 |

-continued

TABLE OF COMPOUNDS

| COMPOUND NO. | STRUCTURE |
|---|---|
| 29 | 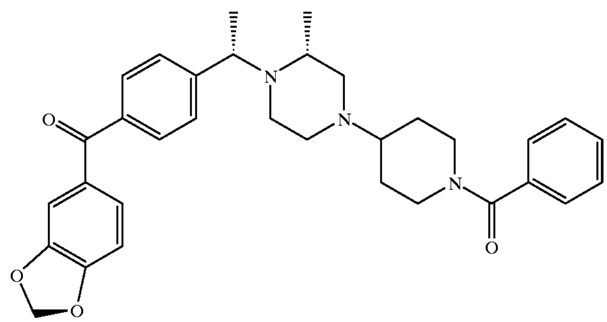 |
| 30 | 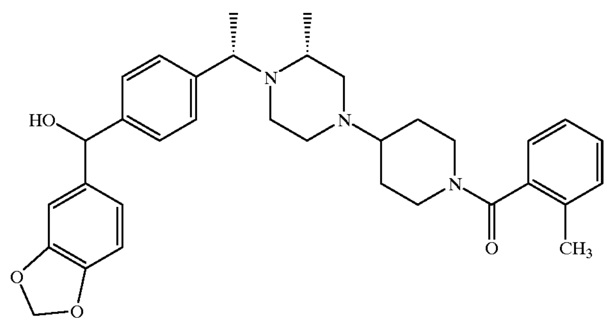 |
| 31 | 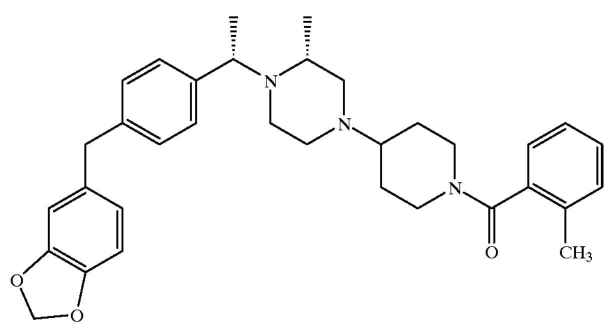 |
| 32 | 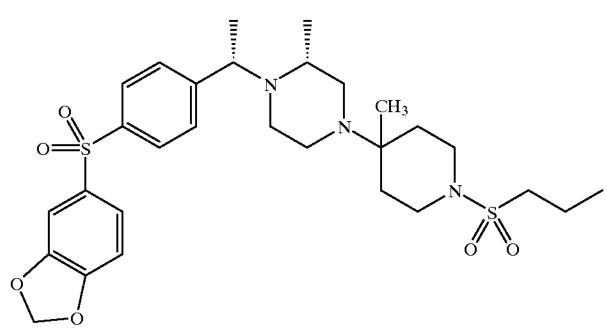 |

-continued

TABLE OF COMPOUNDS

| COMPOUND NO. | STRUCTURE |
|---|---|
| 33 | 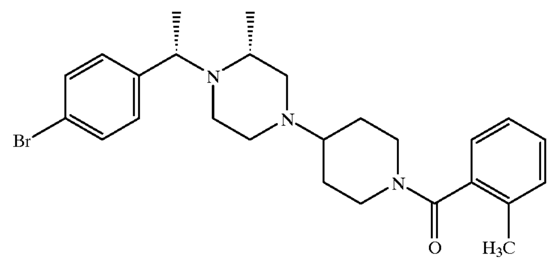 |
| 34 | 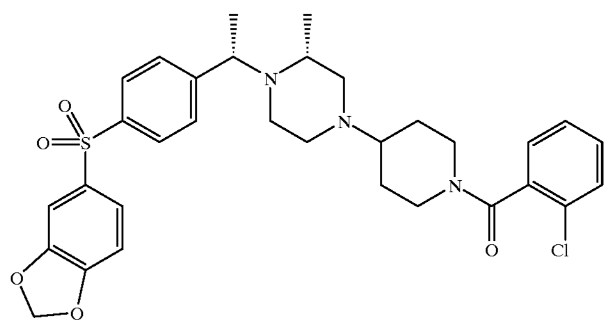 |
| 35 | 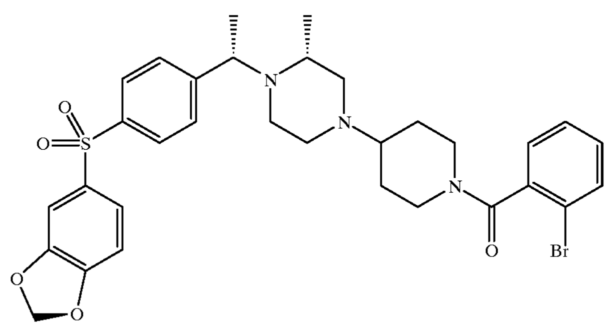 |
| 36 | 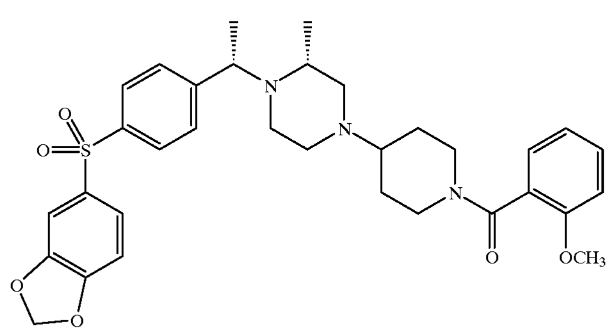 |

-continued
TABLE OF COMPOUNDS
| COMPOUND NO. | STRUCTURE |
|---|---|
| 37 | 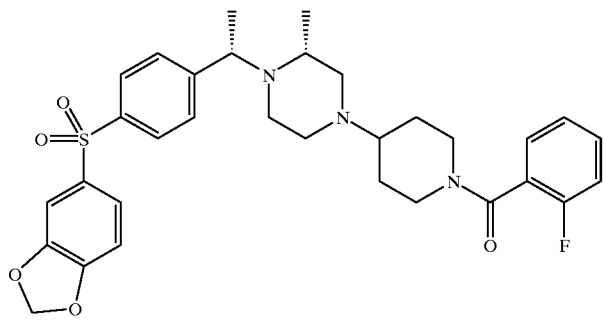 |
| 38 | 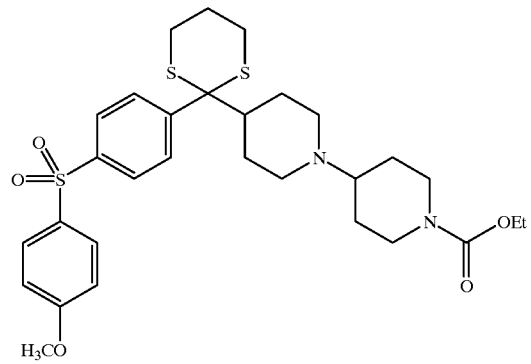 |
| 39 | 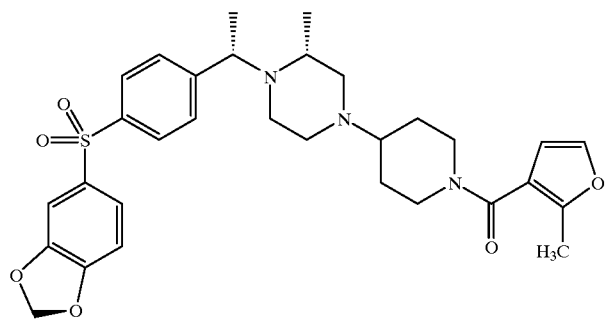 |
| 40 | 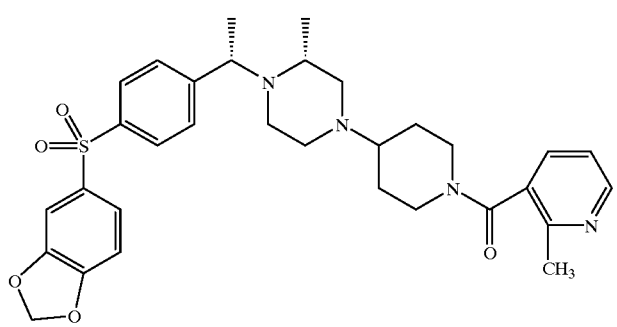 |

-continued
TABLE OF COMPOUNDS
| COMPOUND NO. | STRUCTURE |
|---|---|
| 41 | 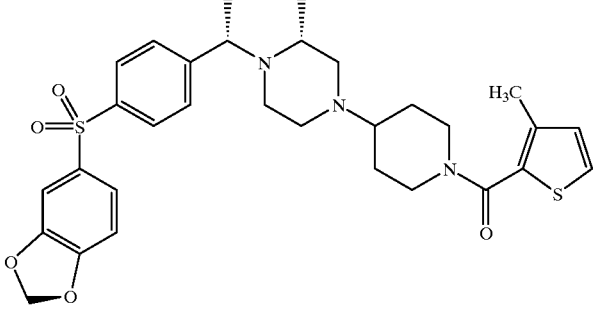 |
| 42 | 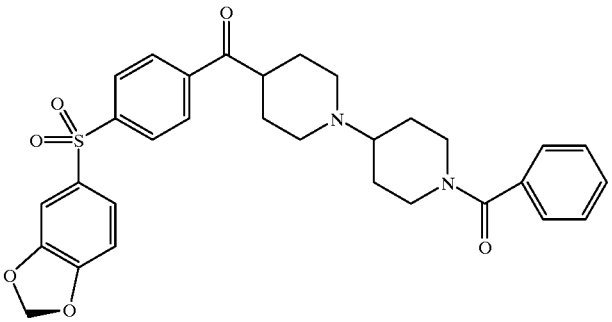 |
| 43 | 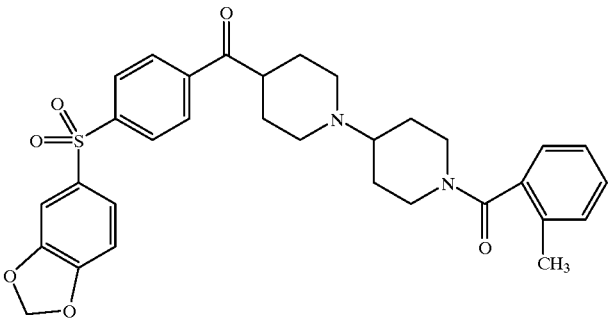 |
| 44 | 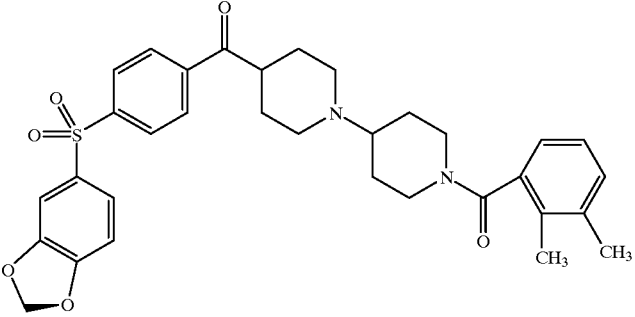 |

-continued

TABLE OF COMPOUNDS

| COMPOUND NO. | STRUCTURE |
|---|---|
| 45 | 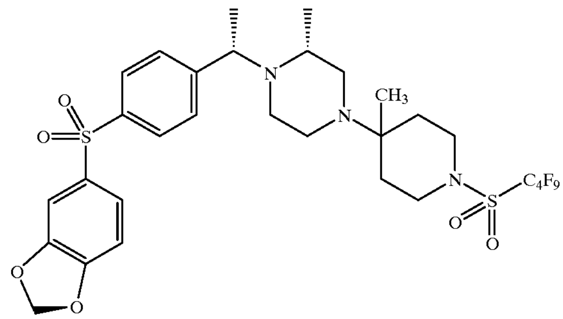 |
| 46 | 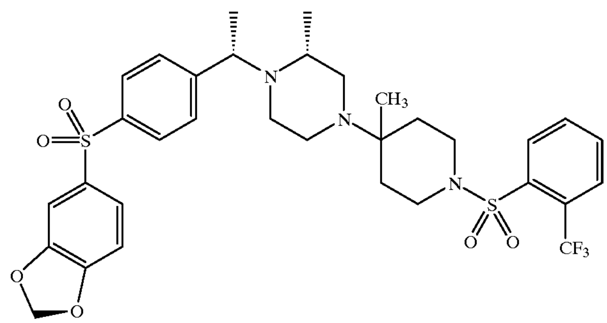 |
| 47 | 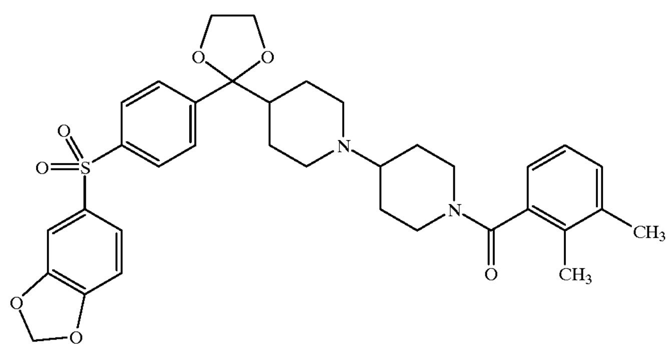 |
| 48 | 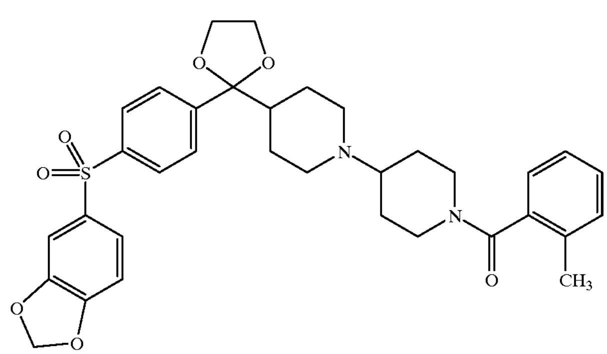 |

-continued

TABLE OF COMPOUNDS

| COMPOUND NO. | STRUCTURE |
|---|---|
| 49 | 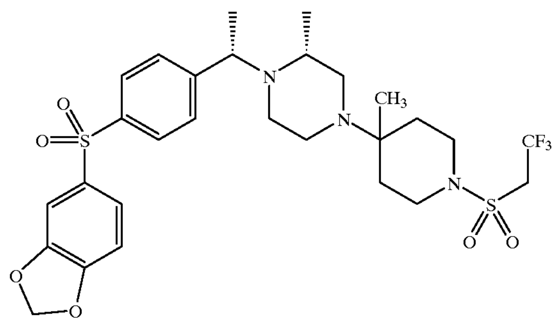 |
| 50 | 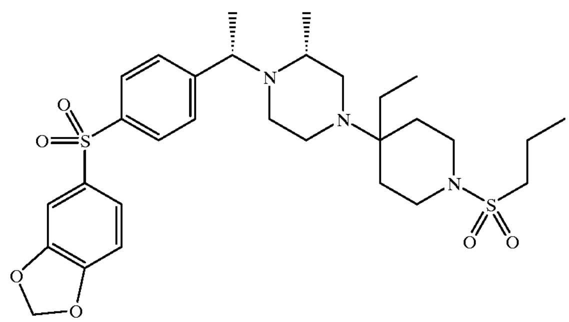 |
| 51 | 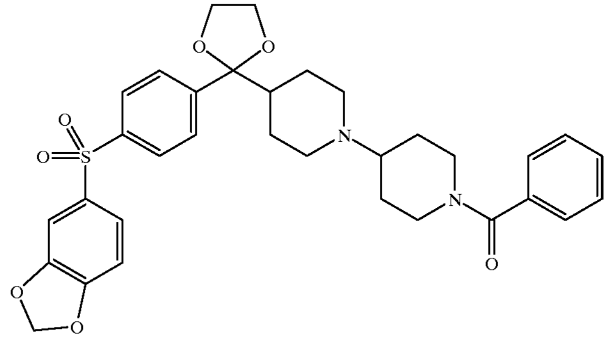 |
| 52 | 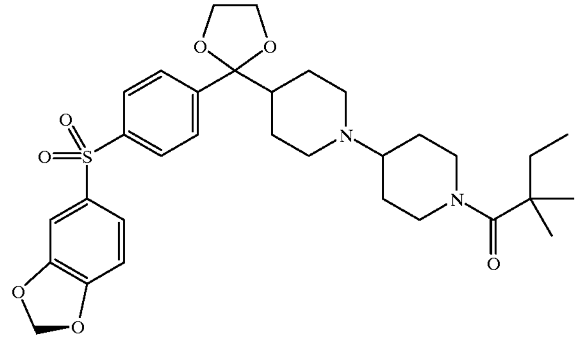 |

-continued

TABLE OF COMPOUNDS

| COMPOUND NO. | STRUCTURE |
| --- | --- |
| 53 | 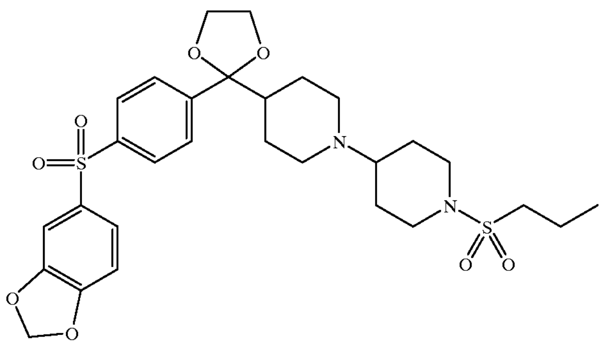 |
| 54 | 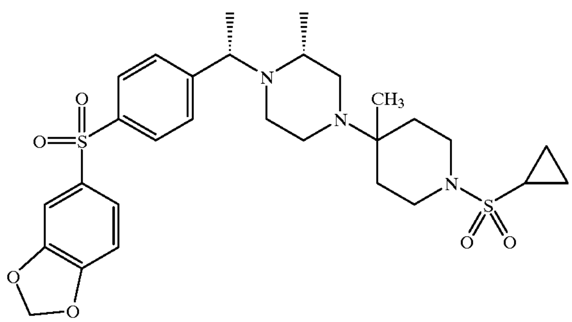 |
| 55 | 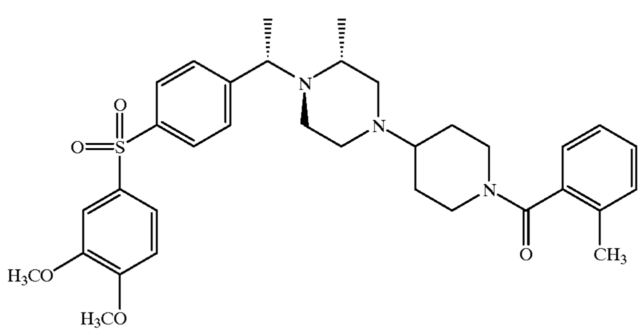 |
| 56 | 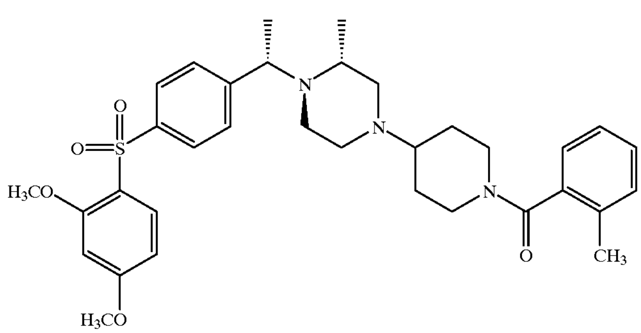 |

-continued

TABLE OF COMPOUNDS

| COMPOUND NO. | STRUCTURE |
| --- | --- |
| 57 | 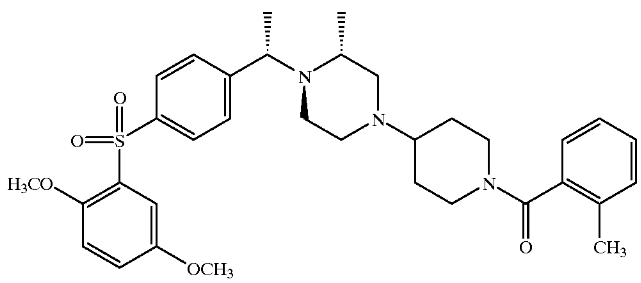 |
| 58 | 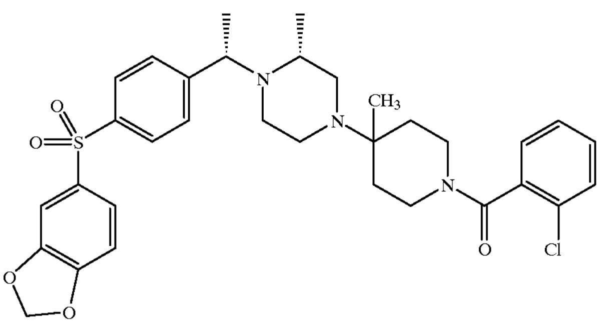 |
| 59 | 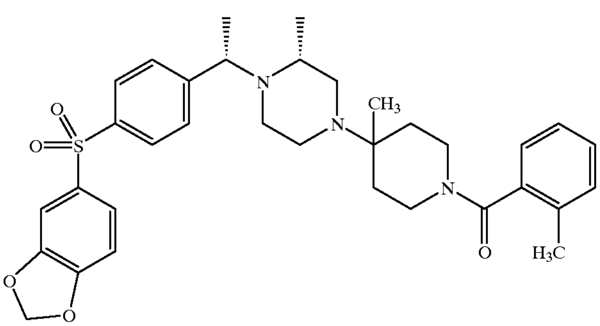 |
| 60 | 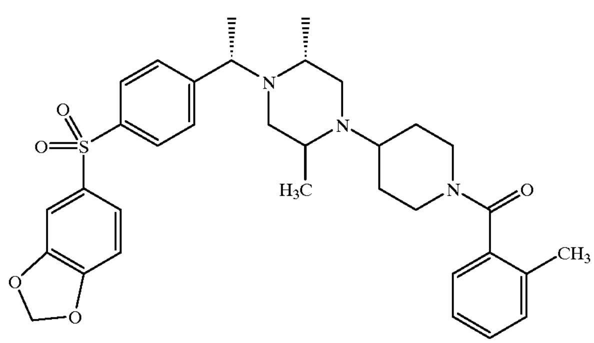 |

-continued
TABLE OF COMPOUNDS
| COMPOUND NO. | STRUCTURE |
|---|---|
| 61 | 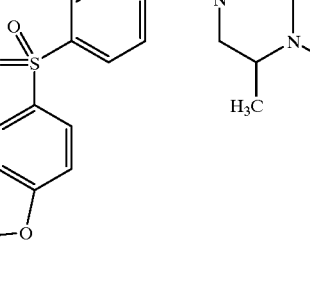 |
| 62 | 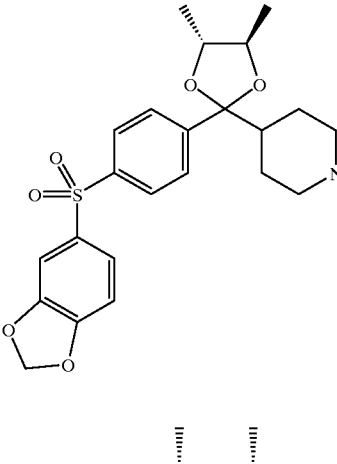 |
| 63 | 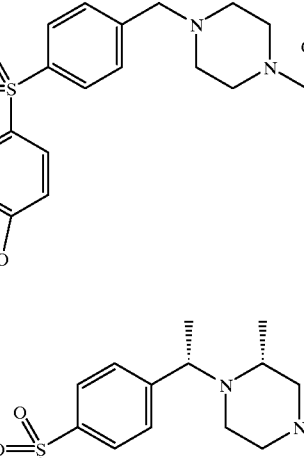 |
| 64 | 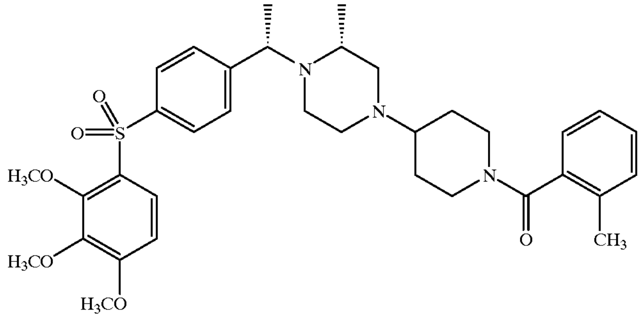 |

-continued

TABLE OF COMPOUNDS

| COMPOUND NO. | STRUCTURE |
|---|---|
| 65 | 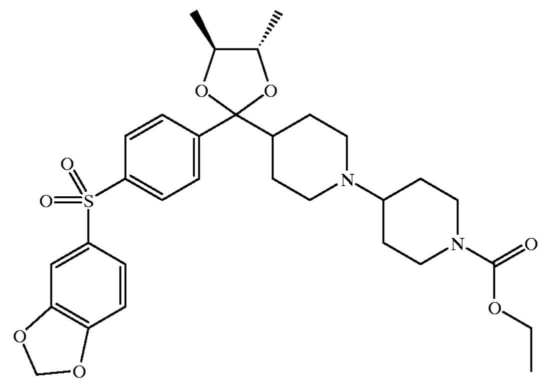 |
| 66 | 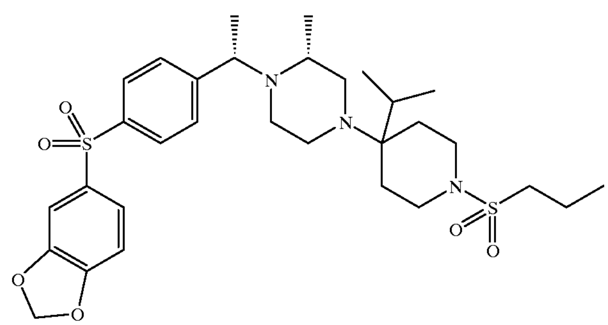 |
| 67 | 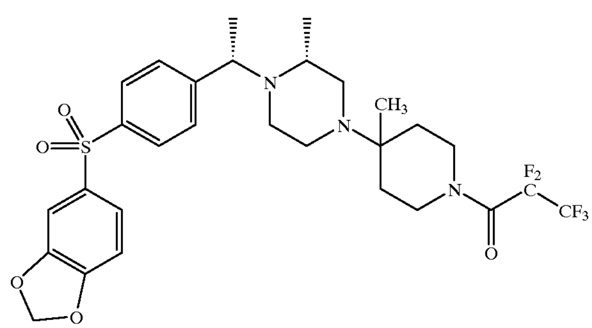 |
| 68 | 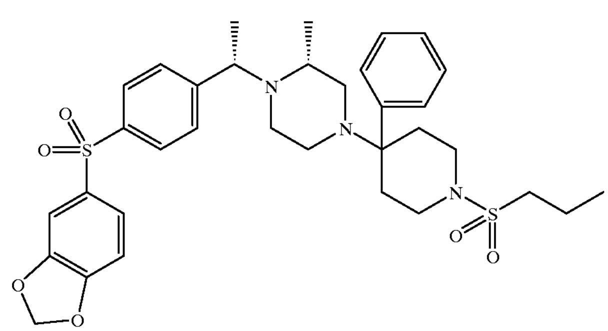 |

TABLE OF COMPOUNDS
| COMPOUND NO. | STRUCTURE |
|---|---|
| 69 | 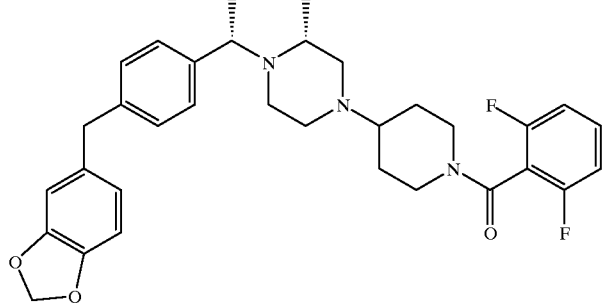 |
| 70 | 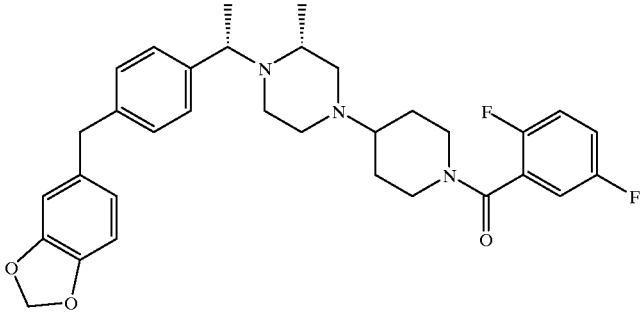 |
| 71 | 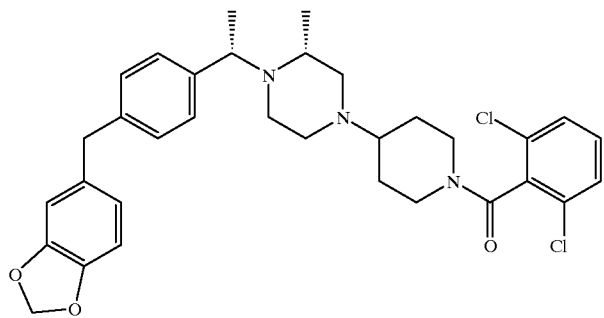 |
| 72 | 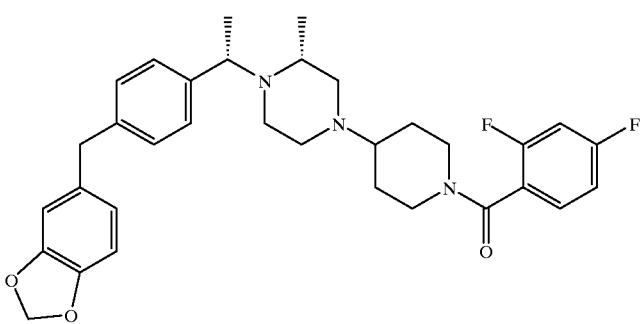 |

-continued
TABLE OF COMPOUNDS
| COMPOUND NO. | STRUCTURE |
|---|---|
| 73 | 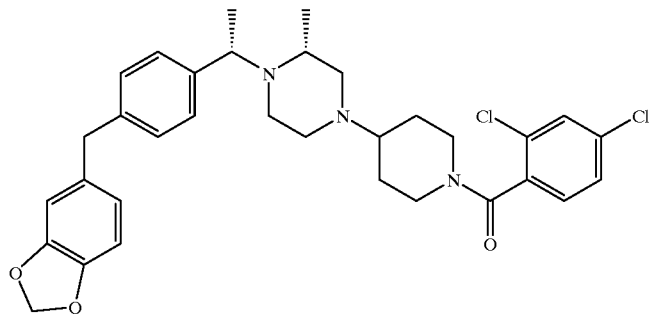 |
| 74 | 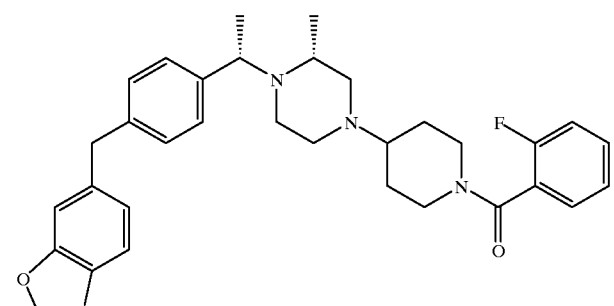 |
| 75 | 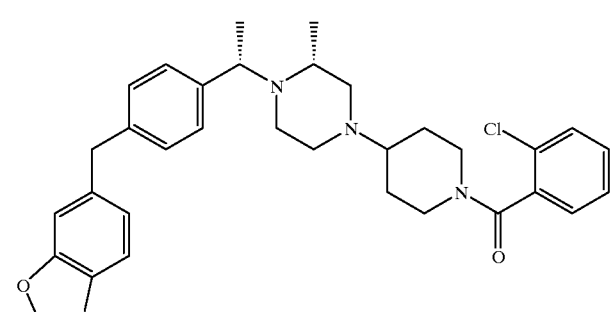 |
| 76 | 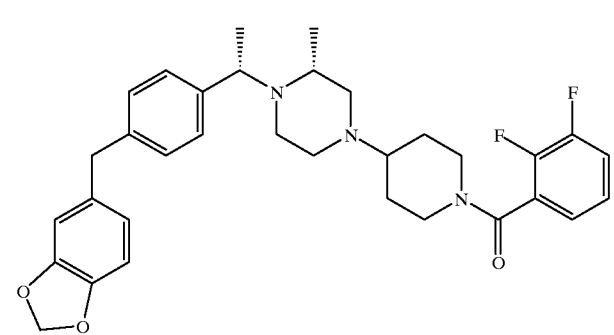 |

-continued

TABLE OF COMPOUNDS

| COMPOUND NO. | STRUCTURE |
|---|---|
| 77 | 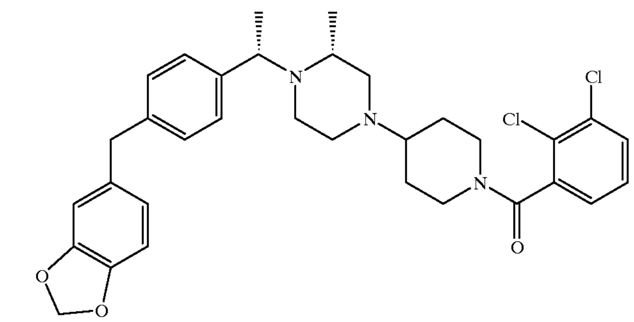 |
| 78 | 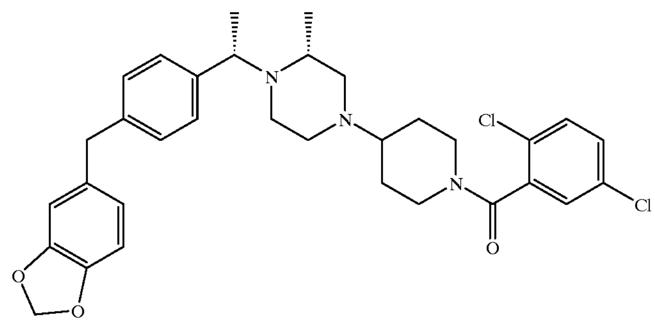 |
| 79 | 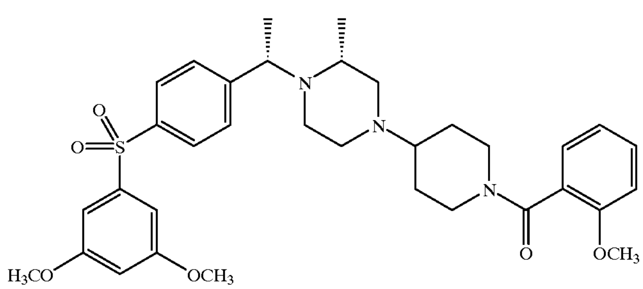 |
| 80 | 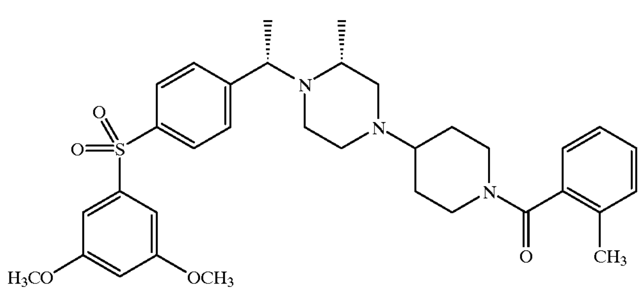 |

-continued

TABLE OF COMPOUNDS

| COMPOUND NO. | STRUCTURE |
|---|---|
| 81 | 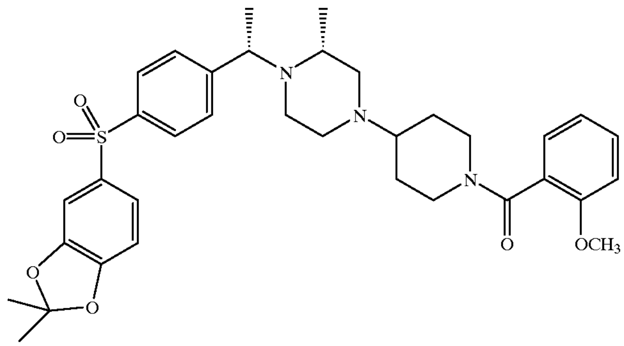 |
| 82 | 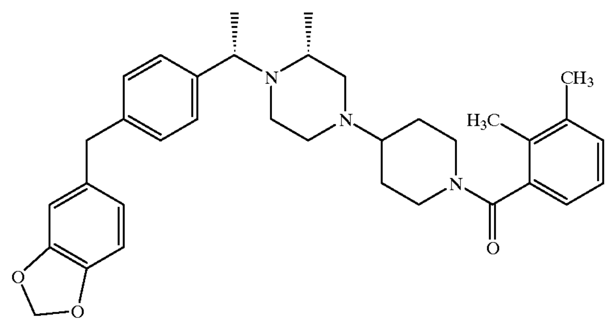 |
| 83 | 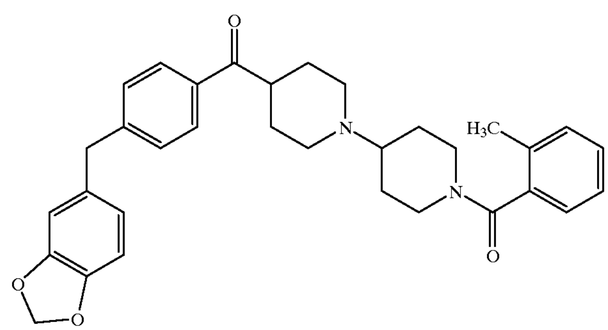 |
| 84 | 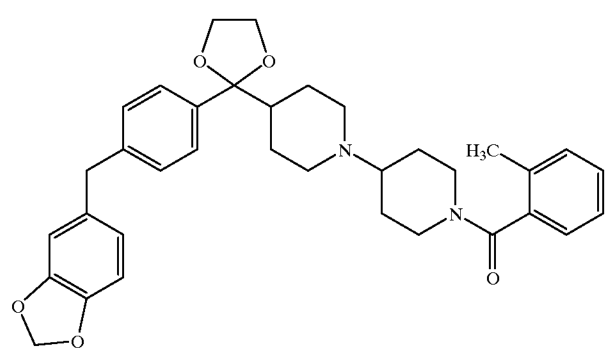 |

TABLE OF COMPOUNDS

| COMPOUND NO. | STRUCTURE |
|---|---|
| 85 | 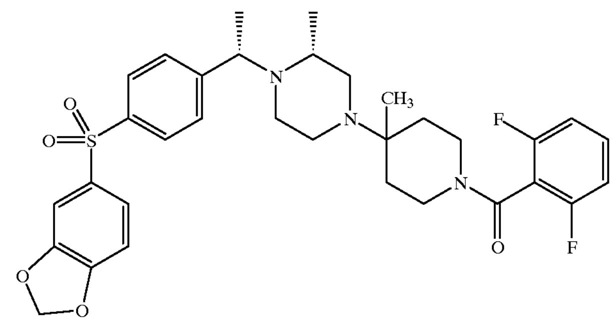 |
| 86 | 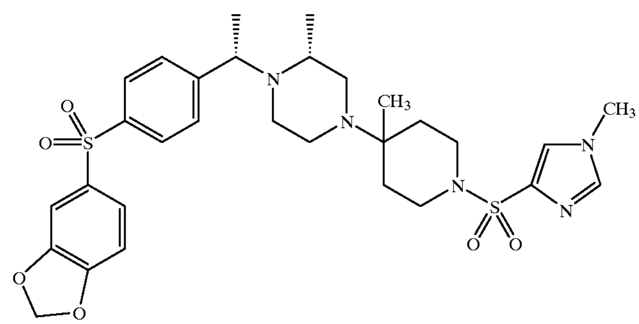 |
| 87 | 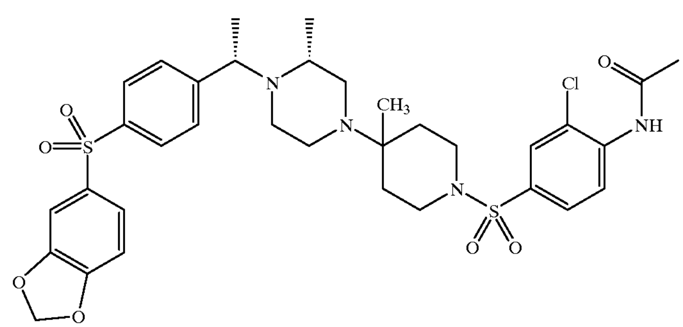 |
| 88 | 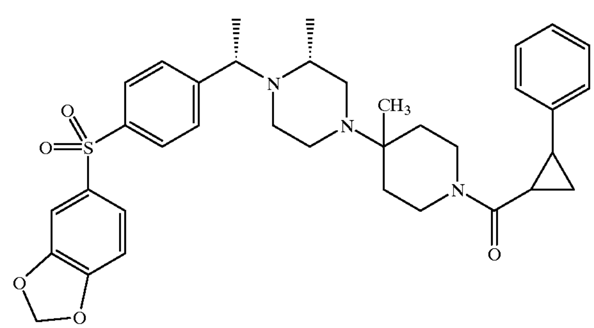 |

-continued
TABLE OF COMPOUNDS
| COMPOUND NO. | STRUCTURE |
|---|---|
| 89 | 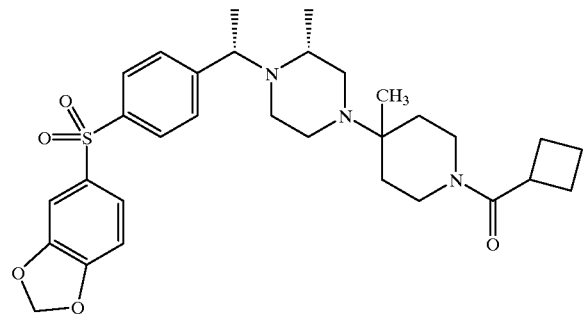 |
| 90 | 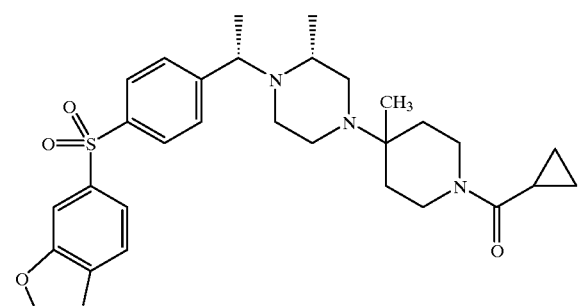 |
| 91 | 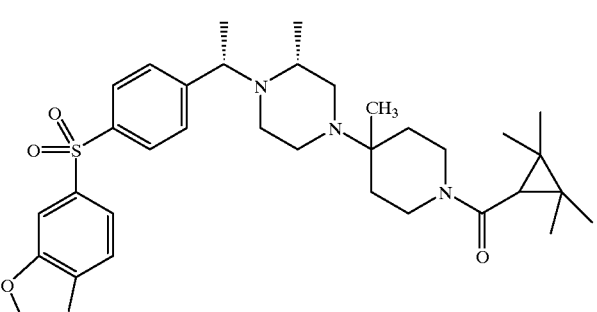 |
| 92 | 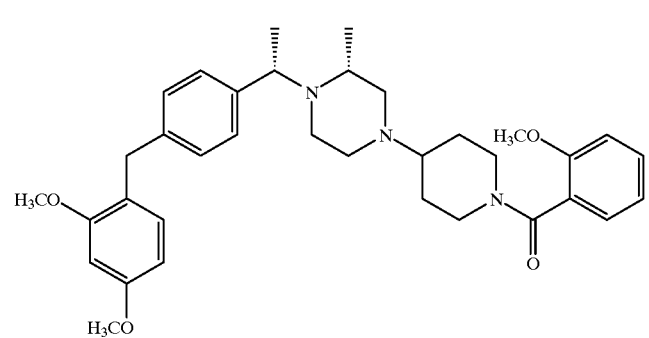 |

-continued

TABLE OF COMPOUNDS

| COMPOUND NO. | STRUCTURE |
| --- | --- |
| 93 | 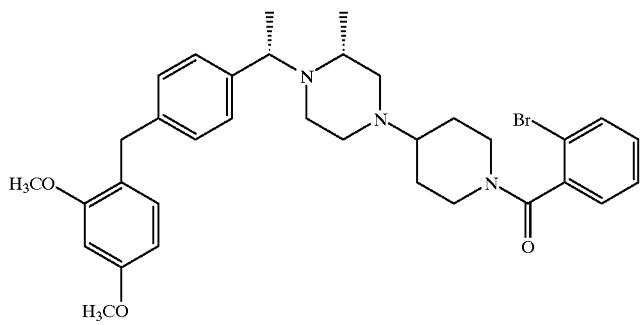 |
| 94 | 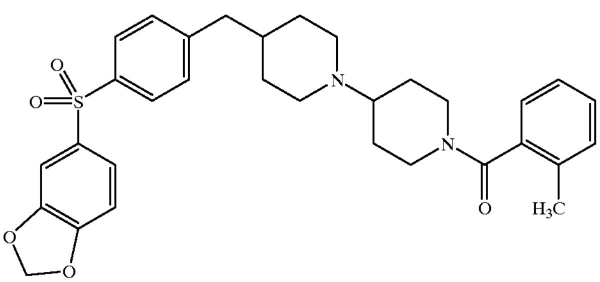 |
| 95 | 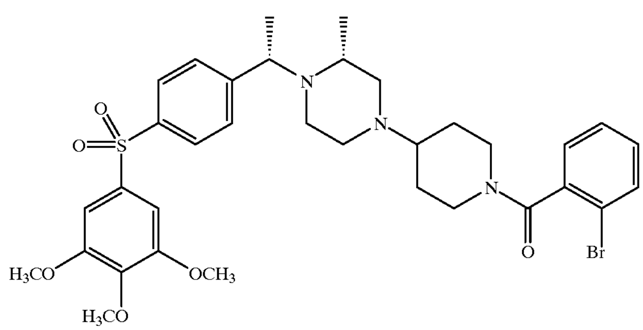 |
| 96 | 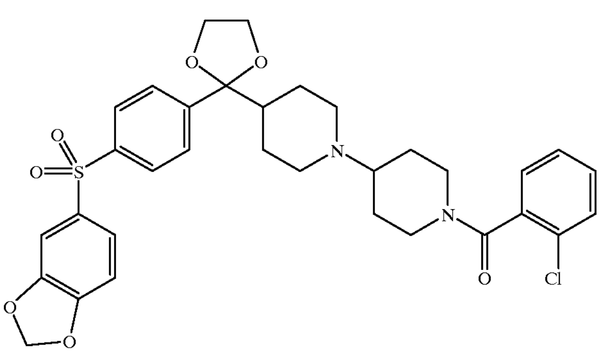 |

TABLE OF COMPOUNDS
| COMPOUND NO. | STRUCTURE |
|---|---|
| 97 | 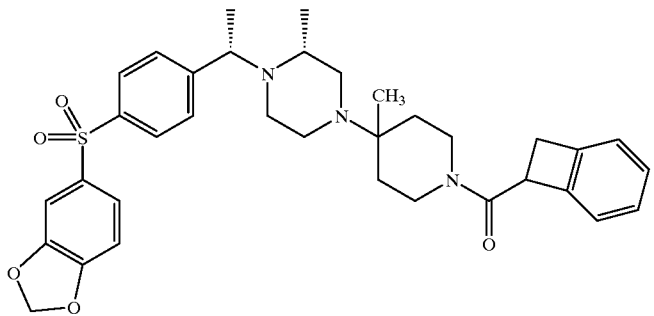 |
| 98 | 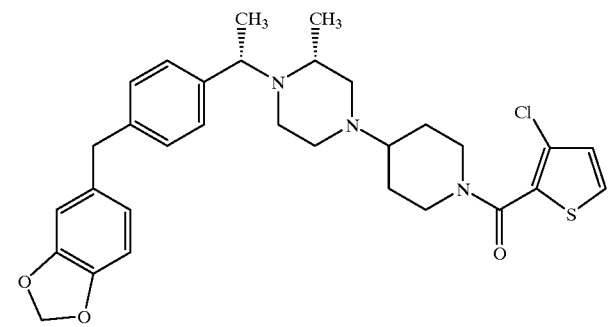 |
| 99 | 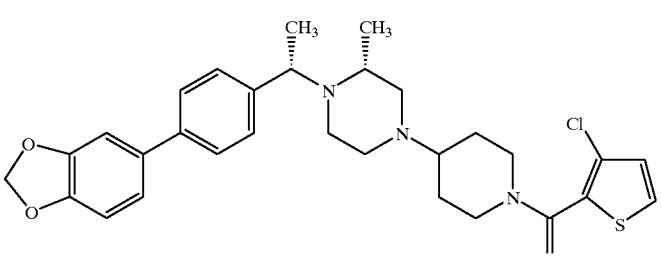 |
| 100 | 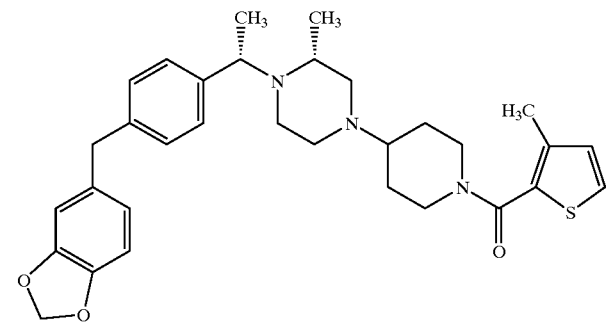 |

-continued

TABLE OF COMPOUNDS

| COMPOUND NO. | STRUCTURE |
|---|---|
| 101 | 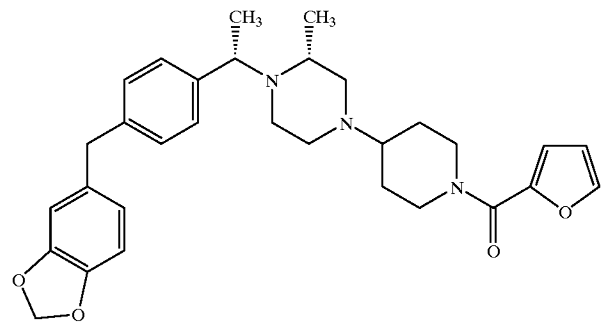 |
| 102 | 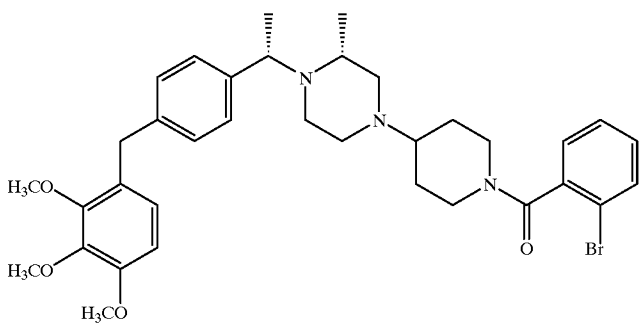 |
| 103 | 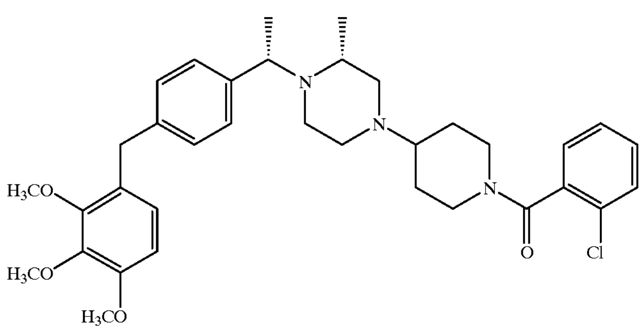 |
| 104 | 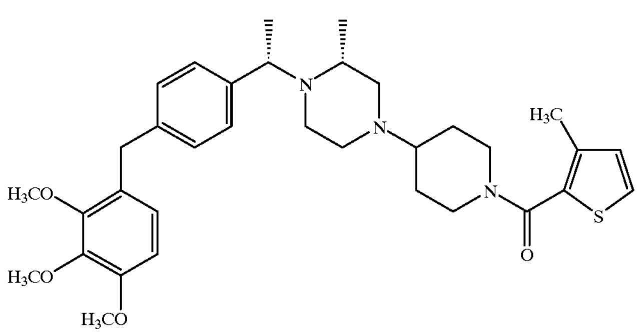 |

-continued

TABLE OF COMPOUNDS

| COMPOUND NO. | STRUCTURE |
| --- | --- |
| 105 | (3,4,5-trimethoxybenzyl-phenyl)-(methyl)-[(2-methyl)piperazinyl]-piperidinyl-(3-methylthiophene-2-carbonyl) structure |
| 106 | (3,4,5-trimethoxybenzyl-phenyl)-(methyl)-[(2-methyl)piperazinyl]-piperidinyl-(2-chlorobenzoyl) structure |
| 107 | (3,4,5-trimethoxybenzyl-phenyl)-(methyl)-[(2-methyl)piperazinyl]-piperidinyl-(2-bromobenzoyl) structure |
| 108 | (3,4-methylenedioxybenzyl-phenyl)-(methyl)-[(2-methyl)piperazinyl]-piperidinyl-(2-bromobenzoyl) structure |

-continued
TABLE OF COMPOUNDS
| COMPOUND NO. | STRUCTURE |
|---|---|
| 109 | 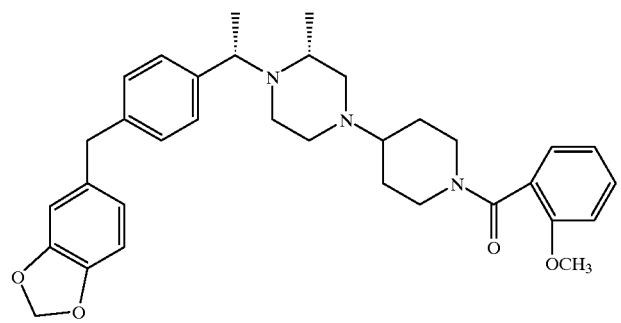 |
| 110 | 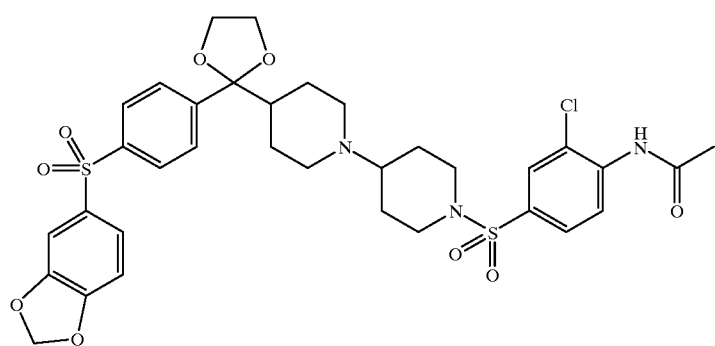 |
| 111 | 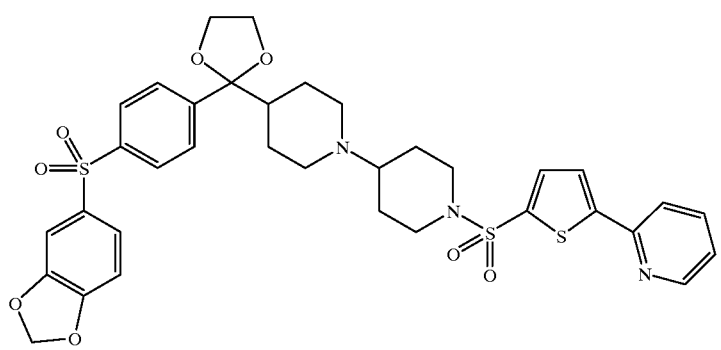 |
| 112 | 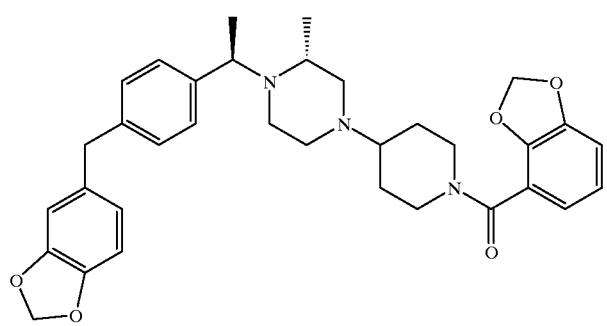 |

TABLE OF COMPOUNDS -continued

| COMPOUND NO. | STRUCTURE |
|---|---|
| 113 | (structure) |
| 114 | (structure) |
| 115 | (structure) |

| Compound No. | Physical data |
|---|---|
| 4 | mp = 215–225 oC (dec)<br>MS MH+ = 574 |
| 17 | mp = 182–190 oC (dec)<br>MS MH+ = 588 |
| 22 | LRMS (FAB)<br>Calc. for C29H3805N253 (M + H): 591<br>Found: 591 |
| 24 | mp = 220–230 oC (dec)<br>MS MH+ = 569 |
| 25 | mp = 190–200 oC (dec)<br>MS MH+ = 583 |
| 27 | HRMS<br>Calcd: 573.2278<br>Found: 573.2271 |
| 28 | mp = 200–210 oC (dec)<br>MSMH+ = 554 |
| 30 | mp = 85–95 oC (dec)<br>MS MH+ = 556 |
| 31 | mp = 210–215 oC (dec)<br>MS MH+ = 540 |
| 32 | mp = 235–237 (dec) |
| 34 | mp = 185–200 oC (dec)<br>MH + 608/610 |
| 35 | mp = 178–190 oC (dec)<br>MS MH+ = 652/654 |
| 36 | mp = 180–190 oC (dec)<br>MH+ = 604 |
| 37 | mp = 180–195 oC (dec)<br>MH+ = 593 |
| 39 | mp = 190–205 oC (dec)<br>MS MH+ = 5787 |
| 41 | mp = 180–290 oC (dec) |

-continued

| Compound No. | Physical data |
|---|---|
| | MS MH+ = 594 |
| 43 | HRMS Calcd 575.2216 |
| | Found 575.2223 |
| 44 | HRMS Calcd 589.2372 |
| | Found 589.2379 |
| 45 | mp = 255–257 (dec) |
| 46 | FAB MH+ = 694 |
| 49 | FAB MH+ = 632 |
| 50 | mp = 195–200 (dec) |
| 53 | LRMS (FAB) |
| | Calc. for C29H38O8N2S2 (M + H): 606 |
| | Found: 606 |
| 54 | FAB (NBA-G/TG-DMSO): 590 (M+), 574, 406, 389 |
| 55 | HRMS calcd 594.2672 |
| | found 594.2668 |
| 56 | HRMS calcd 642.2686 |
| | found 642.2685 |
| 57 | HRMS calcd 606.3002 |
| | found 606.2987 |
| 58 | mp = 218–220 (dec) |
| 59 | mp = 203–205 (dec) |
| 62 | LRMS (FAB) |
| | Calc. for C31H40O8N2S (M + H): 601 |
| | Found: 601 |
| 63 | FAB MH+ = 682 |
| 64 | HRMS calcd 636.3107 |
| | found 636.3119 |
| 66 | mp = 157–160 (dec) |
| 67 | FAB MH+ = 632 |
| 68 | mp = 172–175 (dec) |
| 79 | HRMS calcd 622.2951 |
| | found 622.2932 |
| 80 | HRMS calcd 606.3002 |
| | found 606.2999 |
| 81 | HRMS calcd 634.2952 |
| | found 634.2962 |
| 82 | mp: 207–212 oC, with decomposition. |
| | Mass spectrum: MH+ = 554 |
| 84 | HRMS Calcd 579.3015 |
| | Found 569.3022 |
| 85 | mp = 242–245 (dec) |
| 86 | mp = 206–209 (dec) |
| 87 | mp = 237–239 (dec) |
| 88 | FAB (SIMS): 630 (M+), 391, 329, 307, 289 |
| 89 | FAB (SIMS): 568 (M+), 391, 307, 232 |
| 90 | FAB (NBA-G/TG-DMSO): 554 (M+), 538, 389, 289 |
| 91 | FAB (NBA-G/TG-DMSO): 610 (M+), 594, 490, 426, 322 |
| 92 | HRMS calcd 572.3488 |
| | found 572.3491 |
| 93 | HRMS calcd 620.2488 |
| | found 620.2478 |
| 94 | HRMS Calcd 561.2323 |
| | Found 561.2423 |
| 95 | HRMS calcd 700.2056 |
| | found 700.2044 |
| 96 | LRMS (FAB) |
| | Calc. for C33H35O7N25Cl (M + H): 639 |
| | Found: 639 |
| 97 | FAB (NBA–G/TG–DMSO): 616 (M+), 432, 389, 328 |
| 100 | mp: 210–220 oC, with decomposition. |
| | Mass spectrum: MH+ = 546. |
| 102 | HRMS calcd 650.2593 |
| | found 650.2588 |
| 103 | HRMS calcd 606.3099 |
| | found 606.3084 |
| 104 | HRMS calcd 592.3209 |
| | found 592.3215 |
| 105 | HRMS calcd 592.3209 |
| | found 592.3215 |
| 106 | HRMS calcd 606.3099 |
| | found 606.3090 |
| 107 | HRMS calcd 650.2593 |
| | found 650.2579 |
| 112 | mp: 190–195 oC, with decomposition. |
| | Mass spectrum: MH+ = 546. |

What is claimed:

1. A compound having the structural formula I,

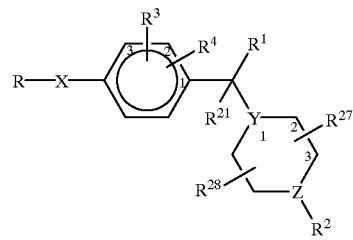

including all isomers and pharmaceutically acceptable salts, esters, and solvates thereof, wherein one of Y and Z is N and the other is CH, or C-alkyl;

X is —O—, —S—, —SO—, —$SO_2$—, —$NR^6$—, —CO—, —$CH_2$—, —CS—, —$C(OR^5)_2$—, —$C(SR^5)_2$—, —$CONR^{20}$—, —C(alkyl)$_2$—, —C(H)(alkyl)-, —$NR^{20}$—$SO_2$—, —$NR^{20}CO$—,

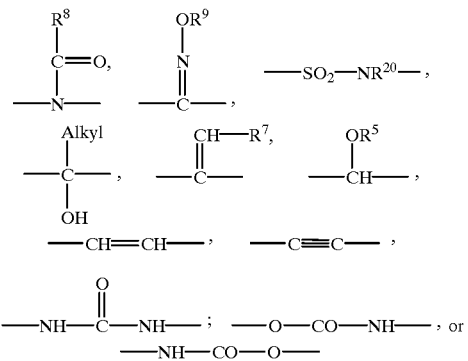

R is

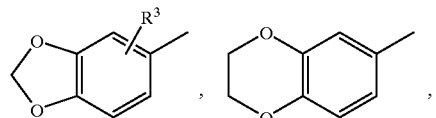

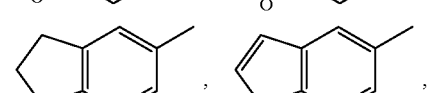

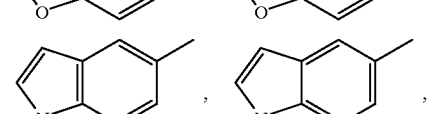

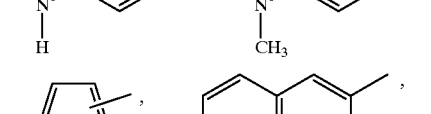

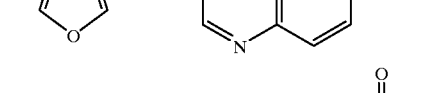

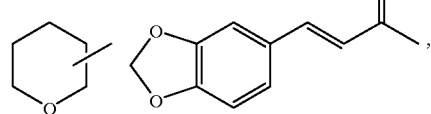

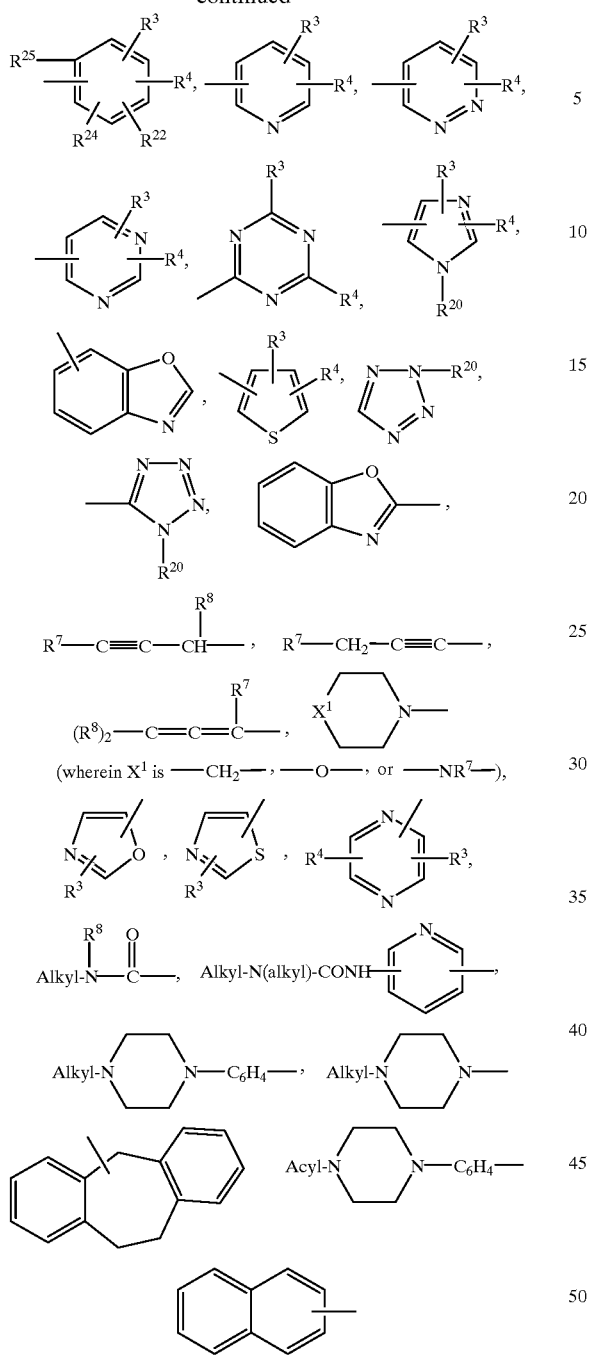

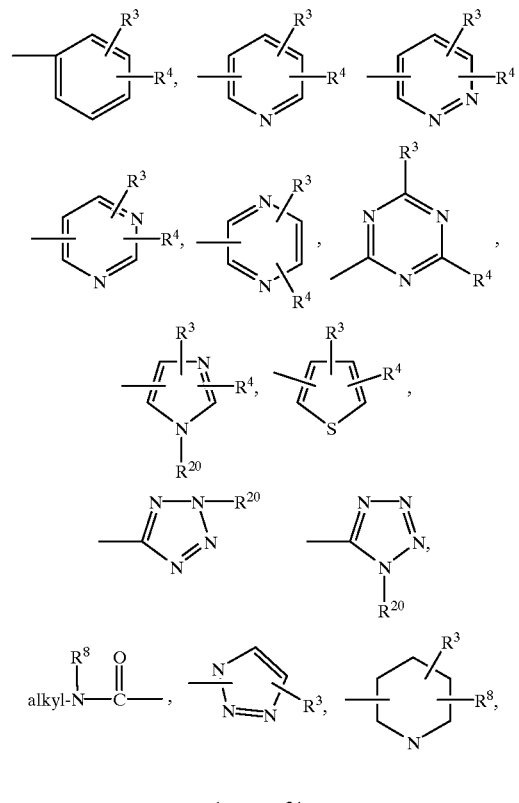

hydrogen, acyl, alkyl, alkenyl, cycloalkyl, cycloalkyl substituted with up to two alkyl groups, cycloalkenyl, bicycloalkyl, arylalkenyl, benzyl, benzyl substituted with up to three independently selected $R^3$ groups, cycloalkylalkyl, polyhaloacyl, benzyloxyalkyl, hydroxy$C_2$-$C_{20}$alkyl, alkenylcarbonyl, alkylarylsulfonyl, alkoxycarbonylaminoacyl, alkylsulfonyl, or arylsulfonyl, additionally, when X is —$CH_2$—, R may also be —OH; in further addition, when X is not N, R may also be hydroxymethyl, in further addition, R and X may combine to form the group Prot-(NOAA)$_r$—NH— wherein r is an integer of 1 to 4, Prot is a nitrogen protecting group and when r is 1, NOAA is a naturally occuring amino acid or an enantiomer thereof, or when r is 2 to 4, each NOAA is an independently selected naturally occuring amino acid or an enantiomer thereof;

$R^1$ and $R^{21}$ are independently selected from the group consisting of H, alkyl, alkenyl, cycloalkyl, cycloalkenyl, bicycloalkyl, alkynyl, cyano, aminoalkyl, alkoxycarbonyl, aminocarbonyl, Hydroxyamidino, alkoxycarbonylalkyl, phenyl alkyl, alkylcarbonlyoxyalkyl, H, —OH, (provided $R^1$ and $R^{21}$ are both not —OH and Y is not N), formyl, —CO alkyl, —COacyl, —COaryl, and hydroxyalkyl; additionally $R^1$ and $R^{21}$ together may form the group =$CH_2$, =N—$OR^5$, =N—CN, =N—N($R^5$)$_2$, =CH-Alkyl, alkylene, =O, $$=\overset{\underset{|}{\text{Alkyl}}}{C}—\text{Alkyl},$$

=C(halo)$_2$, in further addition, $R^1$ and $R^{21}$ together with the carbon atom to which they are attached may form the group

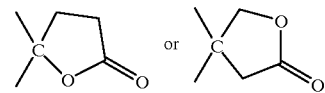

or $R^1$ and $R^{21}$ together with the carbon atom to which they are attached may form a saturated heterocyclic ring containing 3 to 7 carbon atoms, one or more of which may optionally be substituted by alkyl, and one or two groups independently selected from S, O, and N—$R^{20}$;

$R^2$ is

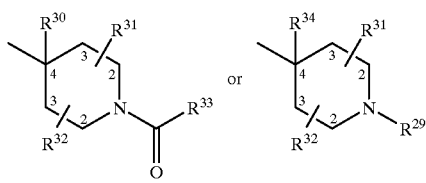

$R^3$, $R^4$, $R^{22}$, $R^{24}$, and $R^{25}$ are independently selected from the group consisting of alkyl, H, halo, alkoxy, benzyloxy, benzyloxy substituted by nitro or aminoalkyl, haloalkyl, polyhaloalkyl, nitro, cyano, sulfonyl, hydroxy, amino, alkylamino, formyl, alkylthio, polyhaloalkoxy, acyloxy, trialkylsilyl, alkylsulfonyl, arylsulfonyl, acyl, alkoxycarbonyl, alkylsulfinyl, —OCONH$_2$, —OCONH-alkyl, alkylaminoalkyl, dialkylaminoalkyl, —COOH, —CON($R^{20}$)$_2$, —OCON(alkyl)$_2$, —NHCOO-alkyl, —NHCO-alkyl, phenyl, hydroxyalkyl, or morpholino;

each $R^5$ and $R^6$ is independently selected from the group consisting of H and alkyl, provided that when X is C(OR$^5$)$_2$ or C(SR$^5$)$_2$, both $R^5$ groups cannot be H, and in addition, when X is C(OR$^5$)$_2$ or C(SR$^5$)$_2$, the two $R^5$ groups in X may be joined to form —(CR$^{20}$$_2$)$_p$— wherein p is an integer of 2 to 4;

$R^7$ is independently selected from the group consisting of H, alkyl, arylalkyl, cycloalkyl, aryl and aryl substituted with $R^3$ and $R^4$ as defined herein;

each $R^8$ is independently selected from the group consisting of H, hydroxyalkyl, or alkyl or two $R^8$ groups may be joined to form an alkylene group;

$R^9$ is H, alkyl, aralkyl, or acyl:

$R^{20}$ is H, aryl or alkyl;

$R^{27}$ and $R^{28}$ are independently selected from the group consisting of H, alkyl, hydroxyalkyl, arylalkyl, aminoalkyl, haloalkyl, thioalkyl, alkylthioalkyl, carboxyalkyl, imidazolylalkyl, and indolylalkyl, additionally $R^{27}$ and $R^{28}$ may combine to form an alkylene group;

$R^{29}$ is H, alkyl, —CO-alkyl, alkoxycarbonyl, aminocarbonyl, aryloxycarbonyl alkylaminocarbonyl, dialkylaminocarbonyl, alkylsulfonyl, or arysulfonyl;

$R^{30}$ is H, alkyl, aryl, cycloalkyl, hydroxyalkyl, aminoalkyl, —COOR$^{20}$, —CON(R$^{20}$)$_2$ or cyano;

$R^{31}$ and $R^{32}$ are the same as $R^{30}$ and in addition, two $R^{30}$, $R^{31}$ and $R^{32}$ groups may form the group —(CH$_2$)$_r$— (wherein r is 1 to 6), in further addition, $R^{31}$ and $R^{32}$ can also be hydroxy, —N(R$^{20}$)$_2$, —O-acyl, —N(R$^{20}$) acyl, —OCOOR$^{20}$, or —OCON(R$^{20}$)$_2$;

$R^{33}$ is aryl or heteroaryl, with the proviso that when $R^{33}$ is heteroaryl, the CO—R$^{33}$ bond is to a carbon atom in the $R^{33}$ group: and $R^{34}$ is alkyl, cycloalkyl or aryl and in addition $R^{34}$ may also be H when $R^1$ and $R^{21}$ together with the carbon atom to which they are attached form a saturated heterocyclic ring containing 3 to 7 carbon atoms and two groups independently selected from S, O, and N—R$^{20}$.

2. A compound of claim 1 wherein Y is CH and Z is N.

3. A compound of claim 1 wherein R is

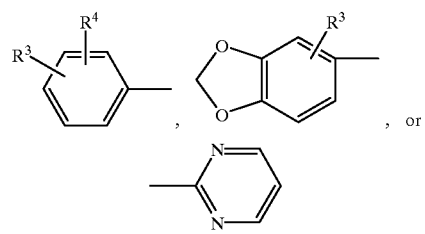

and X is O, SO, SO$_2$, CH$_2$, CH(alkyl), C(alkyl)$_2$, CH(OH), or N(R$^{20}$)CO.

4. A compound of claim 1 wherein X is SO$_2$, CH$_2$, or —(CH$_3$)—CO—.

5. A compound of claim 1 wherein $R^3$ and $R^4$ are H and either $R^1$ is H, cycloalkyl or alkyl and $R^{21}$ is H or $R^1$ and $R^{21}$ together form =O.

6. A compound of claim 5 wherein R is

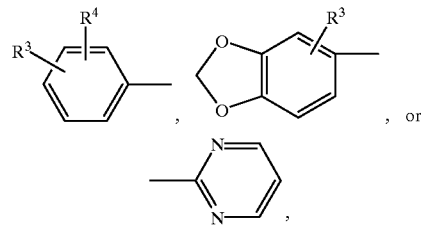

X is O, SO, SO$_2$, CH$_2$, CH(alkyl), C(alkyl)$_2$ or N(R$^{20}$)CO; $R^3$ and $R^4$ are H and either $R^1$ is H, cycloalkyl or alkyl and $R^{21}$ is H or $R^1$ and $R^{21}$ together form =O, or

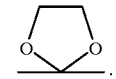

7. A compound of claim 1 wherein at least one of $R^{27}$ and $R^{28}$ is alkyl.

8. A compound of claim 1 wherein one of $R^{27}$ or $R^{28}$ is methyl and the other is hydrogen.

9. A compound of claim 1 wherein R is

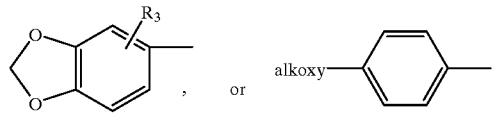

10. A compound of claim 1 wherein $R^2$ is

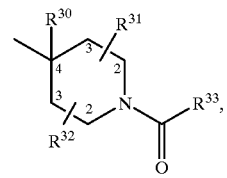

and $R^{30}$ is H or CH$_3$: $R^{31}$ and $R^{32}$ are H: and $R^{33}$ is ortho-substituted aryl or heteroaryl.

11. A compound of claim 10 wherein $R^{33}$ is

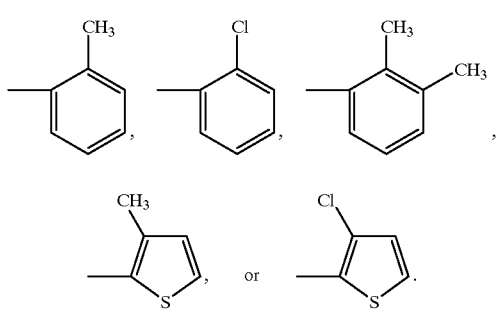

12. A compound of claim 1 wherein $R^2$ is

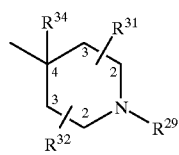

and $R^{34}$ is methyl and $R^{31}$ and $R^{32}$ are H.

13. A compound of claim 1 having the structural formula

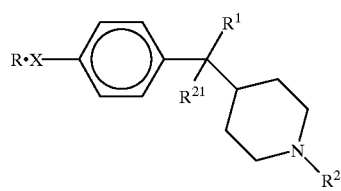

wherein R, X, $R^1$, $R^2$ and $R^{21}$ are as defined in the following table:

| R | X | $R^1$, $R^{21}$ | $R^2$ |
|---|---|---|---|
| H₃CO–C₆H₄– | –SO₂– | dioxolane | 4-piperidinyl-N-C(O)OCH₂CH₃ |
| H₃CO–C₆H₄– | –SO₂– | dioxane | 4-piperidinyl-N-C(O)OCH₂CH₃ |
| H₃CO–C₆H₄– | –SO₂– | dithiolane | 4-piperidinyl-N-C(O)OCH₂CH₃ |
| benzo[1,3]dioxole | –SO₂– | dioxolane | 4-piperidinyl-N-C(O)OCH₂CH₃ |

-continued
| R | X | R¹, R²¹ | R² |
|---|---|---------|-----|
| 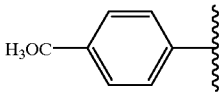 | —SO₂— | 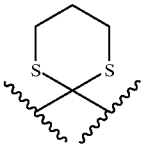 | 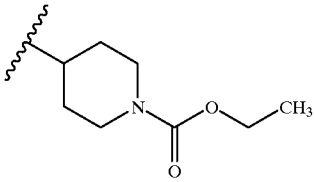 |
| 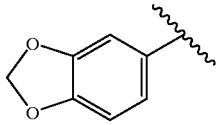 | —SO₂— | —C(O)— | 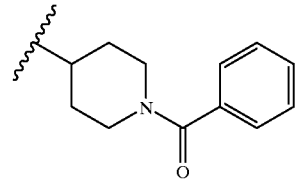 |
| 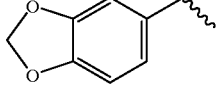 | —SO₂— | —C(O)— | 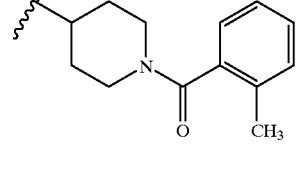 |
| 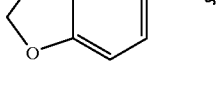 | —SO₂— | —C(O)— | 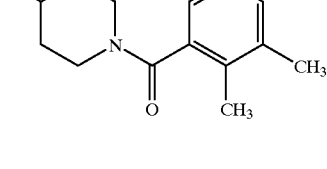 |
| 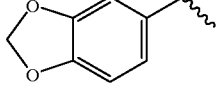 | —SO₂— | 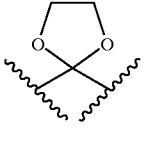 | 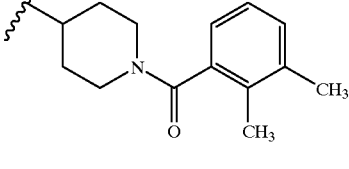 |
| 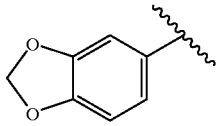 | —SO₂— | 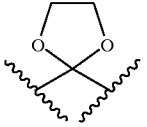 | 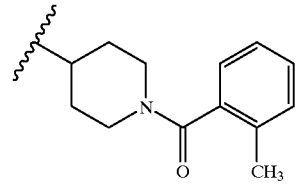 |
| 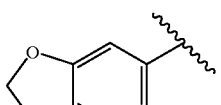 | —SO₂— | 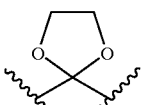 | 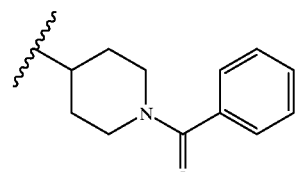 |

-continued
| R | X | R¹, R²¹ | R² |
|---|---|---------|-----|
| 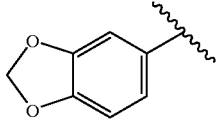 | —SO²— | 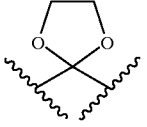 | 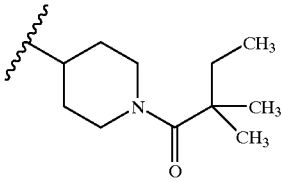 |
| 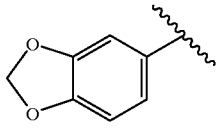 | —SO₂— | 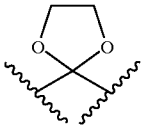 | 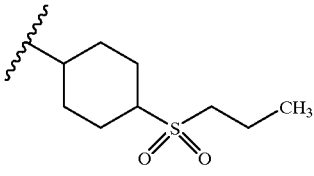 |
| 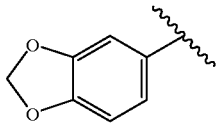 | —SO₂— | 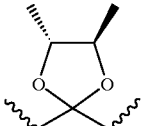 | 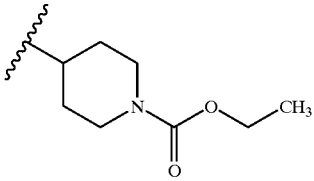 |
| 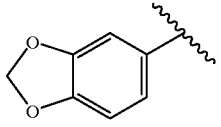 | —SO₂— | 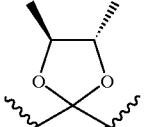 | 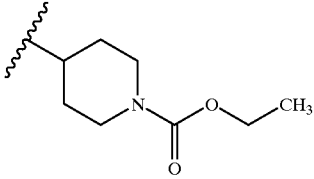 |
| 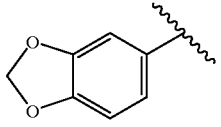 | —CH₂— —C(O)— | | 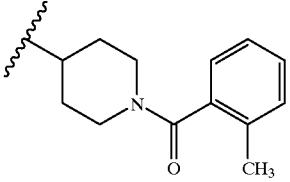 |
| 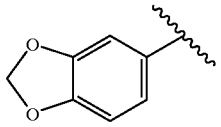 | —CH₂— | 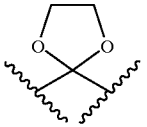 | 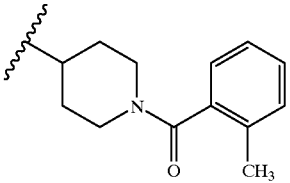 |
| 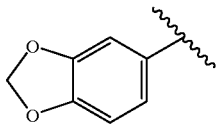 | —SO₂— —CH₂— | | 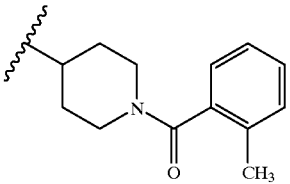 |

-continued

| R | X | R¹, R²¹ | R² |
|---|---|---------|-----|
| 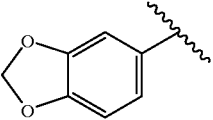 | —CH²— | 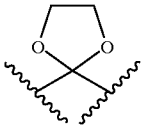 | 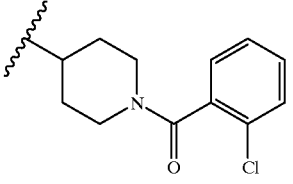 |
| 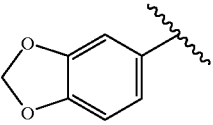 | —SO₂— | 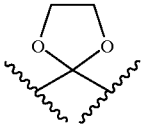 | 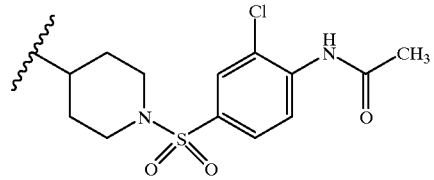 |
| 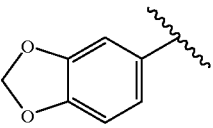 | —SO₂— | 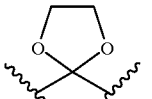 | 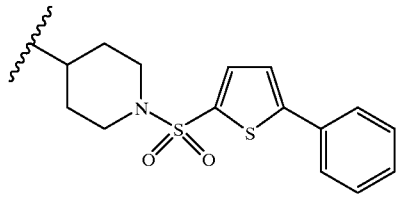 |

14. A pharmaceutical composition which comprises a therapeutically effective amount of a compound as defined in claim 1 in combination with a pharmaceutically acceptable carrier.

15. A method for treating a cognitive disorder in neurodegenerative diseases comprising administering to a patient suffering from said disease an effective amount of a compound of claim 1.

16. A method of treating a cognitive disorder in neurodegenerative diseases comprising administering to a patient suffering from said disease an effective amount of a combination of a compound of claim 1 with an acetylcholinesterase inhibitor.

* * * * *